(12) United States Patent
Cox

(10) Patent No.: US 7,914,577 B2
(45) Date of Patent: *Mar. 29, 2011

(54) APPARATUSES AND METHODS FOR HEART VALVE REPAIR

(75) Inventor: Daniel L. Cox, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 952 days.

This patent is subject to a terminal disclaimer.

(21) Appl. No.: 11/698,729

(22) Filed: Jan. 26, 2007

(65) Prior Publication Data

US 2007/0123978 A1 May 31, 2007

Related U.S. Application Data

(63) Continuation of application No. 10/739,554, filed on Dec. 17, 2003, now Pat. No. 7,226,477, which is a continuation-in-part of application No. 10/295,714, filed on Nov. 15, 2002, now Pat. No. 7,485,143.

(51) Int. Cl.
*A61F 2/24* (2006.01)

(52) U.S. Cl. ..................................... 623/2.37

(58) Field of Classification Search .......... 623/1.1–1.12, 623/1.23, 1.3
See application file for complete search history.

(56) References Cited

U.S. PATENT DOCUMENTS

| | | | |
|---|---|---|---|
| 3,716,058 A | 2/1973 | Tanner et al. | |
| 4,719,924 A | 1/1988 | Crittenden et al. | |
| 4,781,186 A | 11/1988 | Simpson et al. | |
| 4,830,023 A | 5/1989 | de Toledo et al. | |
| 4,920,980 A | 5/1990 | Jackowski | |
| 4,994,067 A | 2/1991 | Summers | |
| 5,040,548 A | 8/1991 | Yock | |
| 5,061,273 A | 10/1991 | Yock | |
| 5,100,418 A | 3/1992 | Yoon et al. | |
| 5,171,233 A | 12/1992 | Amplatz et al. | |
| 5,234,443 A | 8/1993 | Phan et al. | |

(Continued)

FOREIGN PATENT DOCUMENTS

DE 10161543 A1 6/2003

(Continued)

OTHER PUBLICATIONS

Messas, et al., "Chordal Cutting a New Therapeutic Approach for Ischmic Mitral Regurgitaion," 2001, American Heart Association Inc., pp. 1958-1963.

(Continued)

*Primary Examiner* — William H. Matthews
(74) *Attorney, Agent, or Firm* — Jonathan Feuchtwang; Blakely Sokoloff Taylor & Zafman LLP

(57) ABSTRACT

A medical device for treating a defective heart valve. The medical device comprises a delivery sheath and an implantable device moveably disposed within the delivery sheath. The implantable device further comprises a distal expandable basket, a proximal expandable basket, and a connecting member coupling at a first end to the distal expandable basket and at a second end to the proximal expandable basket. Each of the distal expandable basket and proximal expandable basket is in a collapsed state during delivery and an expanded state after deployment. An actuator is releasably coupled to the implantable device. When coupled to the implantable device, the actuator can move the implantable device in a way to allow for positioning of the distal and proximal expandable baskets.

33 Claims, 44 Drawing Sheets

U.S. PATENT DOCUMENTS

| | | |
|---|---|---|
| 5,242,456 A | 9/1993 | Nash et al. |
| 5,350,395 A | 9/1994 | Yock |
| 5,358,479 A | 10/1994 | Wilson |
| 5,383,260 A | 1/1995 | Deschenes et al. |
| 5,431,673 A | 7/1995 | Summers et al. |
| 5,441,483 A | 8/1995 | Avitall |
| 5,451,233 A | 9/1995 | Yock |
| 5,487,757 A | 1/1996 | Truckai et al. |
| 5,495,974 A | 3/1996 | Deschenes et al. |
| 5,518,162 A | 5/1996 | Deschenes et al. |
| 5,522,873 A | 6/1996 | Jackman et al. |
| 5,531,686 A | 7/1996 | Lundquist et al. |
| 5,554,184 A | 9/1996 | Machiraju |
| 5,569,277 A | 10/1996 | Evans et al. |
| 5,571,215 A | 11/1996 | Sterman et al. |
| 5,609,598 A | 3/1997 | Laufer et al. |
| 5,613,937 A | 3/1997 | Garrison et al. |
| 5,617,854 A | 4/1997 | Munsif |
| 5,632,754 A | 5/1997 | Farley et al. |
| 5,640,955 A | 6/1997 | Ockuly et al. |
| 5,642,736 A | 7/1997 | Avitall |
| 5,681,280 A | 10/1997 | Rusk et al. |
| 5,681,346 A | 10/1997 | Orth et al. |
| 5,682,906 A | 11/1997 | Sterman et al. |
| 5,687,723 A | 11/1997 | Avitall |
| 5,728,129 A | 3/1998 | Summers |
| 5,782,828 A | 7/1998 | Chen et al. |
| 5,810,882 A | 9/1998 | Bolduc et al. |
| 5,823,955 A | 10/1998 | Kuck et al. |
| 5,824,008 A | 10/1998 | Bolduc et al. |
| 5,865,800 A | 2/1999 | Mirarchi et al. |
| 5,868,733 A | 2/1999 | Ockuly et al. |
| 5,868,767 A | 2/1999 | Farley et al. |
| 5,916,213 A | 6/1999 | Haissaguerre et al. |
| 5,961,440 A | 10/1999 | Schweich, Jr. et al. |
| 5,964,772 A | 10/1999 | Bolduc et al. |
| 5,972,022 A | 10/1999 | Huxel |
| 5,989,284 A | 11/1999 | Laufer |
| 6,001,095 A | 12/1999 | de la Rama et al. |
| 6,001,104 A | 12/1999 | Benderev et al. |
| 6,001,127 A | 12/1999 | Schoon et al. |
| 6,004,332 A | 12/1999 | Yoon et al. |
| 6,017,358 A | 1/2000 | Yoon et al. |
| 6,021,340 A | 2/2000 | Randolph et al. |
| 6,027,514 A | 2/2000 | Stine |
| 6,036,715 A | 3/2000 | Yock |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Schweich, Jr. et al. |
| 6,090,096 A | 7/2000 | St. Goar et al. |
| 6,093,199 A | 7/2000 | Brown et al. |
| 6,110,100 A | 8/2000 | Talpade |
| 6,113,609 A | 9/2000 | Adams |
| 6,117,176 A | 9/2000 | Chen |
| 6,123,699 A | 9/2000 | Webster, Jr. |
| 6,149,669 A | 11/2000 | Li |
| 6,161,543 A | 12/2000 | Cox et al. |
| 6,162,168 A | 12/2000 | Schweich, Jr. et al. |
| 6,164,283 A | 12/2000 | Lesh |
| 6,165,119 A | 12/2000 | Schweich, Jr. et al. |
| 6,165,120 A | 12/2000 | Schweich, Jr. et al. |
| 6,165,164 A | 12/2000 | Hill et al. |
| 6,165,183 A | 12/2000 | Kuehn et al. |
| 6,165,197 A | 12/2000 | Yock |
| 6,174,323 B1 | 1/2001 | Biggs et al. |
| 6,176,240 B1 | 1/2001 | Nikolchev et al. |
| 6,178,346 B1 | 1/2001 | Amundson et al. |
| 6,182,664 B1 | 2/2001 | Cosgrove |
| 6,183,411 B1 | 2/2001 | Mortier et al. |
| 6,187,040 B1 | 2/2001 | Wright |
| 6,190,401 B1 | 2/2001 | Green et al. |
| 6,190,408 B1 | 2/2001 | Melvin |
| 6,203,531 B1 | 3/2001 | Ockuly et al. |
| 6,210,407 B1 | 4/2001 | Webster, Jr. |
| 6,210,432 B1 | 4/2001 | Solem et al. |
| 6,231,587 B1 | 5/2001 | Makower |
| 6,241,728 B1 | 6/2001 | Gaiser et al. |
| 6,254,568 B1 | 7/2001 | Ponzi |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,267,781 B1 | 7/2001 | Tu |
| 6,269,819 B1 | 8/2001 | Oz et al. |
| 6,270,526 B1 | 8/2001 | Cox |
| 6,283,127 B1 | 9/2001 | Sterman et al. |
| 6,283,962 B1 | 9/2001 | Tu et al. |
| 6,299,622 B1 | 10/2001 | Snow et al. |
| 6,306,133 B1 | 10/2001 | Tu et al. |
| 6,312,447 B1 | 11/2001 | Grimes |
| 6,325,823 B1 | 12/2001 | Horzewski et al. |
| 6,355,030 B1 | 3/2002 | Adrich et al. |
| 6,371,978 B1 | 4/2002 | Wilson |
| 6,374,476 B1 | 4/2002 | Ponzi et al. |
| 6,402,780 B2 | 6/2002 | Williamson, IV et al. |
| 6,402,781 B1 | 6/2002 | Langberg et al. |
| 6,408,214 B1 | 6/2002 | Williams et al. |
| 6,419,696 B1 | 7/2002 | Ortiz et al. |
| 6,461,366 B1 | 10/2002 | Seguin |
| 6,482,224 B1 | 11/2002 | Michler et al. |
| 6,488,689 B1 | 12/2002 | Kaplan et al. |
| 6,493,575 B1 | 12/2002 | Kesten et al. |
| 6,497,707 B1 | 12/2002 | Bowman et al. |
| 6,500,167 B1 | 12/2002 | Webster, Jr. |
| 6,537,198 B1 | 3/2003 | Vidlund et al. |
| 6,537,314 B2 | 3/2003 | Langberg et al. |
| 6,551,271 B2 | 4/2003 | Nguyen |
| 6,554,794 B1 | 4/2003 | Mueller et al. |
| 6,585,718 B2 | 7/2003 | Hayzelden et al. |
| 6,599,311 B1 | 7/2003 | Biggs et al. |
| 6,605,086 B2 | 8/2003 | Hayzelden et al. |
| 6,610,058 B2 | 8/2003 | Flores |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Groar et al. |
| 6,638,289 B1 | 10/2003 | Johnson et al. |
| 6,648,903 B1 | 11/2003 | Pierson, III |
| 6,656,221 B2 | 12/2003 | Taylor et al. |
| 6,676,702 B2 | 1/2004 | Mathis |
| 6,706,065 B2 | 3/2004 | Langberg et al. |
| 6,709,442 B2 | 3/2004 | Miller et al. |
| 6,709,456 B2 | 3/2004 | Langberg et al. |
| 6,712,804 B2 | 3/2004 | Roue et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,733,500 B2 | 5/2004 | Kelley et al. |
| 6,755,812 B2 | 6/2004 | Peterson et al. |
| 6,761,734 B2 | 7/2004 | Suhr |
| 6,764,510 B2 | 7/2004 | Vidlund et al. |
| 6,790,231 B2 | 9/2004 | Liddicoat et al. |
| 6,800,090 B2 | 10/2004 | Alferness et al. |
| 6,810,882 B2 | 11/2004 | Langberg et al. |
| 6,824,562 B2 | 11/2004 | Mathis et al. |
| 6,852,124 B2 | 2/2005 | Cox et al. |
| 6,890,353 B2 | 5/2005 | Cohn et al. |
| 6,905,476 B2 | 6/2005 | Ponzi |
| 6,908,478 B2 | 6/2005 | Alferness et al. |
| 6,911,035 B1 | 6/2005 | Blomme |
| 6,960,229 B2 | 11/2005 | Mathis et al. |
| 6,964,683 B2 | 11/2005 | Kowalsky et al. |
| 6,966,926 B2 | 11/2005 | Mathis |
| 6,989,028 B2 | 1/2006 | Lashinski et al. |
| 6,997,951 B2 | 2/2006 | Solem et al. |
| 7,226,477 B2 * | 6/2007 | Cox ............................. 623/2.37 |
| 2001/0003986 A1 | 6/2001 | Cosgrove |
| 2001/0005787 A1 | 6/2001 | Oz et al. |
| 2001/0018611 A1 | 8/2001 | Solem et al. |
| 2001/0027322 A1 | 10/2001 | Bowman |
| 2001/0044568 A1 | 11/2001 | Langberg et al. |
| 2002/0010483 A1 | 1/2002 | Folmer et al. |
| 2002/0010486 A1 | 1/2002 | Hirt |
| 2002/0013571 A1 | 1/2002 | Goldfarb et al. |
| 2002/0016628 A1 | 2/2002 | Langberg et al. |
| 2002/0026216 A1 | 2/2002 | Grimes |
| 2002/0035361 A1 | 3/2002 | Houser et al. |

| | | |
|---|---|---|
| 2002/0042651 A1 | 4/2002 | Liddicoat et al. |
| 2002/0077647 A1 | 6/2002 | Snow et al. |
| 2002/0087169 A1 | 7/2002 | Brock et al. |
| 2002/0087173 A1 | 7/2002 | Alferness et al. |
| 2002/0103492 A1 | 8/2002 | Kaplan et al. |
| 2002/0103532 A1 | 8/2002 | Langberg et al. |
| 2002/0103533 A1 | 8/2002 | Langberg et al. |
| 2002/0111637 A1 | 8/2002 | Kaplan et al. |
| 2002/0161330 A1 | 10/2002 | Nguyen |
| 2002/0165484 A1 | 11/2002 | Bowe et al. |
| 2002/0165533 A1 | 11/2002 | Flores |
| 2002/0165534 A1 | 11/2002 | Hayzelden et al. |
| 2002/0169502 A1 | 11/2002 | Mathis |
| 2002/0169504 A1 | 11/2002 | Alferness et al. |
| 2002/0183836 A1 | 12/2002 | Liddicoat et al. |
| 2002/0183837 A1 | 12/2002 | Streeter et al. |
| 2002/0183841 A1 | 12/2002 | Cohn et al. |
| 2002/0188170 A1 | 12/2002 | Santamore et al. |
| 2003/0050598 A1 | 3/2003 | Hayzelden et al. |
| 2003/0069593 A1 | 4/2003 | Tremulis et al. |
| 2003/0078465 A1 | 4/2003 | Pai et al. |
| 2003/0083538 A1 | 5/2003 | Adams et al. |
| 2003/0093071 A1 | 5/2003 | Hauck et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130731 A1 | 7/2003 | Vidlund et al. |
| 2003/0144697 A1 | 7/2003 | Mathis |
| 2003/0144732 A1 | 7/2003 | Cosgrove et al. |
| 2003/0167071 A1 | 9/2003 | Martin et al. |
| 2003/0171776 A1 | 9/2003 | Adams et al. |
| 2003/0212453 A1 | 11/2003 | Mathis et al. |
| 2003/0216764 A1 | 11/2003 | Tu et al. |
| 2004/0010231 A1 | 1/2004 | Leonhardt et al. |
| 2004/0010305 A1 | 1/2004 | Alferness et al. |
| 2004/0019377 A1 | 1/2004 | Taylor et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0059351 A1 | 3/2004 | Eigler et al. |
| 2004/0098092 A1 | 5/2004 | Butaric et al. |
| 2004/0138683 A1 | 7/2004 | Shelton et al. |
| 2004/0138744 A1 | 7/2004 | Lashinski et al. |
| 2004/0148020 A1 | 7/2004 | Vidlund et al. |
| 2004/0153052 A1 | 8/2004 | Mathis |
| 2004/0153147 A1 | 8/2004 | Mathis |
| 2005/0055089 A1 | 3/2005 | Macoviak et al. |
| 2005/0267571 A1 | 12/2005 | Spence et al. |
| 2005/0267573 A9 | 12/2005 | Macoviak et al. |
| 2006/0041306 A1 | 2/2006 | Vidlund et al. |
| 2006/0095025 A1 | 5/2006 | Levine et al. |

FOREIGN PATENT DOCUMENTS

| | | |
|---|---|---|
| EP | 0377269 A1 | 7/1990 |
| WO | WO 98/29041 A1 | 7/1998 |
| WO | WO 99/00059 | 1/1999 |
| WO | WO 99/13777 | 3/1999 |
| WO | WO 99/30647 A1 | 6/1999 |
| WO | WO 99/44534 A1 | 9/1999 |
| WO | WO 00/03759 | 1/2000 |
| WO | WO 00/06026 A2 | 2/2000 |
| WO | WO 00/06027 A2 | 2/2000 |
| WO | WO 00/06028 A1 | 2/2000 |
| WO | WO 00/16700 A1 | 3/2000 |
| WO | WO 00/60995 | 10/2000 |
| WO | WO 01/00111 A1 | 1/2001 |
| WO | WO 01/00114 A1 | 1/2001 |
| WO | WO 01/26557 A1 | 4/2001 |
| WO | WO 01/28432 A1 | 4/2001 |
| WO | WO 01/28455 A1 | 4/2001 |
| WO | WO 01/49213 A2 | 7/2001 |
| WO | WO 01/49213 A3 | 7/2001 |
| WO | WO 01/54618 A1 | 8/2001 |
| WO | WO 01/89440 A2 | 11/2001 |
| WO | WO 02/00099 A2 | 1/2002 |
| WO | WO 02/01999 A2 | 1/2002 |
| WO | WO 02/34167 A2 | 5/2002 |
| WO | WO 02/39925 A2 | 5/2002 |
| WO | WO 02/053206 A2 | 7/2002 |
| WO | WO 02/060352 A1 | 8/2002 |
| WO | WO 02/062263 A2 | 8/2002 |
| WO | WO 02/062263 A3 | 8/2002 |
| WO | WO 02/062270 A1 | 8/2002 |
| WO | WO 02/062408 A2 | 8/2002 |
| WO | WO 02/063533 | 8/2002 |
| WO | WO 02/078576 | 10/2002 |
| WO | WO 03/049619 A2 | 6/2003 |
| WO | WO 03/073913 A2 | 9/2003 |
| WO | WO 2004/012789 A2 | 2/2004 |
| WO | WO 2004/014282 A2 | 2/2004 |

OTHER PUBLICATIONS

PCT Invitation to Pay Additional fees for PCT International Appln. No. US03/36633, mailed May 19, 2004 (5 pages).

PCT Report for PCT International Patent Application PCT/US2004/031403, mailed Jun. 15, 2005. 5 pgs.

Bonow, Robert O. et al. "Guidelines for the Management of Patients with Valvular Heart Disease," Report of American College of Cardiology/American Heart Assoc. Task Force on Practice Guidelines (Committee on Management of Patients with Valvular Heart Disease), American College of Cardiology and American Heart Assoc., Inc., 1998, pp. 1949-1984.

* cited by examiner

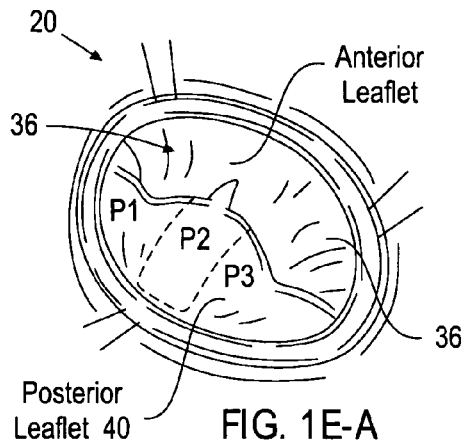
FIG. 1E-A
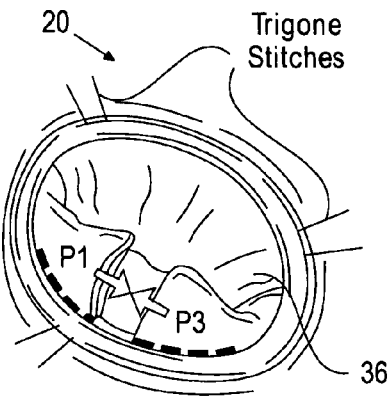
FIG. 1E-B
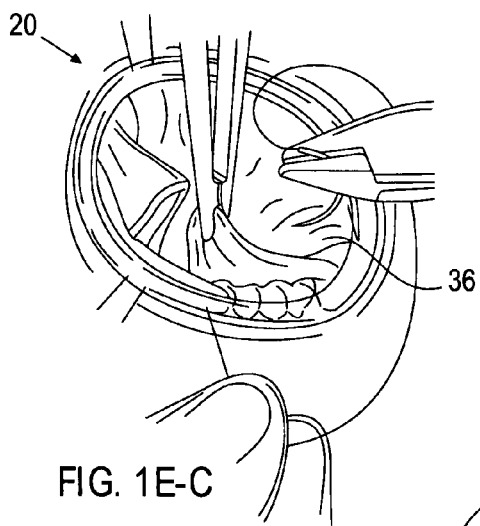
FIG. 1E-C
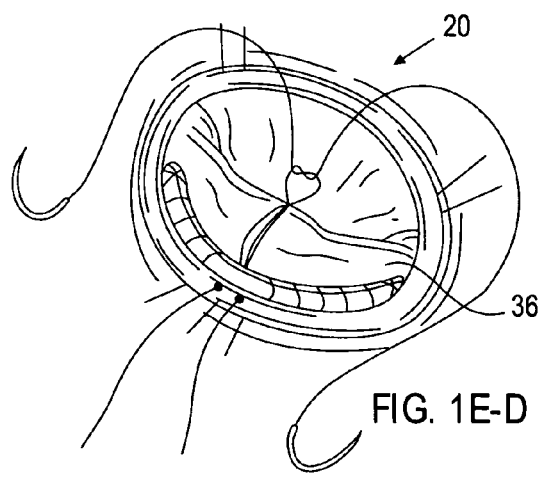
FIG. 1E-D
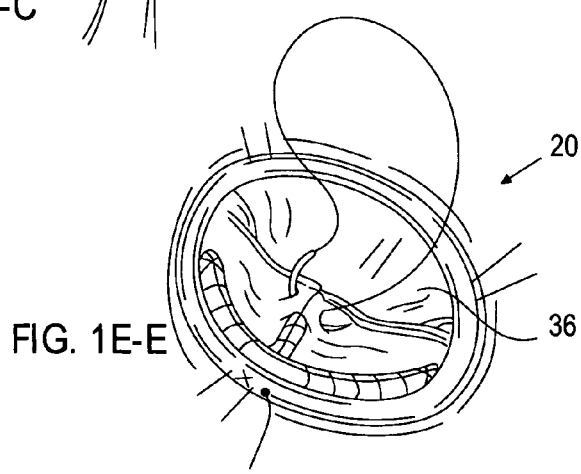
FIG. 1E-E

FIG. 11
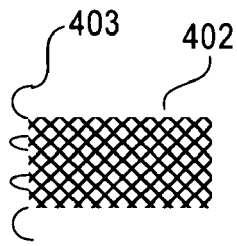
FIG. 12
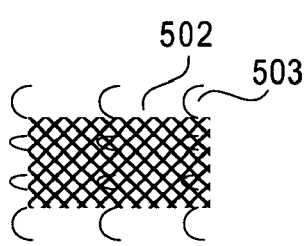
FIG. 13
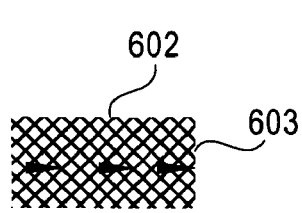
FIG. 14
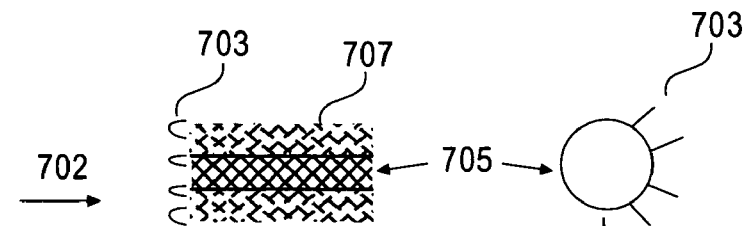
FIG. 15A  FIG. 15B
FIG. 16A
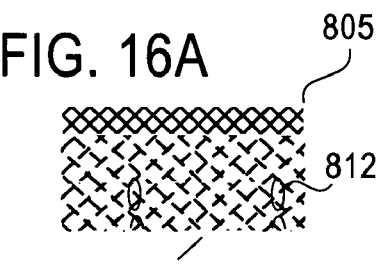
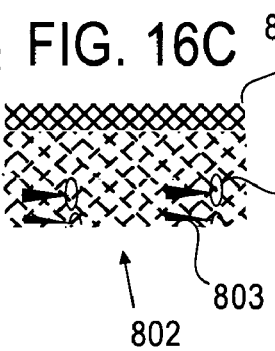
FIG. 16B
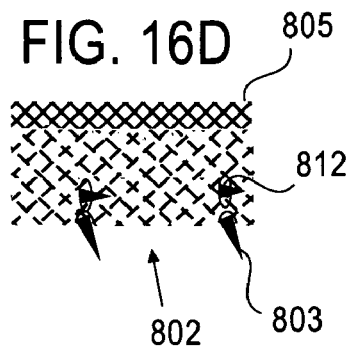
FIG. 16C  FIG. 16D
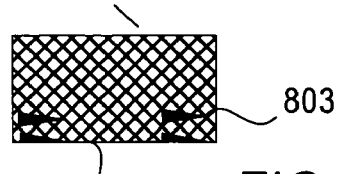

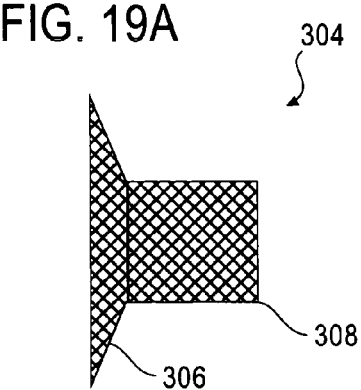
FIG. 19A
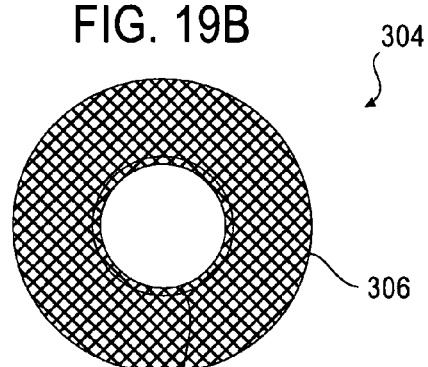
FIG. 19B
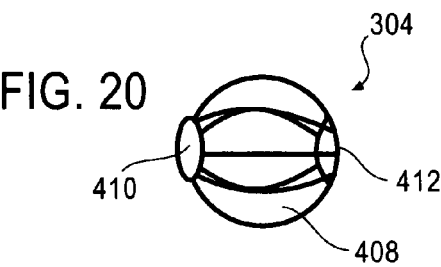
FIG. 20
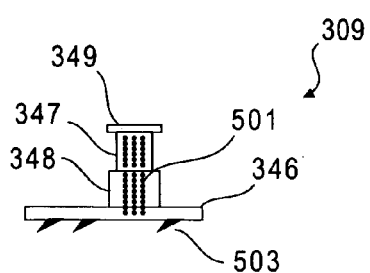
FIG. 21A
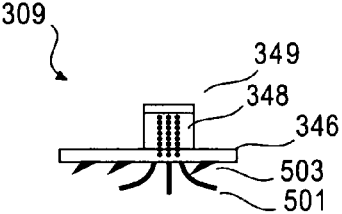
FIG. 21B
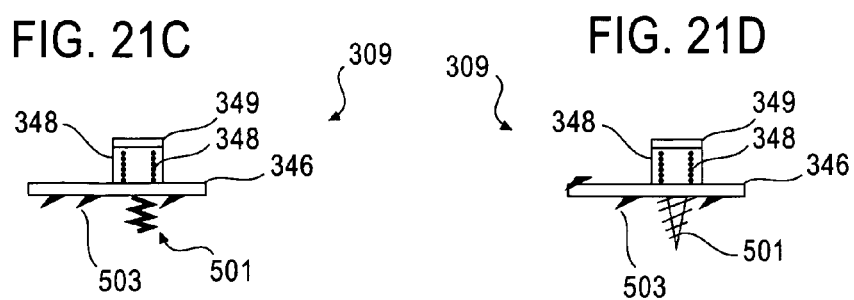
FIG. 21C
FIG. 21D

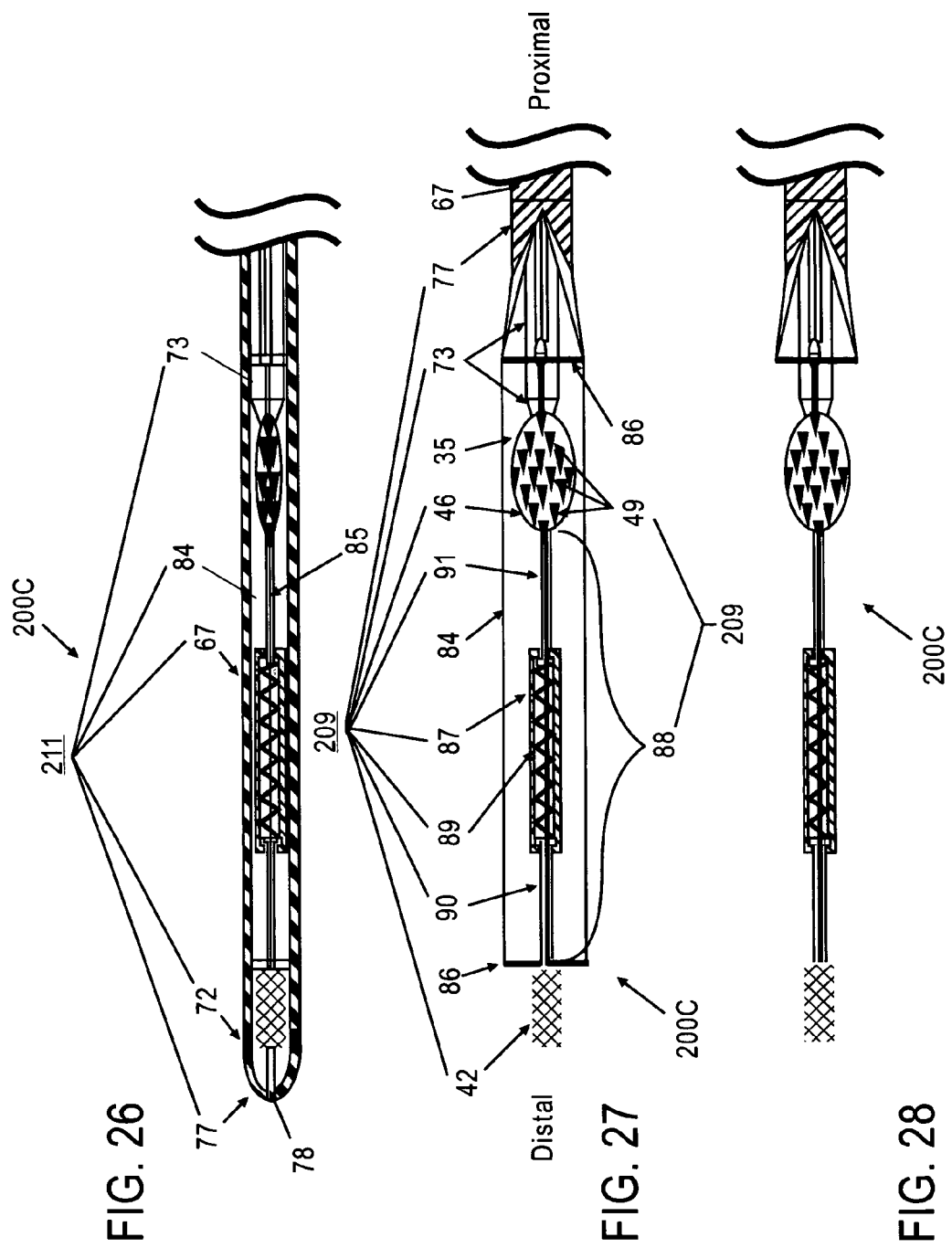

Top View          Front View

FIG. 65A
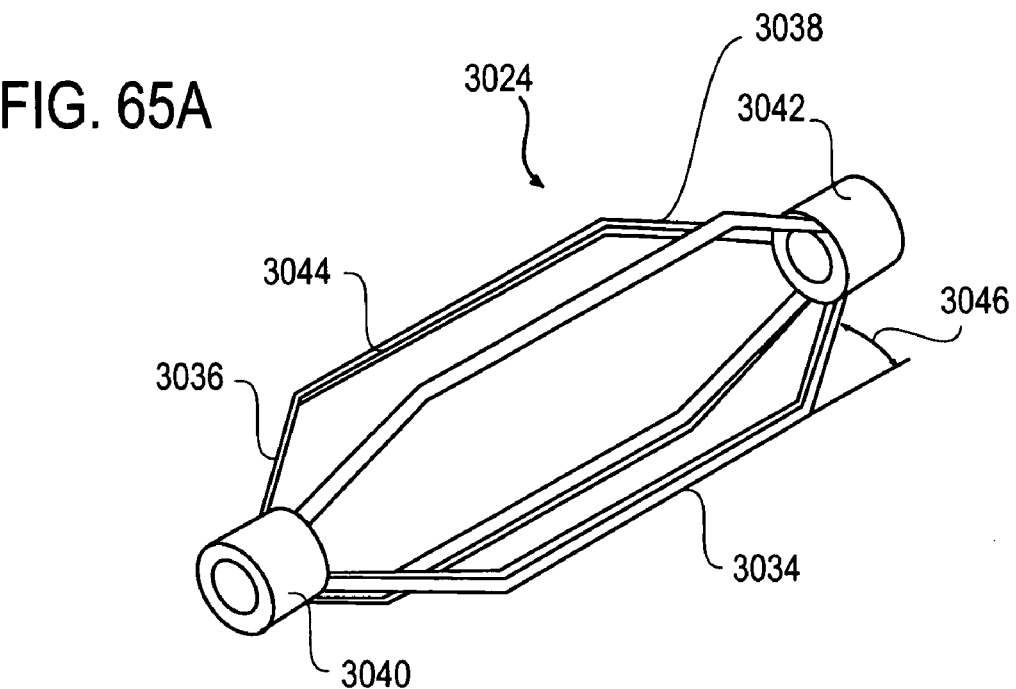
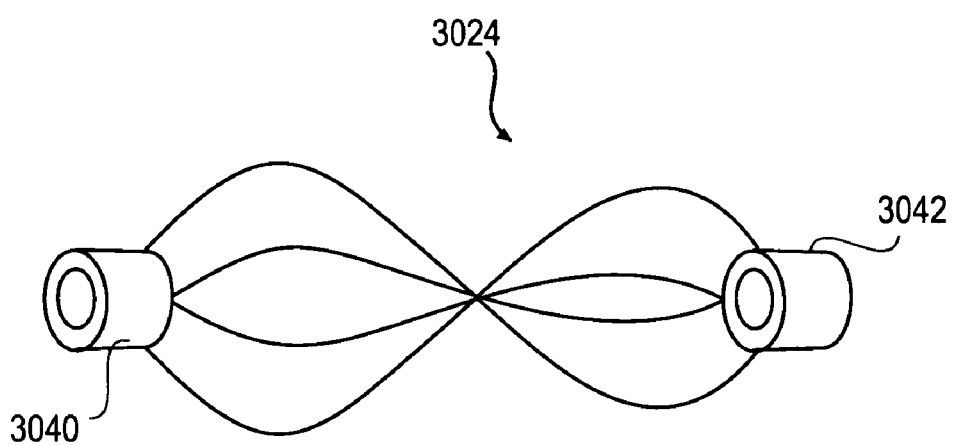
FIG. 65B

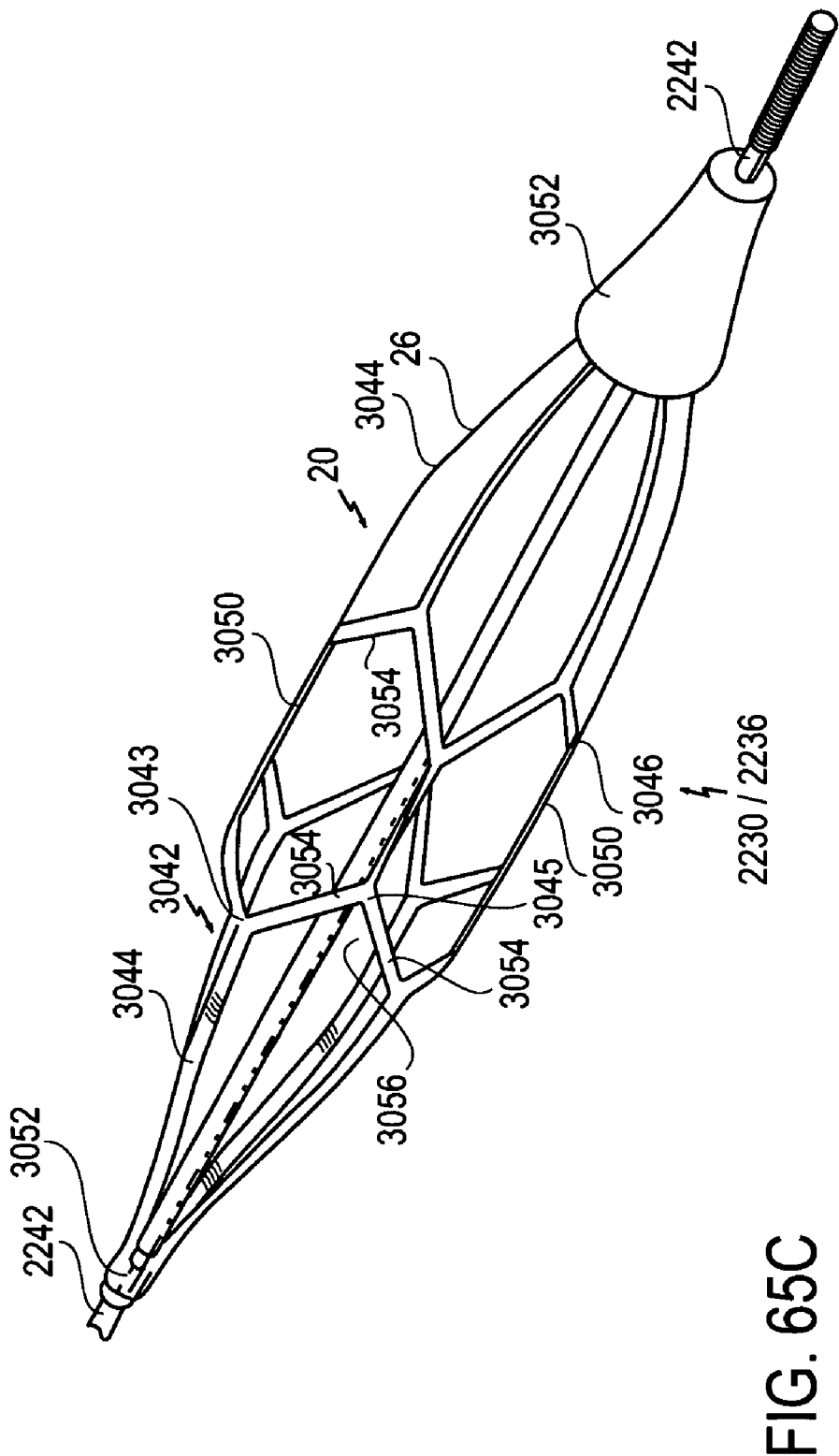

APPARATUSES AND METHODS FOR HEART VALVE REPAIR

This application is a continuation of U.S. patent application Ser. No. 10/739,554 titled "Apparatuses and Methods for Heart Valve Repair" filed on Dec. 17, 2003 now U.S. Pat. No. 7,226,477, which is a continuation-in-part of U.S. patent application Ser. No. 10/295,714 filed on Nov. 15, 2002 now U.S. Pat. No. 7,485,143. Both of these aforementioned patent applications are hereby incorporated herein by reference.

BACKGROUND OF THE INVENTION

1. Field of the Invention

The present invention involves annuloplasty devices and delivery devices for the annuloplasty devices that are used for treating a medical condition such as a defective mitral valve.

2. Discussion of Related Art

FIG. 1A illustrates a heart 10. There are four valves in the heart 10 that serve to direct the flow of blood through the two sides of the heart 10 in a forward direction. The four valves are a mitral valve 20, an aortic valve 18, a tricuspid valve 60, and a pulmonary valve 62 as illustrated in FIG. 1A. The mitral valve 20 is located between the left atrium 12 and the left ventricle 14. The aortic valve 18 is located between the left ventricle 14 and the aorta 16. These two valves direct oxygenated blood coming from the lungs, through the left side of the heart, into the aorta 16 for distribution to the body. The tricuspid valve 60 is located between the right atrium 22 and the right ventricle 24. The pulmonary valve 62 is located between the right ventricle 24 and the pulmonary artery 26. These two valves direct de-oxygenated blood coming from the body, through the right side of the heart, into the pulmonary artery 26 for distribution to the lungs, where it again becomes re-oxygenated and distributed to the mitral valve 20 and the aortic valve 18.

All of the heart valves are complex structures. Each valve consists of moveable "leaflets" that are designed to open and close. The mitral valve has two leaflets and the tricuspid valve has three. The aortic and pulmonary valves have leaflets that are more aptly termed "cusps" and are shaped somewhat like a half-moon. The aortic and pulmonary valves each have three cusps.

Blood flows into the left ventricle 14 through the mitral valve 20 that opens during diastole. Once the left ventricular cavity has filled, the left ventricle 14 contracts during systole. The mitral valve 20 closes (the leaflets of the mitral valve 20 re-approximate) while the aortic valve 18 opens during systole allowing the oxygenated blood to be ejected from the left ventricle 14 into the aorta 16. A normal mitral valve allows blood to flow into the left ventricle and does not allow leaking or regurgitating back into the left atrium and then into the lungs during systole. The aortic valve allows blood to flow into the aorta and does not allow leaking (or regurgitating) back into the left ventricle. The tricuspid valve 60 functions similarly to the mitral valve to allow deoxygenated blood to flow into the right ventricle 24. The pulmonary valve 62 functions in the same manner as the aortic valve 18 in response to relaxation and contraction of the right ventricle 24 in moving de-oxygenated blood into the pulmonary artery and thence to the lungs for re-oxygenation.

With relaxation and expansion of the ventricles (diastole), the mitral and tricuspid valves open, while the aortic and pulmonary valves close. When the ventricles contract (systole), the mitral and tricuspid valves close and the aortic and pulmonary valves open. In this manner, blood is propelled through both sides of the heart.

The anatomy of the heart and the structure and terminology of heart valves are described and illustrated in detail in numerous reference works on anatomy and cardiac surgery, including standard texts such as Surgery of the Chest (Sabiston and Spencer, eds., Saunders Publ., Philadelphia) and Cardiac Surgery by Kirklin and Barrett-Boyes.

In chronic heart failure (CHF), the size of the heart becomes enlarged. This enlargement can cause the annular size of the valves that separate the atria from the ventricles to also become enlarged. The mitral valve is generally the most affected and has the most serious effects on patient health. FIG. 1B illustrates a sectional view of the positions of the cardiac valves such as the mitral valve 20 present in the heart 10. The annular enlargements can become so pronounced that the leaflets of the valve(s) are unable to effectively close.

The annular enlargement most profoundly affects the posterior leaflet 25 of the mitral valve 20. FIG. 1C illustrates a sectional view of the expansion of the annulus 28 of the mitral valve 20. As shown, the annulus 28 expands from a cross-sectional size indicated by the number 21 to the expanded cross-sectional size indicated by the number 23. The expansion/enlargement typically affects the posterior leaflet 25 of the mitral valve 20. During systole, due to the annular enlargement, the valve leaflets do not meet (valve not fully closed, no coaptation), thus some amount of blood flows the wrong way back through the valve from the ventricle and back into the atrium (valve regurgitation) where it raises the pressure in the atrium. This is termed "Mitral Valve Regurgitation" or MVR. MVR reduces the amount of blood pumped by the heart to the body. This reduction in blood flow can be life threatening, especially in patients that have lost ventricular tissue (i.e. heart attack victims), have contraction synchronization problems and/or other problems that reduce the heart's ability to act as a pump.

Regurgitation is common, and is occurring in about 7% of the population. Mitral valve regurgitation is caused by a number of conditions, including genetic defects, infections, coronary artery disease (CAD), myocardial infarction (MI) or congestive heart failure (CHF). Most cases are mild and if the symptoms are bothersome, they can usually be controlled with drugs.

In more serious cases, the faulty or defective valve can be repaired with a surgical procedure such as an annuloplasty. As illustrated in FIG. 1D, an annuloplasty 30 is a surgical procedure in which a synthetic ring 32 is placed around the valve rim (annulus) 34. Sutures 38 are put into the valve annulus 34 and the synthetic ring 32. This causes proper closing by shrinking the size of the valve opening 36. The synthetic ring 32 also reduces and reshapes the annulus 34 to move the posterior leaflet toward the anterior leaflet. FIGS. 1E-A through 1E-E illustrate another surgical procedure in which a heart valve such as the mitral valve 20 is repaired by reconstruction. First, in FIG. 1E-A, a section P2 from the posterior leaflet 40 of the mitral valve 20 is excised. Then, sequentially as shown in FIGS. 1E-A through 1E-E, sections P1 and P3 of the posterior leaflet 40 are sutured together. The reconstruction shrinks the size of the valve opening 36. In some instances, a faulty or defective valve must be surgically replaced with a new valve. Examples of new valves include homograft valves (valves harvested from human cadavers), artificial mitral valves, and mechanical valves.

All of the procedures above are typically major surgical procedures that require the opening of the chest by sternotomy or at best through small incisions in the chest wall, performing a heart lung bypass and stopping the heart beat. While surgical procedures such as those mentioned can successfully reconstruct the valve back to a non-regurgitant state, this problem is often associated with Chronic Heart Failure (CHF) and/or other debilitating diseases and thus, the sufferers of the regurgitant valve are often unable to tolerate the required open heart surgery. In CHF patients, the heart is progressively less able to pump sufficient blood to meet the body's needs, usually due to the continuing enlargement of the left ventricle (and adjacent structures) in response to high blood pressure, high heart rate, ECG conduction/timing problems and/or insults to the ventricular tissue, such as Myocardial Infarct (MI). As the body's cardiac compensatory mechanisms act to maintain blood flow (cardiac output), the increased stress and metabolic impacts cause further cardiac enlargement and other detrimental changes. The onset of mitral valve regurgitation further reduces cardiac output and, thus accelerates the CHF process. Therefore, there is a need for a less invasive and traumatic way to treat mitral valve regurgitation (MVR).

SUMMARY

The exemplary embodiments of the present invention disclose apparatuses and methods for treating a valve such as a defective heart valve. The exemplary embodiments of the present invention also disclose annuloplasty devices and delivery devices used to deliver/deploy the annuloplasty devices to treat such a valve.

One exemplary embodiment pertains to a medical device that comprises a delivery sheath, an implantable device moveably disposed within the delivery sheath, and an actuator releasably coupling to the implantable device. The implantable device further comprises a distal expandable basket, a proximal expandable basket, and a connecting member coupling at a first end to the distal expandable basket and at a second end to the proximal expandable basket. The distal expandable basket and proximal expandable basket are deliverable in a compressed state and deployed to an expanded state. The actuator is used to facilitate the deployment of the implantable device.

Another exemplary embodiment pertains to a method of deploying an implantable device in a blood vessel. The method comprises providing a medical device that comprises a delivery sheath, an implantable device moveably disposed within the delivery sheath, and an actuator releasably coupling to the implantable device. The implantable device comprises a distal expandable basket, a proximal expandable basket, and a connecting member coupling at a first end to the distal expandable basket and at a second end to the proximal expandable basket. The method further comprises deploying the implantable device into a blood vessel with the distal expandable basket and the proximal expandable basket in a collapsed state. When the distal expandable basket is in a proper position, the delivery sheath is withdrawn to allow the distal expandable basket to expand and rest against the inner wall of the blood vessel. The proximal expandable basket is then deployed while tension is applied to the actuator. Once the proximal expandable basket is pulled to a proper position along the blood vessel, the delivery sheath is withdrawn to allow the proximal expandable basket to expand to rest against the inner wall of the blood vessel. The implantable device is, after deployments of the distal expandable basket, proximal expandable basket, and the connecting member, capable of reshaping the blood vessel. In another embodiment, the blood vessel has a first curvature and when the implantable device is deployed, the implantable device changes the first curvature to a second curvature wherein the second curvature is smaller than the first curvature. The blood vessel may be a coronary sinus in one embodiment.

The methods of treating mitral valve using the exemplary embodiments of the present invention are also disclosed and other exemplary embodiments are disclosed.

BRIEF DESCRIPTION OF THE DRAWINGS

The present invention is illustrated by way of example and not limitation in the figures of the accompanying drawings, in which like references indicate similar elements and in which:

FIGS. 1E-A through 1E-E are illustrations of a reconstruction procedure to reduce the size of a defective valve;

FIGS. 11-14, 15A-15B, 16A-16D, and 17-18 illustrate exemplary embodiments of distal anchoring members that can be used for annuloplasty devices in accordance with the embodiments of the present invention;

FIGS. 19A-19B, 20, 21A-21D, and 22A-22B illustrate exemplary embodiments of proximal anchoring members that can be used for annuloplasty devices in accordance with the embodiments of the present invention;

FIGS. 26-28 illustrate another exemplary embodiment of a annuloplasty device in a delivery device that can be delivered into a coronary sinus in accordance with the embodiments of the present invention;

FIGS. 65A-65C illustrate exemplary embodiments of a distal or proximal expandable basket for the annuloplasty device shown in FIGS. 62A-62D.

DETAILED DESCRIPTION

Figure 1A:
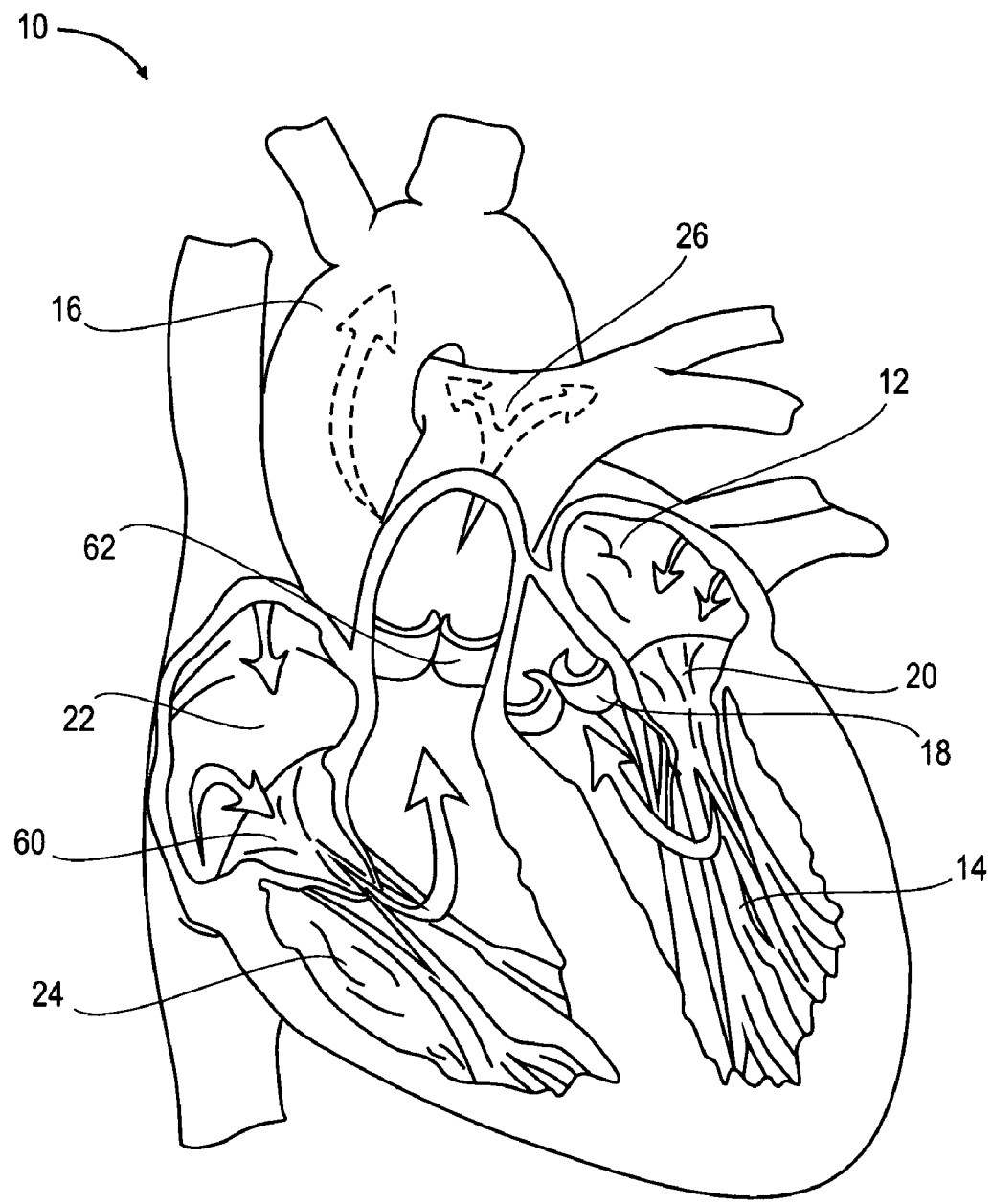
FIG. 1A is an illustration of a heart.
Figure 1B:
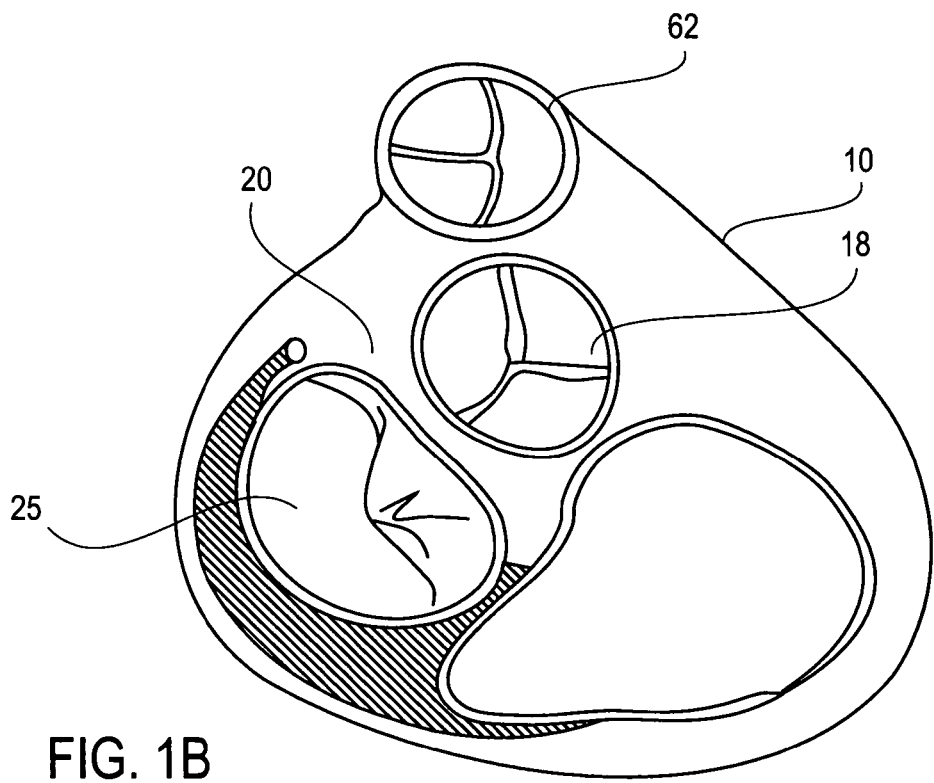
FIGS. 1B-1C illustrate a normal mitral valve and an enlarged mitral valve, respectively.
Figure 1C:
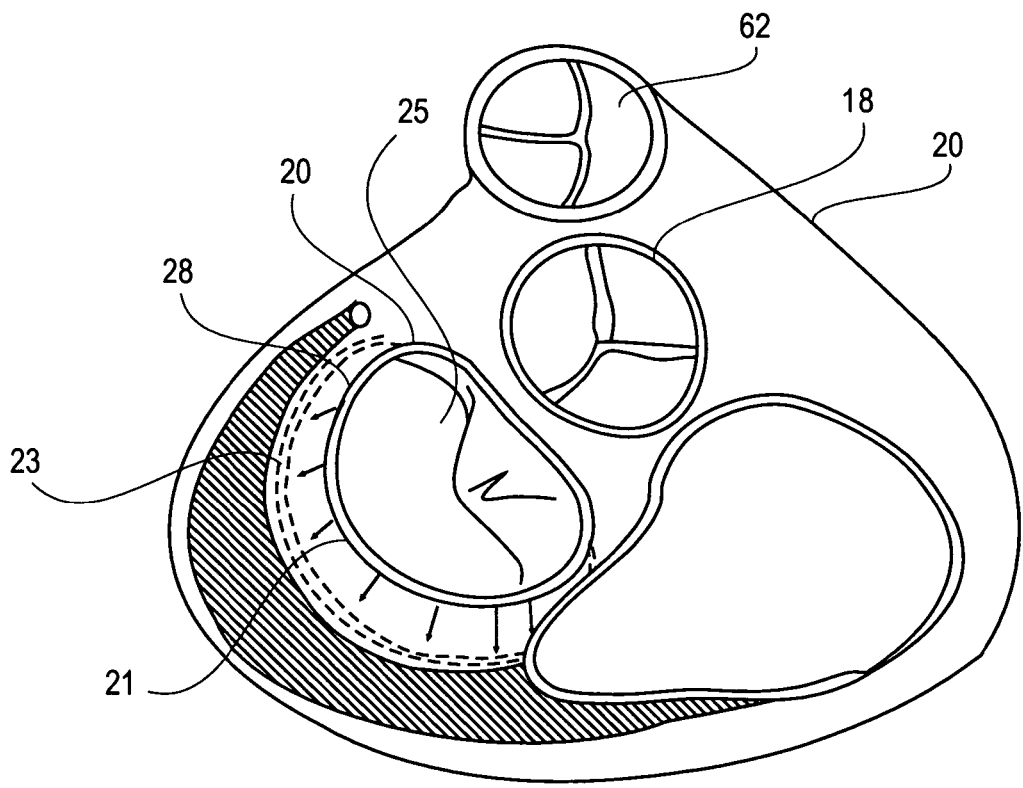
Figure 1D:
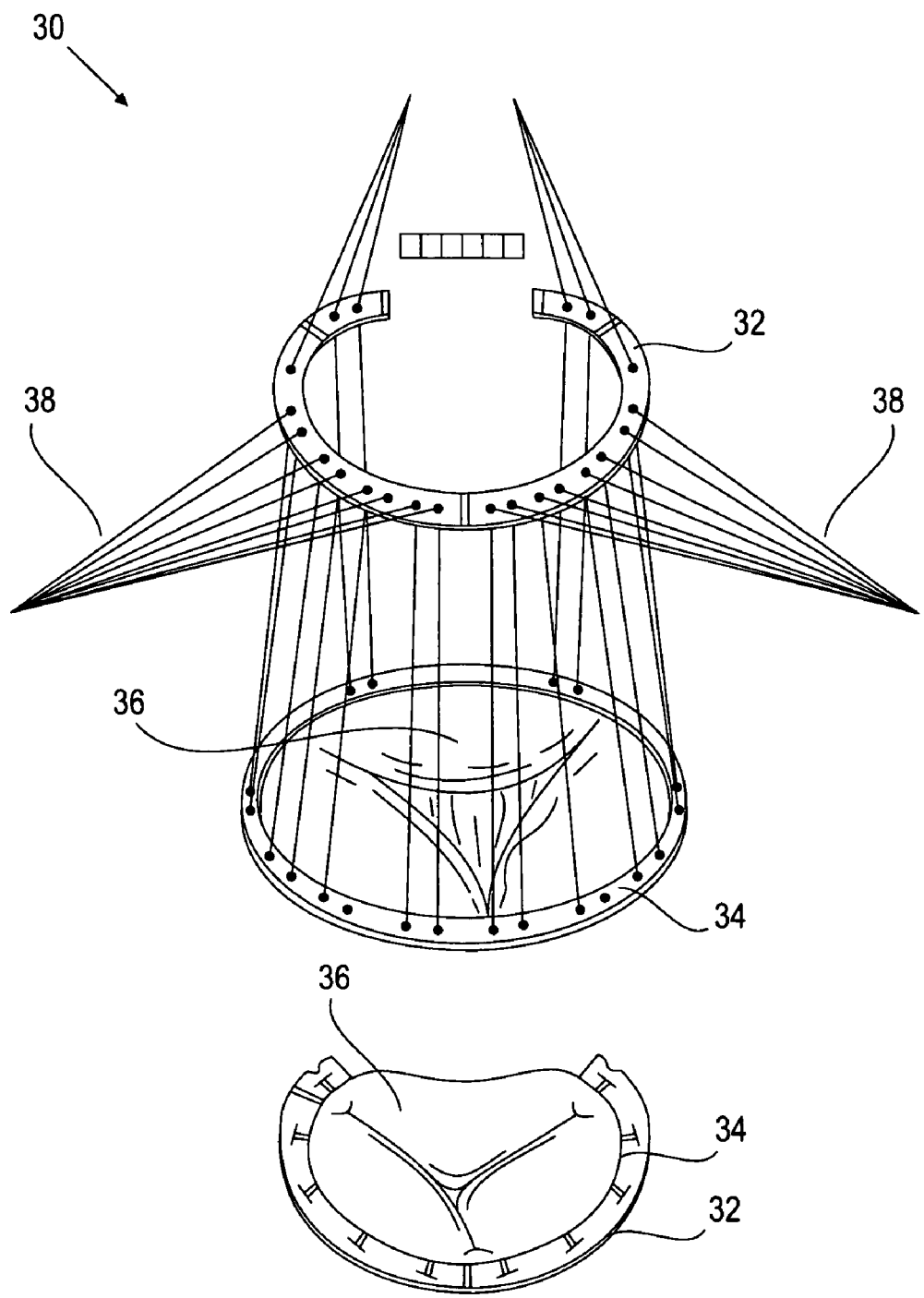
FIG. 1D is an illustration of an annuloplasty procedure to constrict a valve (e.g., a mitral valve)

The exemplary embodiments of the present invention pertain to novel annuloplasty devices, delivery devices to deploy/deliver the annuloplasty devices, and methods of using these annuloplasty devices to treat medical conditions such as defective or faulty heart valves. In the following description, for purposes of explanation, numerous specific details are set forth in order to provide a thorough understanding of the present invention. It will be evident, however, to one skilled in the art, that the present invention may be practiced without these specific details. In other instances, specific apparatus structures and methods have not been described so as not to obscure the present invention. The following description and drawings are illustrative of the invention and are not to be construed as limiting the invention.

In some exemplary embodiments of the present invention, an annuloplasty device used for treating a faulty heart valve such as those seen in MVR includes an annuloplasty device that reduces the cross-sectional size of the annulus of the mitral valve or brings the leaflets of the valves closer to each other. For example, the annuloplasty devices move the posterior annulus of the mitral valve toward the anterior annulus of the mitral valve. Alternatively, the annuloplasty device can reshape the cross-sectional size of the mitral valve annulus. Reshaping includes at least one of reducing, reforming, or adjusting the mitral valve annulus in ways that cause the leaflets of the mitral valve to move closer to each other.

Reshaping may also include increasing the curvature (or reducing the radius along at least a portion of the curvature) of the coronary sinus that substantially encircles that mitral valve annulus thereby reshaping the mitral valve or the mitral valve annulus. Reshaping may also include decreasing the curvature (or increasing the radius along at least a portion of the curvature) of the coronary sinus in a way that exerts pressure on the mitral valve annulus or the mitral valve and flattening a portion or a side of the mitral valve annulus or the mitral valve.

The term coronary sinus can also includes the coronary vein or great cardiac vein as the name changes as one goes further up in the coronary sinus.

There are numerous different embodiments described below, which can perform at least one of these treatments. For example, a medical device that includes a first and a second anchoring member, in one embodiment, reshapes the mitral valve annulus from the first anchoring member to the second anchoring member due to the flexural properties (e.g., long term stiffness) of the device which causes the mitral valve annulus to be reshaped to conform to the shape of this medical device. In this embodiment, there is no tightening in the sense of a significant force applied along the longitudinal axis of the device, between the two anchoring members. This type of medical device may not require anchors attached to or included with the anchoring members (e.g., hooks, barbs, screws, corkscrews, helixes, coils, flanges, etc. . . . ) to hold the anchoring members in place.

In another embodiment, a medical device, which includes a first anchoring member, a second anchoring member, and a connection between the anchoring members, that reshapes the mitral valve annulus from anchoring member to anchoring member by the medical device being cinched (tightened) by a cord/cord and position-locking mechanism in the connection or having a fixed length cord or tube which connects the anchoring members and which is shorter than the existing (dilated) annulus. In this another embodiment, the medical device normally has a low or insignificant long-term flexural modulus (and thus it is moderately to highly flexible), and the medical device normally includes anchors such as hooks, barbs, or flanges, to name a few, to hold the anchoring members in place in order to resist the longitudinal cinching forces.

In yet another embodiment, a medical device includes a first anchoring member and a second anchoring member, which are coupled together by a connection, such as a telescoping assembly or a bellow-like member. The connection, of this yet another embodiment, reshapes the mitral valve annulus from anchoring member to anchoring member due to its flexural properties (e.g., long-term stiffness), and the medical device also reshapes the mitral valve annulus due to its being cinched (tightened) by a cord/cord and position-locking mechanism. Anchors may be used or otherwise included in the anchoring members of this yet another embodiment to ensure that the anchoring members remain in place. However, it may possible to balance the long-term stiffness and tightening so that the anchors are not required.

These different embodiments may be deployed percutaneously with a catheter device, which has a distal end having a preferred orientation (due to axial flexural modulus differences) in a curved conduit, such as the coronary sinus. The preferred orientation can be used to orient the medical device within the coronary sinus.

Figure 2A:
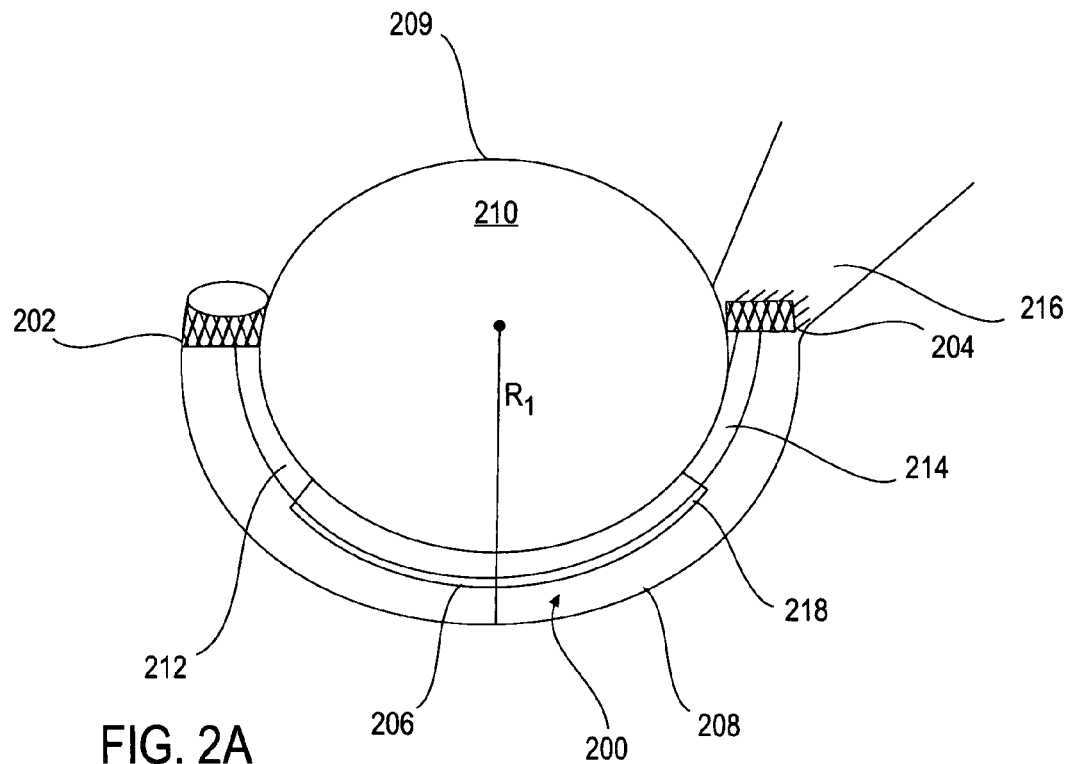
FIG. 2A is an illustration of an exemplary embodiment of an annuloplasty device deployed within a coronary sinus.

FIG. 2A illustrates one embodiment in which an annuloplasty device 200 is deployed within a coronary sinus (CS) 208, which substantially encircles or is adjacent to a mitral valve 210. Throughout the disclosure, the terminology "coronary sinus" covers not only the coronary sinus such as the CS 208 but also a proximate extension of the coronary sinus, (e.g., a near branch or flow that ends into the CS, the Great Cardiac Vein, or the Middle Cardiac Vein). An annuloplasty device includes at least a device that can reshape a blood vessel such as the CS 208, the mitral valve, and/or the mitral valve annulus. An annuloplasty device can also be deployed or delivered in, near, at, or within the CS 208 using methods such as percutaneous delivery or surgical installation.

Although the discussion below emphasizes on the deployment of the annuloplasty device 200 within the coronary sinus, the annuloplasty device 200 can be deployed within another blood vessel, vein, or artery to treat a different medical condition without departing from the scope of the present invention. Throughout the discussion, various exemplary embodiments of the annuloplasty device 200 can be understood to be deployable in the CS 208.

The annuloplasty device 200 includes a distal anchoring member 202, a proximal anchoring member 204, and a telescoping assembly 206 coupling to the distal anchoring member 202 and the proximal anchoring member 204. The annuloplasty device 200 can be percutaneously delivered and/or deployed (e.g., through a catheter) into the CS 208 through a blood vessel, a vein, or an artery, or alternatively, it may be delivered through a conventional surgical technique. The annuloplasty device 200 is capable of reshaping the CS 208 and/or reducing the mitral valve annulus or the mitral valve that has been enlarged or is otherwise not properly sealed.

Additionally, the annuloplasty device 200 is capable of reshaping a ventricle (e.g., the left ventricle) that has been enlarged due to a faulty valve (e.g., mitral valve regurgitation or MVR). In some cases, MVR causes the left ventricle to enlarge causing the papillary muscles (not shown) to move away from the mitral valve 210 and the chordae (not shown) attached between the papillary muscles and the leaflets (not shown) of the mitral valve 210.

This enlarged ventricle causes the mitral valve 210 to be held open (or referred to as "tethering"). The annuloplasty device 200 may reduce regurgitation by moving the posterior leaflet (not shown) nearer to the anterior leaflet (not shown) and prevents enlargement of the mitral valve 210.

The distal anchoring member 202 is configured to be deployed within the CS 208 as shown in FIG. 2A. Upon deployment, (or after deployment is complete) at least a portion of the distal anchoring member 202 anchors or attaches to the inner wall of the CS 208. Additionally, upon deployment, at least a portion of the distal anchoring member 202 may also penetrate the wall of the CS 208 and may anchor or attach to a cardiac tissue (or myocardial tissue) proximate the portion of the CS 208 where the distal anchoring member 202 is deployed. The distal anchoring member 202 may be deployed in the great cardiac vein, which is an extension or part of the CS 208. In one embodiment, at least a portion of the distal anchoring member 202 anchors or attaches to an area proximate the left trigone (not shown) adjacent the mitral valve 210 or to an annulus tissue. Portions of the distal anchoring member 202 may penetrate the wall of the CS 208 and anchor to the left trigone, the annulus tissue, or the area proximate the CS 208.

The proximal anchoring member 204 is configured to be disposed within or at the entrance 216 of the CS 208 as shown in FIG. 2A. The entrance 216 of the coronary sinus is the junction of the coronary sinus and the right atrium; in other words, this entrance is the point where deoxygenated blood from the heart enter the right atrium. At least a portion of the proximal anchoring member 204 anchors or attaches to a cardiac tissue proximate another portion of the CS 208 where the proximal anchoring member 204 is deployed. For example, at least a portion of the proximal anchoring member 204 anchors or attaches to an area at the entrance 216 of the CS 208. Alternatively, at least a portion of the proximal anchoring member 204 anchors or attaches to an annulus tissue or a myocardial tissue near the entrance 216 of the CS 208.

Figure 2B:
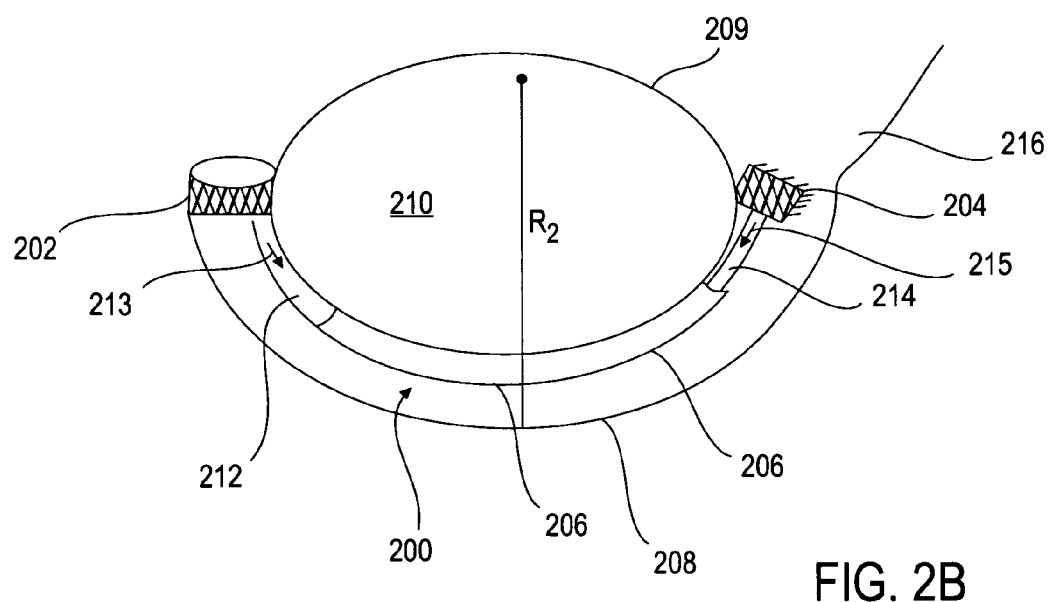
FIG. 2B is an illustration of how the annuloplasty device of FIG. 2A works to reduce the curvature of the coronary sinus and the mitral valve annulus.

The telescoping assembly 206 is deployable within the CS 208. The telescoping assembly 206 includes at least two members (e.g., tubes) wherein one is moveably (e.g., slidably) fitted within another. A telescoping assembly, in certain embodiments, is referred to as a member that includes at least two sections, such as two cylindrical tubes or sections that can slide/move inward and outward in an overlapping manner. In one embodiment, and as shown in FIG. 2A, the telescoping assembly 206 includes a distal tube 212, a center tube 218, and a proximal tube 214 wherein the distal tube 212 is coupled to the distal anchoring member 202 and the proximal tube 214 is coupled to the proximal anchoring member 204. The telescoping assembly 206 is able to reduce the distance between the distal anchoring member 202 and the proximal anchoring member 204 once the annuloplasty device 200 is fully deployed by bringing the distal tube 212 and the proximal tube 214 closer to each other (sometimes referred to as "telescoping"). For example, as shown in FIG. 2B, the distal tube 212 slides in the direction 213 into the center tube 218. Likewise, the proximal tube 214 slides in the direction 215 into the center tube 218. As the distal tube 212 and the proximal tube 214 slide into the center tube 218, the telescoping assembly 206 becomes shorter.

Reducing the distance between the distal anchoring member 202 and the proximal anchoring member 204 (after they are anchored in the coronary sinus) reduces or shortens portions of the CS 208. The annuloplasty device 200 thus is able to reshape at least a portion of the CS 208 thereby reshaping the cross-sectional size of the annulus 209 of the mitral valve 210 that is substantially encircled by the CS 208.

Typically, the CS 208 and the annulus 209 of the mitral valve 210 near the CS 208 are elastic in nature and are stretched by internal pressures generated by the heart. When the telescoping assembly 206 reduces/shortens the distance between the distal anchoring member 202 and the proximal anchoring member 204, some portions of the CS 208 and the annulus of the mitral valve 210 will be taken up as the pressure of the telescoping assembly 206 acts against the internal pressure and negates it. In some examples, the shortening of the CS 208 returns the tissue of the CS 208 to its "rest" dimension (which is smaller than its "enlarged" dimension caused by a faulty mitral valve or MVR). As the CS 208 shortens, the CS 208 applies pressure on the annulus 209 of the mitral valve 210 causing the posterior leaflet of the mitral valve 210 to be brought closer to the anterior leaflet effectively reducing or reshaping the cross-sectional size of the annulus 209. As the CS 208 shortens, the CS 208 flattens and the curvature of the CS 208 is reduced which causes the CS 208 to flatten portions of the annulus 209 of the mitral valve 210 as shown in FIG. 2B. Thus, the posterior leaflet of the mitral valve 210 is pushed toward the relatively fixed anterior leaflet. Since the posterior and anterior leaflets are moved closer together, the gap between them gets smaller or disappears and regurgitation is reduced or eliminated.

In one embodiment, reducing the distance between the distal anchoring member 202 and the proximal anchoring member 204 increases the curvature radius (or decrease the curvature) along at least a portion of the curvature of the mitral valve annulus 209 as shown in FIG. 2B. In FIG. 2A, the telescoping assembly 206 has been deployed but has not acted to reduce the distance between the distal anchoring member 202 and the proximal anchoring member 204; the CS 208 has a curvature radius $R_1$. In FIG. 2B, the telescoping assembly 206 reduced or shortened the distance between the distal anchoring member 202 and the proximal anchoring member 204; the CS 208 now has a curvature radius $R_2$, which is larger than the curvature radius $R_1$.

As can be seen, one reason for having the telescoping assembly 206 is that the telescoping assembly 206 may comprise of at least two members (e.g., the distal tube 212 and the proximal tube 214) wherein one smaller tube can slide into a larger tube. The telescoping assembly 206 can reduce the distance between the distal anchoring member 202 and the proximal anchoring member 204 with a telescoping action. Additionally, the telescoping assembly 206 can shorten a portion of the CS 208 thereby reshaping and reducing the curvature of the CS 208 and the annulus 209 of the mitral valve 210.

Figure 2C:
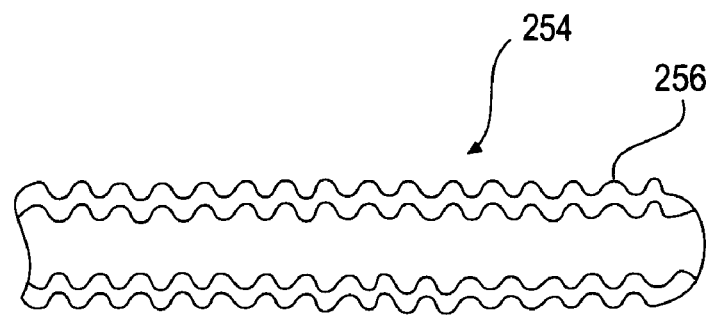
FIGS. 2C-2D are illustrations of another exemplary embodiment of an annuloplasty device.
Figure 2D:
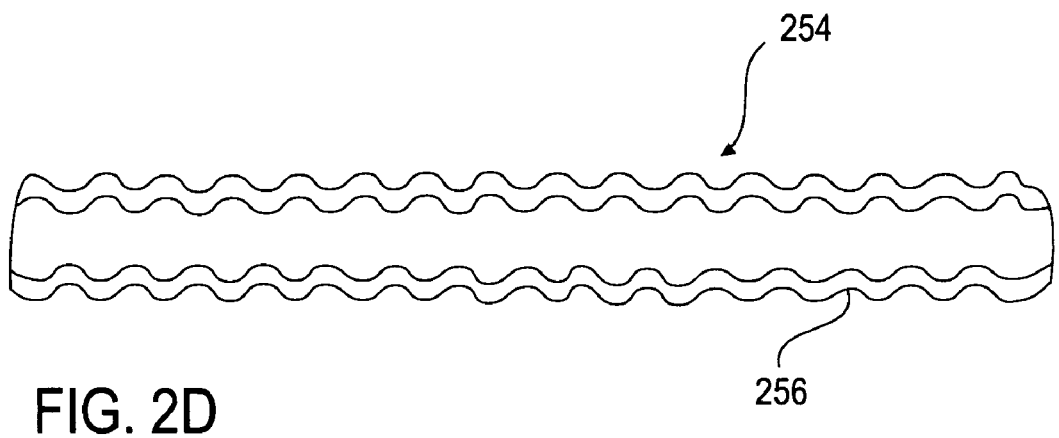

It will be appreciated that the telescoping assembly 206 is not the only structure that performs the functions mentioned above. In one embodiment, the telescoping assembly 206 is replaced by a bellow-like member 254 shown in FIGS. 2C-2D. In this embodiment, the bellow-like member 254 comprises a plurality of pleats 256, which allows that bellow-like member 254 to be compressed and extended. In one embodiment, the bellow-like member 254 is made of a shaped-memory material (e.g., Nitinol) such that during deployment, the bellow-like member 254 can be extended as shown in FIG. 2D. The bellow-like member 254 can also be made out of a polymer. The extended bellow-like member 254 allows the distal anchoring member 202 and the proximal anchoring member 204 to be deployed. Once deployment is complete, the bellow-like member 254 is allowed to return to its original shape (unextended) as shown in FIG. 2C. In one embodiment, the bellow-like member 254 is a tube having a bellow-like structure or wall. In one embodiment, a stiffening member (not shown) is disposed in the inner diameter or over the outer diameter of the bellow-like member 254 to increase flexural modulus for the bellow-like member 254.

FIGS. 3-10 illustrate various exemplary embodiments of a telescoping assembly that can be used for the telescoping assembly 206. FIGS. 11-18 illustrate various exemplary embodiments of the distal anchoring member that can be used for the distal anchoring member 202. FIGS. 19-22 illustrate various exemplary embodiments of the proximal anchoring member that can be used for the proximal anchoring member 204.

Figure 3A:
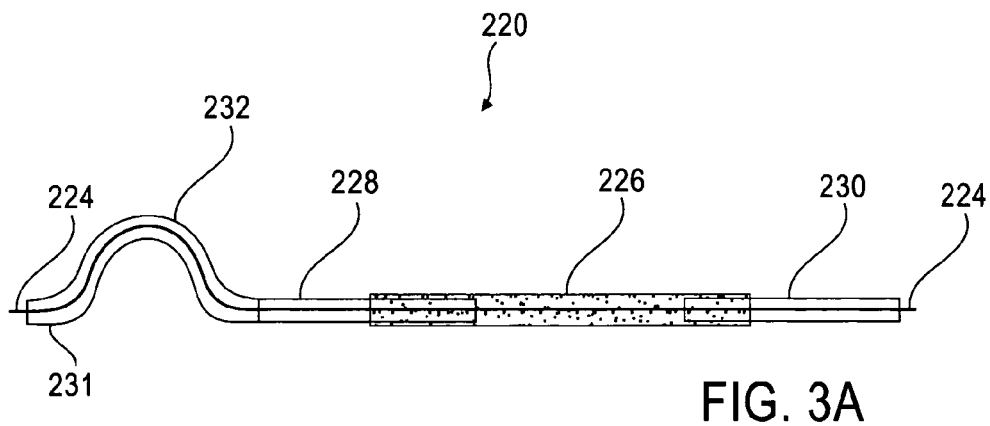
FIG. 3A is an illustration a telescoping assembly that can be used for an annuloplasty device in accordance with the embodiments of the present invention.

FIG. 3A illustrates an exemplary embodiment of a telescoping assembly 220 that can be used for the telescoping assembly 206 of the annuloplasty device 200 shown in FIGS. 2A-2B. The telescoping assembly 220 includes a distal tube 228, a center tube 226, and a proximal tube 230. It is to be understood that in alternative embodiments, only two tubes are necessary or more than three tubes can be used. In one embodiment, each of the distal tube 228, the center tube 226, and the proximal tube 230 is made of a flexible material. The distal tube 228, the center tube 226, and the proximal tube 230 are dimensioned such that the distal tube 228 is slidably fitted inside the center tube 226 from one end of the center tube 226 and the proximal tube 230 is slidably fitted inside the center tube 226 from the other end of the center tube 226. In one embodiment, the distal tube 228 and the proximal tube 230 can slide into the center tube 226. In an alternative embodiment, the center tube 226 may be slidably fitted inside the distal tube 228 or the proximal tube 230 or both. The center tube 226 thus slides into the distal tube 228, the proximal tube 230, or both.

Each of the distal tube 228, the center tube 226, and the proximal tube 230 may have any suitable cross-sectional shape. For example, the tubes may be circular, oval, or rectangular in cross-section. The chosen shape should be one that provides that most surface area for the telescoping assembly 220 to be deployed against the wall of the CS 208 without a substantial blockage of the flow (to prevent stenosis and clotting) within the CS 208.

The distal tube 228 further includes a bent portion such as a U-shaped portion 232 that is relatively stiff. The U-shaped portion 232 is useful when the annuloplasty device 200 needs to be positioned over an area that has other artery or blood vessel crossing below. In one embodiment, the U-shaped portion 232 is useful when the annuloplasty device 200 needs to be placed over the circumflex coronary artery. The U-shaped portion 232 allows the annuloplasty device to avoid compressing the circumflex coronary artery when the annuloplasty device 200 is in position and fully deployed. In one embodiment, the U-shaped portion 232 is made of a flexible material. Other bent portions having other shapes (e.g., an S-shape or a V-shape) may be used instead of the U-shaped.

In one embodiment, the U-shaped portion 232 may include a telescoping feature similar to the telescoping assembly 220. Thus, the U-shaped portion 232 itself may include at least two members or tubes that can slide inward or outward into each other.

In one embodiment, at least one cord 224 is disposed through the inner diameters of the telescoping assembly 220. The cord 224 functions to adjust the length of the telescoping assembly 220. In one embodiment, the cord 224 couples to the distal end portion 231 of the U-shaped portion 232 and extending from the U-shaped portion 232 through the proximal tube 230. The cord 224 could also be coupled to any portion of the distal tube 225 or any portion of the telescoping assembly 220. The distal end of the cord 224 may also attach to or engage with a distal anchoring device (not shown) such as the distal anchoring member 202 shown in FIG. 2A. The proximal end of the cord 224 attaches to or engages with a proximal anchoring device (not shown) such as the proximal anchoring member 204 shown in FIG. 2B. When the cord 224 is pulled proximally relative to the proximal tube 230 (or the proximal anchoring member), the cord 224 is placed in tension, causing the distal tube 228 and the proximal tube 230 to move closer together and telescope into the center tube 226. Alternatively, when the cord 224 is pulled distally relative to the distal tube 228 (or the U-shaped portion 232), the cord 224 is placed in tension, causing the distal tube 228 and the proximal tube 230 to move closer together and telescope into the center tube 226.

The cord 224 can be made of metal, metal alloy, NiTi, Nitinol, and etc. The cord 224 can be made of an elastic material such as silicone/silastic, nitrile, polyurethane, neoprene, and fluorosilicone, and etc. The cord 224 can be made out of or coated with a low friction material, like a fluorocarbon, Acetal, PE, or Nylon. The cord 224 may have any suitable cross-sectional shape, rectangular, circular, oval, etc.

In one embodiment, the distal tube 228, the proximal tube 230 and the center tube 226 contain mechanical interferences such that the distal tube 228 will not disengage from the inner diameter of the center tube 226 and the proximal tube 230 will not disengage from the inner diameter of the center tube 226. Examples of suitable mechanical interferences include o-rings, lips, flanges pins, projections, or slots created into or attached to the tubes.

Figure 3B:
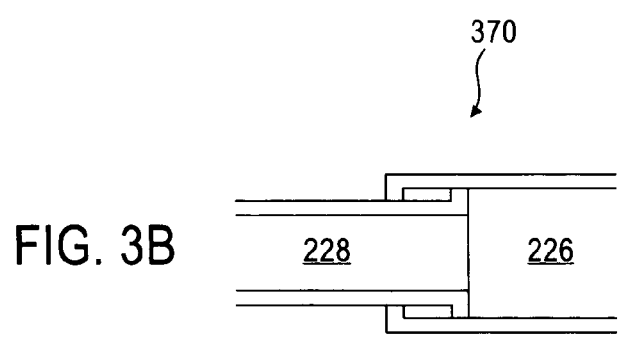
FIGS. 3B-3C are illustrations of exemplary embodiments of mechanical interferences that can be used for an annuloplasty device in accordance with the present invention.

In one embodiment, a suitable mechanical interference includes a flange/lip type interference 370 as shown in FIG. 3B. In this embodiment, the distal tube 228 includes lips/flanges 372 and the center tube 226 includes lips/flanges 374. The lips/flanges 372 and 374 engage each other to prevent disengagement as the distal tube 228 and the center tube 226 slide into and away from each other. The same interference 370 can be used to apply to other tubes of the telescoping assembly 220, for example, the proximal tube 230 could also include the same interference 370.

Figure 3C:
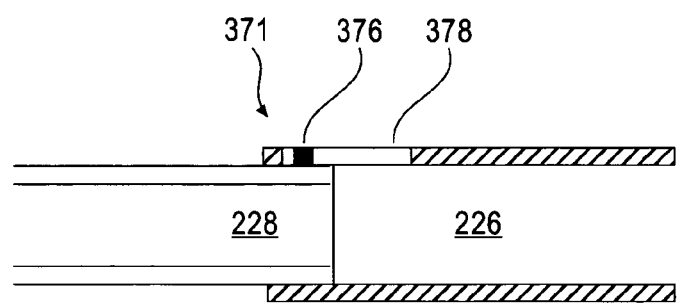

In one embodiment, a suitable mechanical interference includes a pin/projection type interference 371 as shown in FIG. 3C. In this embodiment, the distal tube 228 includes at least one pin/projection 376, which engages at least one slot 378 created into the center tube 226 to prevent the distal tube 223 from disengaging the proximal tube 226. The same interference 371 can be used to apply to other tubes of the telescoping assembly 220, for example, the proximal tube 230 could also include the same interference 370.

In one embodiment, the distal tube 228 (including the U-shaped portion 232), the proximal tube 230 and the center tube 226 are made of a low friction material, like a fluorocarbon, Acetal, PE or Nylon to limit the friction (for example, to make the telescoping action easier).

In another embodiment, to prevent disengagement of the tubes of the telescoping assembly 220, an extension-limiting cord (not shown) is disposed within or through the inner diameters of each of the distal tube 228, the proximal tube 230, and the center tube 226. The extension-limiting cord is attached between adjacent tubes. For example, one portion of the extension-limiting cord is attached to both the distal tube 228 and the center tube 226 and another portion of the extension-limiting cord is attached to both the proximal tube 230 and the center tube 226. The extension-limiting cord can be divided into two extension-limiting cords wherein one extension-limiting cord is attached to the distal tube 228 and the center tube 226 at each end of the cord; and, the other extension-limiting cord is attached to the proximal tube 230 and the center tube 226 at each end of the cord. The length of the extension-limiting cord(s) is fixed such that if one adjacent tube is moved away from another adjacent tube, the extension-limiting cord dictates the maximum length or distance that the tubes can move away from each other. The extension-limiting cord(s) has a length that prevents the distal anchoring member and the proximal anchoring member from disengaging with the center tube 226. The extension-limiting cord may be made out of a thin and flexible material such as nylon, Vectran® (Vectran® is a registered trademark of Hoechst Celanese and is manufactured by companies such as Dupont and Allied Signal), Kevlar® (Kevlar® is a registered trademark of Dupont and is manufactured by Dupont), or other suitable materials. One advantage of using the extension-limiting cord is that the various tubes of the telescoping assembly 220 can have smaller inner diameters which overall, allows for smaller annuloplasty devices.

In one embodiment, the distal tube 228 and the proximal tube 230 are biased to be a predetermined distance (a minimum distance) away from each other during delivery/deployment. A compression spring(s) (not shown) may be placed inside the inner diameter of the center tube 226 to bias the ends of the distal tube 228 and the proximal tube 230. During delivery/deployment, the compression springs keep the distal tube 228 and the proximal tube 230 apart. In some embodiments, the compression springs keep the distal anchoring member 228 and the proximal anchoring member 230 from disengaging from the center tube 226. Additionally, in some embodiments, the compressions springs may act to keep the distal tube 228 engaging to a least a portion of the distal anchoring member (not shown) and the proximal tube 230 engaging to at least a portion of the proximal anchoring member (not shown).

In one embodiment, the telescoping assembly 220 has differential stiffness along the various sections and tubes of the telescoping assembly 220. One advantage for the differential stiffness is that it allows the annuloplasty device to have orientation, curve, and shape that make reshaping the mitral valve annulus 209 easier. A section that has a high stiffness is sometimes referred to as having a high flexural modulus. A section that has a low stiffness is sometimes referred to as having a low flexural modulus. Each of the distal tube 228, the proximal tube 230, and the center tube 226 may have variable flexural modulus. The flexural modulus of various tubes of the telescoping assembly 220 has a pronounced effect on the amount of tension or force that is required to be applied to the cord 224 to adjust the length and/or curvature of the mitral valve annulus 209. For instance, very low flexural modulus (low stiffness) tubes makes device delivery easier, but will require a higher tension be applied to the cord 224 to reform the mitral annulus such that the leaflets will coaptate (or close) reliably and eliminate mitral valve regurgitation. Very high modulus (high stiffness) tubes makes device delivery difficult, but will require a much lower tension to be applied to the cord 224 to reform the mitral annulus such that the leaflets will coaptate (or close) reliably and eliminate mitral valve regurgitation.

In one embodiment, the flexural modulus is optimized such that delivery of the annuloplasty device that contains the telescoping assembly 220 is relatively or sufficiently easy while not too high of a tension is needed to change the length of the telescoping assembly 220. In one embodiment, the distal tube 228, the center tube 226, and the proximal tube 230 are made of low flexural modulus materials. The sections that the distal tube 228 and the center tube 226 overlap are maximized. Likewise, the sections that the proximal tube 230 and the center tube 226 overlap are also maximized. When the annuloplasty device is being deployed or delivered, the distal tube 228, the center tube 226, and the proximal tube 230 are at the farthest extension, which gives the telescoping assembly 220 an overall low flexural modulus characteristic, which eases the delivery/deployment process. Once fully deployed, the distal tube 228 and the proximal tube 230 are telescoped together (or retracted) into the center tube 226 as close as possible to give the telescoping assembly 220 the most overlapping sections and to also shorten the length of the telescoping assembly 220. The telescoping assembly 220 thus will have a high flexural modulus characteristic. Thus, a lower tension is required to be exerted on the cord 224, which is used to reshape the mitral valve annulus 209.

In one embodiment, each of the distal tube 228, the center tube 226, and the proximal tube 230 itself has sections with variable flexural modulus or stiffness. The variable flexural modulus in each of the tubes further enhances the ease of adjusting, reducing, reforming, or reshaping the mitral valve annulus 209. Methods to provide differential or variable modulus to a structure are well known in the art.

Figure 4:
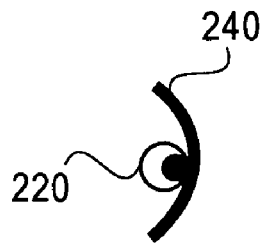
FIGS. 4-6 illustrate exemplary embodiments of force distribution members that can be used for an annuloplasty device in accordance with the embodiments of the present invention.
Figure 5:
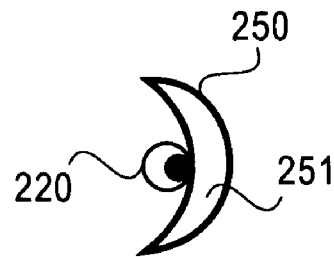
Figure 6:
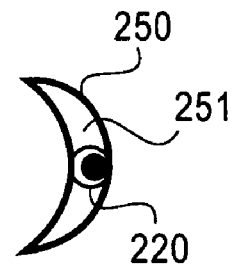

In one embodiment, the telescoping assembly 220 includes at least one force distribution member. FIGS. 4-6 illustrate cross-sectional views of exemplary configurations of force distribution members 240 and 250, which can be incorporated into the telescoping assembly 220. As shown in FIG. 4, in one embodiment, a portion of the force distribution member 240 is coupled to the side of the telescoping assembly 220 that contacts the blood vessel (e.g., the CS 208). The force distribution member 240 may be a solid structure as shown in FIG. 4 or may include a lumen 251 as shown in the force distribution member 250 of FIGS. 5-6. The telescoping assembly 220 may be placed outside of the lumen 251 as shown in FIG. 5 or inside of the lumen 251 as shown in FIG. 6.

The force distribution members 240 and 250 allow the use of a minimum sized circular cross-section for the telescoping assembly 220. A minimum size cross-section for the telescoping assembly 220 causes less interference with the flow or the blood flow in the blood vessel. Without the force distribution members, the outer diameter of the telescoping assembly 220 needs to be larger so as to not allow the force or tension of the cord 224 to cut through the blood vessel that the annuloplasty device is deployed within. The force distribution members provide a large surface area to distribute the force exerted on the blood vessel by the telescoping assembly 220 and/or the cord 224 over the blood vessel wall (or the wall of the CS 208) preventing damage to the blood vessel wall that may be caused by a high and/or focused force applied on the wall.

In one embodiment, the force distribution members 240 and 250 may include support members (such as a stiffening skeleton, struts, braid(s), flattened coil(s), etc.) as a part of their structure and/or be made of a variable thickness and/or width materials to facilitate the more even distribution of the force over the surface of the vein, as is well know to those skilled in the art. The force distribution members may have variable flexural modulus along each force distribution member or among one another. The force distribution members may also have variable dimensions (e.g., lengths and widths). Each of the force distribution members may be made of different material or design type.

Figure 7:
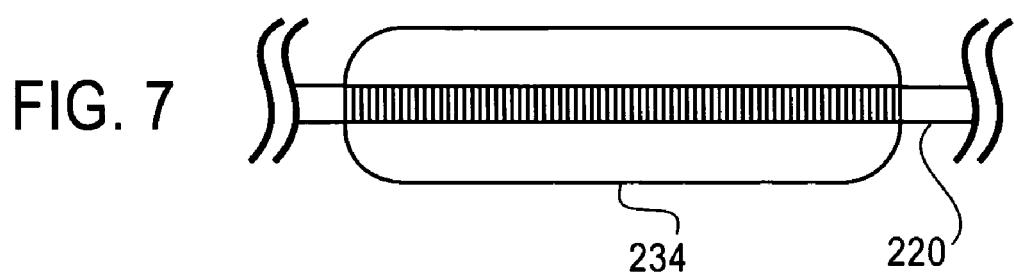
FIGS. 7-10 illustrate other exemplary embodiments of force distribution members that can be used for annuloplasty devices in accordance with the embodiments of the present invention.
Figure 8:
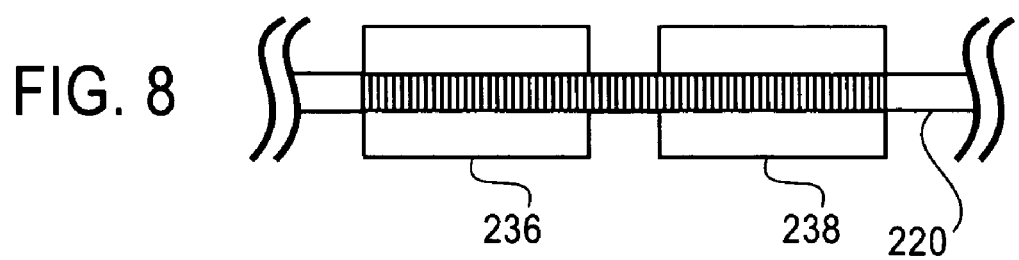
Figure 9:
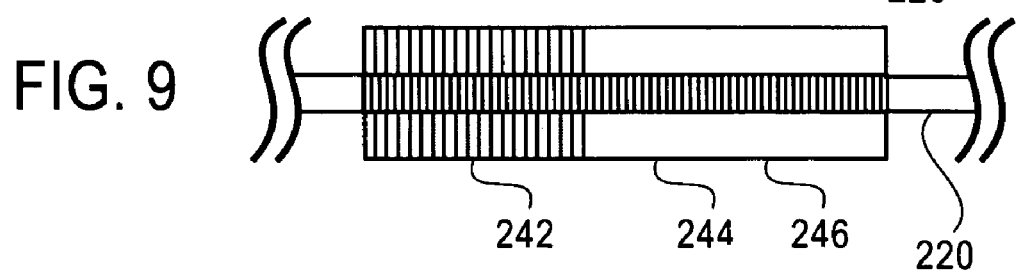
Figure 10:
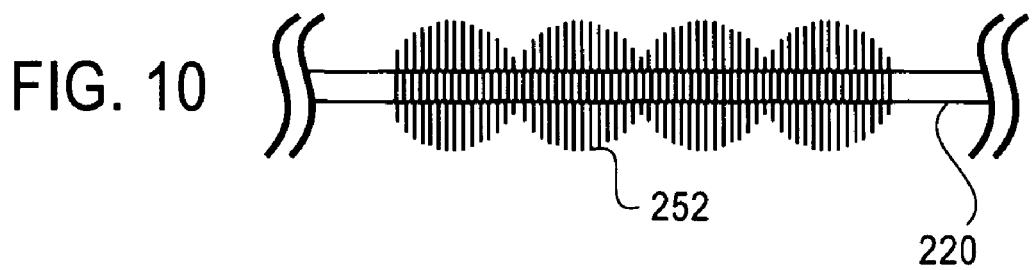

If desired, a force distribution member may cover a large section or the entire telescoping assembly 220. In one embodiment, at least a portion of the telescoping assembly 220 is covered by a large force distribution member 234 as shown in FIG. 7. Alternatively, various portions along the telescoping assembly 220 are covered by several force distribution members 236 and 238 as shown in FIG. 8. The force distribution members 236 and 238 may cover portions or the entire telescoping assembly 220 with gaps between each distribution member. Alternatively, the telescoping assembly 220 may be covered with several force distribution members 242, 244, and 246 with sections of force distribution members overlapping one another. Additionally, when the distribution members contain lumens, one distribution member may slide into another distribution member (as shown in FIG. 9) in the same manner that the various tubes of the telescoping assembly slide into one another. Adjacent force distribution members 242, 244, or 246 may slide over or inside one another. The force distribution members may have an oblong shape as shown in FIG. 7, a rectangular shape as shown in FIGS. 8-9, or a circular shape as shown in FIG. 10.

In one embodiment, the force distribution members (e.g., the force distribution members 240, 250, 234, 236, 238, 242, and 244) may have projections or anchors (not shown). These projections or the anchors may engage adjacent force distribution members and function to control or adjust the length of the telescoping assembly 220. For instance, when the telescoping assembly 220 is replaced by the bellow-like member 254 as shown in FIGS. 2C-2D, the force distribution members control the extension of the bellow-like tube 254 to a predetermined length. The projections or anchors may also aid (or even replace) the various tubes of the telescoping assembly 220 when necessary. For example, the force distribution members with anchors may allow replacing the telescoping assembly 220 with a single member/tube with no telescoping capability. These projections or anchors may face the wall of the blood vessel and may provide engagement with the blood vessel wall in a manner that causes length changes to be directed to a desired portion of the blood vessel wall. The projections or anchors may aid in the anchoring of the annuloplasty device that contains the telescoping assembly 220. The projections or anchors may also aid in the anchoring of the distal anchoring member 202 and the proximal anchoring member 204.

FIGS. 11-18 illustrate exemplary embodiments of a distal anchoring member that can be used for the distal anchoring member 202 shown in FIGS. 2A-2B. The distal anchoring members described below can be deployed into the CS 208. The distal anchoring members may be deployed percutaneously using conventional delivery device or a delivery device that will be described below (e.g., FIGS. 23, 25, and 26).

FIG. 11 illustrates a side view of an exemplary distal anchoring member 302. The distal anchoring member 302 may have conventional stent designs or configurations typically used for cardiac related treatment such as angioplasty or carotid stenting. Thus, the distal anchoring member 32 may resemble a tube like cylinder which is hollow. An example of such a stent includes an AccuLink™ self-expending stent made by Guidant Corporation). The distal anchoring member 302 is expandable and may or may not be self-expandable.

In one embodiment, the distal anchoring member 302 is self-expandable and may be made of a shaped-memory material such that upon deployment, the distal anchoring member 302 returns or expands back to its original shape and size as allowed by the blood vessel that it is placed in (e.g., the CS 208). Examples of a shaped-memory material suitable for the distal anchoring member 302 include Nitinol or other material that has a memory of their original shapes. In one embodiment, the distal anchoring member 302 is made of a superelastic material such as Nickel Titanium alloys, CuZnAl alloys, CuAlNi alloys, FeMnSi alloys, InTi alloy, MnCu alloys, AgCd alloys, AuCd alloys, etc.

Alternatively, the distal anchoring member 302 may be expanded by mechanisms well known in the art, for example, by an inflatable or dilatable balloon. The distal anchoring member 302 is sized to fit within the blood vessel that it is being deployed within. In one embodiment, the distal anchoring member 302 is sized to fit within a coronary sinus or a great cardiac vein, such as the CS 208 shown in FIGS. 2A-2B. In one embodiment, once fully deployed within the CS 208, the distal anchoring member 302 is deployed against the inner wall of the CS 208. In one embodiment, the distal anchoring member 302 is deployed such that its outer wall (outer diameter) presses against the inner wall (inner diameter) of the CS 208.

FIG. 12 illustrates a side view of an exemplary distal anchoring member 402. The distal anchoring member 402 is similar to the distal anchoring member 302 shown in FIG. 11 except that the distal anchoring member 402 includes a plurality of projections or anchors 403. The anchors 403 may be configured to shape like helixes, coils, hooks, barbs, corkscrews, screws, flanges, or any other suitable anchoring device. The anchors 403 are designed to penetrate the wall of the CS 208 and attach or anchor to a cardiac tissue proximate the CS 208. In one embodiment, the anchors 403 penetrate the wall of the CS 208 and anchor into the left trigone proximate the CS 208. The anchors 403 thus provide additional support for the distal anchoring member 402 to allow a secure deployment of the distal anchoring member 402 within the CS 208 at a particular location along the CS 208. The anchors 403 may have shape or arcs that are suitable for definitive anchoring of the distal anchoring member 402.

FIG. 13 illustrates a side view of an exemplary distal anchoring member 502 which is similar to the distal anchoring member 402 except that a plurality of projections or anchors 503 are distributed over the outer diameter of the distal anchoring member 502. The anchors 503 can be the same as the anchors 403 described above. The addition of more anchors improves the anchoring capability of the distal anchoring member 502. The anchors 503 may be distributed over the outer diameter of the distal anchoring member 502 in any convenient manner, location, and number.

FIG. 14 illustrates a side view of an exemplary distal anchoring member 602, which is similar to the distal anchoring member 402 except that the anchors have barbed shapes, as illustrated by anchors 603. Additionally, the anchors 603 are also distributed along one side of the distal anchoring member 602. In some applications, the distal anchoring member needs to be anchored only on one side. For example, when the distal anchoring member 602 is deployed within the CS 208, the distal anchoring member 602 needs to penetrate only one side of the CS 208 to be anchored to an area in the left trigone, an area proximate the CS 208, or in the annulus tissue of the mitral valve 210 that is adjacent the CS 208. Thus, it is only necessary to distribute the anchors 603 only on the side of the distal anchoring member 602 that will be the anchoring side.

FIGS. 15A-15B illustrate sectional views of an exemplary distal anchoring member 702. FIG. 15A is a side view and FIG. 15B is a cross-sectional view. The distal anchoring member 702 is similar to the distal anchoring member 602. The distal anchoring member 702 includes a plurality of projections or anchors 703 distributed and oriented toward one side of the distal anchoring member 702. In one embodiment, the anchor support relies on the anchors 703 that penetrate the cardiac tissue, the annulus tissue, or the left trigone through the wall of the CS 208. The anchors 703 may be required only on one side of the distal anchoring member 702. In one embodiment, a proper orientation may be necessary such that the anchors 703 are oriented toward the anchoring site. This will required that the distal anchoring member 702 be properly oriented within the coronary sinus.

In one embodiment, the distal anchoring member 702 is composed of differential stiffness (variable flexural modulus). The side 705 of the distal anchoring member 702 that does not include any anchors 703 is made stiffer than the side 707 of the distal anchoring member 702 that includes the anchors 703. In one embodiment the distal anchoring member 702 is deployed within the CS 208, which curves around the mitral valve 210 shown in FIGS. 2A-2B. The distal anchoring member 702 also curves during and after its deployment within the CS 208. The lowest storage energy state of the distal anchoring member 702 is with the stiffer side 705 toward the outside of a curved CS 208. In other orientations of higher energy storage, the produced energy gradient tends to twist the distal anchoring member 702 and the delivery device/catheter used to deliver the distal anchoring member 702 toward the lowest energy state which directs the distal anchoring member 702 toward the desired anchoring site/orientation (e.g., the mitral valves annulus tissue, the myocardium, and the left trigone) and away from the free wall of the CS 208 or other less desirable anchor orientations. In one embodiment, the variable flexural modulus of the distal anchoring member 702 is provided by adding more material and/or a pattern on the side 705 than the side 707 such that the side 705 has a higher flexural modulus. Suitable patterns that will provide a higher flexural modulus to the distal anchoring member 702 are well known and understood by those skilled in the art.

In one embodiment, the distal anchoring member 702 is deployed within the CS 208 using a delivery catheter. At least a portion of the delivery catheter's distal end, proximate to the distal anchoring member 702 has a higher flexural modulus on one side than the other. Thus, when the delivery catheter is inserted into a curved CS 208, its lowest energy storage state will be with the higher flexural modulus side toward the outside of the blood vessel's curve. In other orientations of higher energy storage, the produced energy gradient tends to twist the delivery device toward the orientation of the lowest energy state. The orientation for the distal anchoring member 702 is controlled by the orientation of the delivery catheter. Thus, mounting the distal anchoring member 702 in or on the delivery catheter in a controlled orientation relative to the delivery catheter's higher flexural modulus side directs the distal anchoring member (as previously described) or other features of the distal anchoring member 702 toward the desired anchoring site/orientation (e.g., the mitral valves annulus tissue, the myocardium, and the left trigone) and away from the free wall of the CS 208 or other less desirable anchor orientations.

FIGS. 16A-16D illustrates a cross section of a distal anchoring member 802 that comprise of an outer part 805 and an inner part 822. It is to be appreciated that the configuration of the distal anchoring member 802 can be applied to other anchoring members that include at least one projection or anchor. The outer part 805 can be a protective sheath that is disposed outside of the inner part 822 that has a plurality of anchors 803. Alternatively, the outer part 805 can be the distal anchoring member itself while the inner part 822 is the structure that includes the anchors 803. In one embodiment, the outer part 805 is a stent-like device that is expandable and/or self-expandable. The outer part 805 includes a plurality of openings (e.g., holes or slots) 812 cut into it. During deployment, the outer part 805 keeps the anchors 803 in a non-deployed position (non-projecting or non-anchoring position). The outer part 805 prevents the anchors 803 from damaging the wall of the blood vessel as the distal anchoring member 802 is being deployed. When the distal anchoring member 802 is being deployed, the anchors 803 are contained/constrained by the outer part 805. Once the distal anchoring member 802 reaches the proper location for deployment and anchoring, the outer part 805 is slightly moved away from the inner part 822 such that the end of the anchors 803 engage or can be made to engage the openings 812. Once the anchors 803 pass through the openings 812, the anchors 803 project out and penetrate the wall of the blood vessel and anchor themselves into a myocardium tissue proximate the blood vessel (e.g., the left trigone or the mitral valve annulus tissue). After deployment, the anchors 803 anchor the distal anchoring member 802 into the blood vessel.

Figure 17:
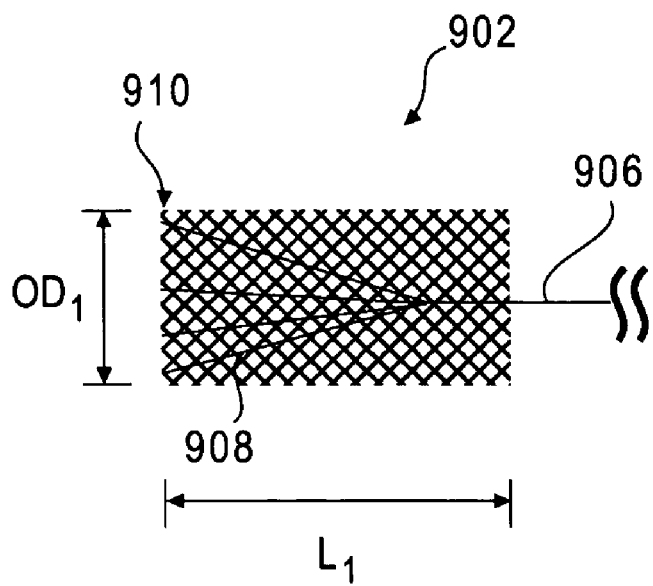
Figure 18:
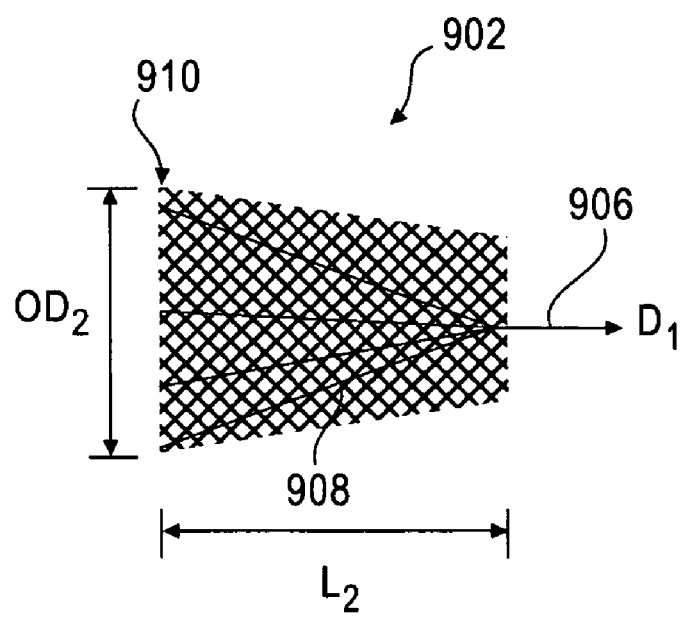

FIGS. 17-18 illustrate a sectional view of a distal anchoring member 902. The distal anchoring member 902 is similar to those distal anchoring members described above with an addition of a tension cord 906 attaching to the distal anchoring member 902. The tension cord 906 may include a plurality of branches 908 each of which is attached to a point at the distal end 910 of the distal anchoring member 902. In one embodiment, the tension cord 906 extends along the distal anchoring member 902 and through the telescoping assembly (not shown) that is coupled to the distal anchoring member 902. The tension cord 906 can also act as the cord 224 to telescope the various tubes of the telescoping assembly such as the telescoping assembly 220 while exerting compression forces on the distal anchoring member 902.

In one embodiment, the distal anchoring member 902 is configured so that a compression force caused by the tension cord 906 expands the outer diameter of the distal anchoring member 902. For example, when the tension cord 906 is pulled in the direction $D_1$, the outer diameter of the distal anchoring member 902 increases from the $OD_1$ to $OD_2$ wherein $OD_2>OD_1$. Enlargement of the outer diameter helps ensure that the distal anchoring member 902 is securely deployed against the inner diameter of the CS 208. When tension is applied to the tension cord 906 proximally, the length of the distal anchoring member 902 is decreased from length $L_1$ to length $L_2$. In one embodiment, the tension cord 906 is the same as the cord 224 used to adjust the length of the telescoping assembly 220 described above. The tension longitudinally compresses the distal anchoring member 902 to the shorter length $L_2$ thereby making the outer diameter of the distal anchoring member 902 larger. The tension cord 906 ensures an increased pressure of the distal anchoring member 902 against the blood vessel. This increased pressure causes the distal anchoring member 902 positioned in the blood vessel to be better retained at its deployment location. The configuration of the distal anchoring member 902 is especially useful when the distal anchoring member does not include a projection or an anchor. Although not shown, the distal anchoring member 902 may also include anchors (e.g., hooks, barbs, or screws) for better attachment.

In one embodiment, any of the distal anchoring members described may incorporate materials/coatings/drugs that encourage their attachment or biological incorporation into the cardiac tissue to prevent displacement of the distal anchoring members. Additionally, any of the distal anchoring members described may incorporate coatings/materials/drugs that help keep the inner diameter of the CS 208 clear and open.

FIGS. 19-23 illustrate sectional views of exemplary embodiments of a proximal anchoring member that can be used for the proximal anchoring member 204 shown in FIGS. 2A-2B. It will be appreciated that the proximal anchoring member may have the configurations of any of the distal anchoring members previously described as alternatives to the configurations in FIGS. 19-23 described below.

FIGS. 19A-19B illustrate an exemplary proximal anchoring member 304. FIG. 19A is a side view of a proximal anchoring member, and FIG. 19B is a view from the distal end of the proximal anchoring member. The dimensions and shapes of the proximal anchoring member 304 may be varied and corners/sharp edges may be blended or radiused as necessary. In one embodiment, the proximal anchoring member 304 comprises a distal portion 308 and a flange portion 306. In one embodiment, the proximal anchoring member 304 is deployed in the entrance 216 to the CS 208 (shown in FIGS. 2A-2B). The distal portion 308 is deployed inside the CS 208 and the flange portion 306 is deployed outside the CS 208 (e.g., near the junction of the CS 208 and the right atrium) such that it prevents the proximal anchoring member 304 from being displaced distally within the CS 208 as a result of forces applied to the proximal anchoring member 304 by the telescoping assembly such as the telescoping assembly 206 shown in FIGS. 2A-2B or the telescoping assembly 220 shown in FIG. 3A. In some embodiments, the distal portion 308 may be very short or omitted entirely, but this is not recommended, as the danger of blocking flow from the CS 208 may be increased. The distal portion 308 may be made similar to the distal anchoring members previously described. The distal portion 308 may include anchors (not shown) such that upon deployment, the anchors attach to the wall of the CS 208. The distal portion 308 is expandable or self-expandable similar to the distal anchoring member previously described. The distal portion 308 is sized so that its outer diameter engages the inner diameter of the CS 208 in order to prevent blocking to a venous flow path. The distal portion 308 may incorporate drugs, coatings, or materials that help keep the entrance to the CS clear and open.

In one embodiment, the flange portion 306 engages the right atrium (RA) wall (not shown). In one embodiment, the flange portion 306 is circular (but need not be circular) as shown in FIG. 19A. The flange portion 306 may have its shape modified to avoid interference with the function of the Tricuspid valve (not shown) or to concentrate support to the regions of the right atrium that is in closer proximity to the right trigone (not shown). The flange portion 306 is expandable or self-expandable. The flange portion 306 may incorporate features (e.g., anchors, hooks, barbs, or screws, etc.), materials, coatings, or drugs that encourage its attachment or biologic incorporation into the right atrium wall. The flange portion 306 may also be made of a porous material, a reinforced porous material, coated with a porous material and/or drug coated to encourage its incorporation into the right atrium wall. In one embodiment, the flange portion 306 is collapsible such that during deployment, the flange portion is folded to fit within the delivery device and after deployment, the flange portion 306 expands to engage and remain at or just proximal to the entrance of the CS 208. In one embodiment, the flange portion 306 may be discontinuous and/or formed to appear as two or more separate arms or bands.

In one embodiment, as shown in FIG. 20, the flange portion 306 may be formed of a plurality of arms 408 that upon deployment, the arms 408 spring out to form a globe-like structure that prevents the proximal anchoring member 304 from being displaced distally within the CS 208 as a result of forces applied to the proximal anchoring member 304 by the telescoping assembly such as the telescoping assembly 206 shown in FIGS. 2A-2B or the telescoping assembly 220 shown in FIG. 3A. The arms 408 may have the shapes of curved bands. The multiple curved bands are joined to each other at two points or to two rings 410 and 412 to form the globe-like structure that is sufficiently large so as to not be able to enter the CS 208. The ring 410 may replace the distal portion 308 of the proximal anchoring member 304 or may be attached to the distal portion 308 (not shown here).

The number of the arms 408 may be any desired number, but a number greater than 2 provides the most stable form for the flange portion 306. The arms 408 may have a rest shape (or a natural shape) that is curved. This curve need not be circular as shown in FIG. 20, but may have some curve that is convenient for the control of the collapsing and the expansion of the flange portion 306. The curve orientation of the arms 408 may be as shown in FIG. 20 in which the arms 408 have concave sides toward one another. The curve orientation of the arms 408 may have other forms, for example, convex forms or the combination of convex and concave forms.

In one embodiment, the arms 408 have spiral forms (not shown). In this configuration, when the arms 408 are confined inside a tube (for delivery), the arms 304 form a spring-like configuration that is very flexible. The spiraled arms 408 also increase the ease of delivery.

FIG. 21A-21D illustrate an exemplary embodiment of a proximal anchoring member 309 that includes a plurality of anchors, anchors 503 and anchors 501. In one embodiment, the proximal anchoring member 309 resides upon the right atrium wall and near or at the right trigone. The anchors 501 and 503 enable the proximal anchoring member 309 to penetrate the right atrium and engage the right trigone or the area near the right trigone. The anchors 501 and 503 also enable a flange portion 346 of the proximal anchoring member 309 to anchor to the entrance of the CS 208. The anchors may be helixes, coils, hooks, barbs, screws, rivets, flanges, or corkscrews as some are shown in FIGS. 21A-21D.

The proximal anchoring member 309 also includes telescoping members 347 and 348, which can slide into each other, or telescope together as shown in FIGS. 21A-21B where the telescoping member 347 slides into the telescoping member 348. The telescoping members 347 and 348 function much like the telescoping assembly 220 previously described. The anchors 501 are attached to the telescoping member 347 and are biased by their rest configuration (curvature) and/or the manner in which their ends are sharpened. The anchors 501 are curved at rest and are constrained within the inner diameter of the telescoping member 348, such that they begin their deployment in a relatively straighter or less curved condition. The telescoping member 347 contains a mechanical interference 349 that engages with the telescoping member 348 (much similar to previously described) such that the deployment of the anchors 501 is limited to a predetermined length (telescoping length) and that the telescoping member 347 will not disengage from the telescoping member 348. When deployed, the anchors 501 penetrate or attach to the right trigone.

The telescoping section 348 is attached to a flange 346. The flange 346 contains an opening (not shown) to allow the anchors 501 to pass through for deployment. The flange 346 includes the anchors 503 on the side of the flange 346 that contacts the right atrium. The flange 346 distributes the forces applied to proximal anchoring member 309 over an area of the right atrium during the deployment of the anchors 503. The flange 346 may be configured to have a wide variety of shapes (oval or flat). The flange 346 may have a shape that facilitates the delivery of the proximal anchoring member 309 to the right atrium wall. The flange 346 may be made of a porous material, a reinforced porous material, coated with a porous material and/or drug coated to encourage its incorporation into the right atrium wall.

Additionally, the anchors 501 and the anchors 503 may be made of or coated with a porous material and/or drugs to encourage their incorporation into adjacent tissue. Further yet, the proximal anchoring member 309 may include radiopaque marker(s) in any of its portion to aid in the delivery visualization and in orienting of the proximal anchoring member 309 such that the anchors 503 and 501 point toward the side of the CS 208 that faces the mitral valve annulus 209.

The proximal anchoring member 309 can be used as the proximal anchoring member 204 of the annuloplasty device 200. The proximal anchor member 204 may be attached or coupled to the telescoping assembly 220 previously described.

Figures 22A, 22B:
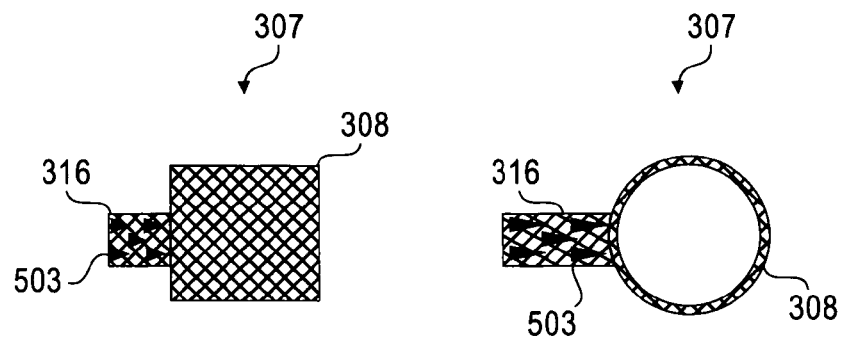

FIGS. 22A-22B illustrate a proximal anchoring member 307 that can be used for the proximal anchoring member 204 shown in FIGS. 2A-2B. The proximal anchoring member 307 is similar to the proximal anchoring member 304 previously described except that the flange portion 306 of the proximal anchoring member 304 is now replaced with an arm 316 that includes a plurality of anchors 503. The proximal anchoring member 307 includes a distal tube 308 similar to the proximal anchoring member 304. The anchors 503 are useful when it is necessary to penetrate the right trigone to gain desired support levels to provide an effective therapy. In some cases, it is desired that the locations of any anchors 503 that are directed to the right trigone be controlled. Controlling the length of the arm 316 controls the placement of the anchors 503. The desired length of the arm 316 may be determined dependant upon the distance from the entrance 216 of the CS 208 to the right trigone. The distance from the entrance 216 of the CS 208 to the right trigone may be obtained using conventional methods such as TEE (Transesophageal Echo) and TTE (Transthoracic Echo). The proximal anchoring member 307 with the arms 316 may be provided with the arms 316 having various lengths to accommodate anatomy/disease state variations. In one embodiment, the proximal anchoring member 307 comprises at least one radiopaque marker to aid in the orientation/placement of the arm 316. The arm 316 and the distal portion 308 can be coated with materials, coatings, or drugs that encourage the incorporation or anchoring of the proximal anchoring member 307.

FIGS. 23-28 illustrate cross-sectional views of exemplary embodiments of delivery devices that can be used to deliver and deploy a telescoping assembly (e.g., the telescoping assembly 220), a distal anchoring member (e.g., the distal anchoring member 302), and a proximal anchoring member (e.g., the proximal anchoring member 304) that can be used to treat mitral valve regurgitation.

Figure 23:
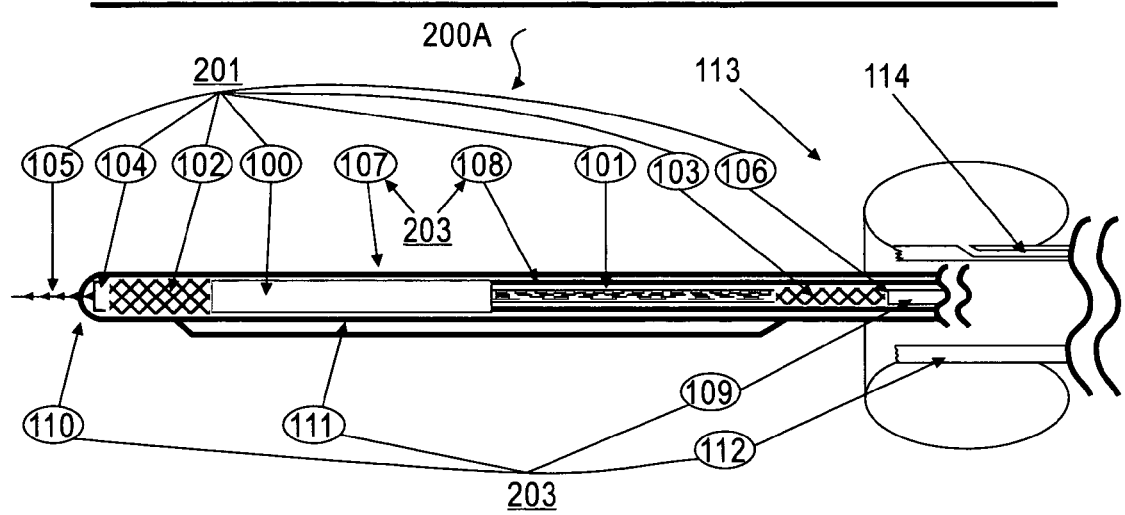
FIG. 23 is an illustration of an annuloplasty device disposed within a delivery device that can be delivered into a coronary sinus in accordance with the embodiments of the present invention.

FIG. 23 illustrates an exemplary medical device 200A that can be used to treat mitral valve regurgitation. Although the discussion below focuses on treating mitral valve regurgitation, the medical device 200A can be used to treat other conditions that require reforming, reshaping, or reducing a blood vessel. The medical device 200A comprises an annuloplasty device 201 and a delivery device 203. The annuloplasty device 201 is deployed near, at, in, or within the CS 208 while the delivery device 203 is used to deliver the annuloplasty device 201 to the CS 208.

In one embodiment, the annuloplasty device 201 of the medical device 200A comprises a distal tube 100, a proximal tube 101, a distal anchoring member 102, a proximal anchoring member 103, a position-locking device 104, a cord assembly 105 (only a portion of which is visible) and a detaching mechanism 106.

The delivery device 203 of the medical device 200A comprises an outer sheath 107, an inner sheath 108, an atraumatic distal tip 110, an inner shaft 109, and a guidewire lumen 111. In one embodiment, the outer sheath 102 includes the atraumatic distal tip 110 and the guidewire lumen 111.

The delivery device 203 is used to introduce the annuloplasty device 201 to the treatment site. The delivery device 203 is withdrawn after the distal tube 100, the proximal tube 101, the distal anchoring member 102, and the proximal anchoring member 103 are deployed. Note that the outer sheath 107, the inner sheath 108, the inner shaft 109, and the detaching mechanism 106 are shown in sectional side view in FIG. 23 to expose the annuloplasty device 201.

In one embodiment, a portion of the detaching mechanism 106 belongs to the annular device 201 and a portion of the detaching mechanism 106 belongs to the delivery device 203. Thus, the detaching mechanisms 106 may contain portions that remain with the annuloplasty device 201 that is delivered or deployed in the CS 208.

In one embodiment, the cord assembly 105 includes a lumen (not shown). A guidewire can be disposed through this lumen thus eliminating the need for having a guidewire lumen 111 in the outer sheath 107 to guide the annuloplasty device 201 of the medical device 200A into the CS 208.

In one embodiment, both the distal anchoring member 102 and proximal anchoring member 103 are configured as self-expanding structures. The distal anchoring member 102 can be any of the distal anchoring members previously described. The proximal anchoring member 103 can be any of the proximal anchoring members previously described. In one embodiment, the proximal anchoring members comprise anchors (not shown); these anchors are not oriented distally relative to the proximal anchoring members to prevent the anchors from penetrating into the inner sheath 108 of the delivery device 203 and prevents the withdrawal of the inner sheath 108. In another embodiment, the proximal anchoring members comprise anchors that may be oriented distally and another delivery device such as those shown in FIGS. 26-28 (see below) can be used to deliver/deploy the annular device with these proximal anchoring members.

Continuing with FIG. 23, the distal tube 100 and the proximal tube 101 form a telescoping assembly much like the telescoping assembly 220 previously described except only two tubes are used instead of three tubes as in the telescoping assembly 220. The proximal tube 101 and the distal tube 100 can slide inward and outward from each other. In one embodiment, the proximal tube 101 enters the inner diameter of the distal tube 100 for a short distance, forming a telescoping section. The distal end of the distal tube 100 is further attached to one side of the distal anchoring member 102. The proximal end of the proximal tube 101 is attached to one side of the proximal side of the proximal anchoring member 103.

Still referring to FIG. 23, in one embodiment, the proximal portion of the cord assembly 105 is attached to the proximal end or any other portion of the proximal tube 101. In another embodiment, the proximal portion of the cord assembly 105 is attached to the proximal end of the detaching mechanism 106. The distal end of the cord assembly 105 goes through the position-locking device 104. The cord assembly 105 extends some distance out of the position-locking device 104. The bulk of the cord assembly 105 (not visible) runs through the inner diameters of the distal tube 100 and the proximal tube 101. The cord assembly 105 is used by the operator (e.g., a physician) to adjust the length and/or tension of the annuloplasty device 201 of the medical device 200A.

For example, pulling on the cord assembly 105 moves the distal tube 100 and the proximal tube 101, thereby telescoping the tubes, one relative to the other, thereby adjusting the length of the device. The cord assembly 105 may be used to apply tension upon the distal anchoring member 102 or the proximal anchoring member 103. For example, when the cord assembly 105 is also attached to an end of the distal anchoring member 102, pulling on the cord assembly 105 adjusts the length of the annuloplasty device 201 of the medical device 200A when the cord assembly 105 is relatively inelastic. Pulling on the cord assembly 105 adjusts its length and (installed) tension, when the cord assembly 105 is relatively elastic. With the CS 208 being curved, the deployed/delivered annuloplasty device 201 tends to curve to the curvature of the CS 208. When the annuloplasty device 201 is placed under tension (as caused by pulling the cord assembly 105, a force is applied to the annuloplasty device 201 and hence, the CS 208, reducing the curvature of the CS 208 and pushing the posterior leaflet closer to the anterior leaflet as previously described.

In one embodiment, an extension-limiting cord (not shown) is disposed within the inner diameters of each of the distal tube 100 and the proximal tube 101. One end of the extension-limiting cord is attached to the distal tube 100 and one end of the extension-limiting cord is attached to the proximal tube 101. The length of the extension-limiting cord is fixed such that if the distal tube 101 and the proximal tube 100 are moved away from each other, the extension-limiting cord dictates the maximum length or distance that the distal tube 100 and the proximal tube 101 can move away from each other.

After all the necessary adjustment, the cord assembly 105 is locked in position by the position-locking device 104. In one embodiment, the position-locking device 104 is attached to the distal end of the distal tube 100.

The position-locking device 104 can be an interference locking ratchet-like mechanism well known in the art that can be used to lock the cord assembly 105. The position-locking device 104 may include an opening created in an elastic diaphragm and the cord assembly 105 may include beads. The cord assembly 105 may be pulled in one direction, for example, distally with respect to the position-locking device 104. One of the beads on the cord assembly 105 would be trapped at the opening thereby locking the cord assembly 105 into a position, which prevents the cord assembly 105 from moving backward (e.g., proximally). Each of these configurations of the position-locking device 104 operates to allow the cord assembly 105 to be pulled in one direction and locked in position. Correcting or adjusting the cord assembly 105 in the event of over tightening is difficult in these configurations. For instance, a great deal of force must be applied to pull the cord assembly 105 in the opposite direction. However, since the position-locking device 104 is on the distal end of the annuloplasty device 201 as shown in FIG. 23 and is relatively accessible to the physician, a tool may be provided to facilitate the correction of an over-tightening situation. When the cord assembly 105 has been properly adjusted for the patient's anatomy, the physician may clip off any excess at the distal end of the cord assembly 105.

Figure 24A:
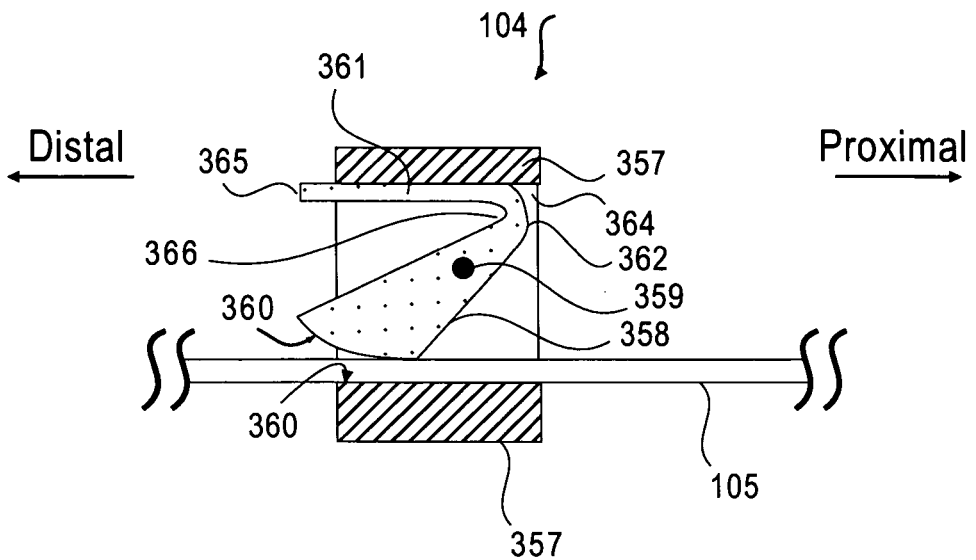
FIGS. 24A-24B illustrate exemplary embodiments of position-locking devices that can be used for annuloplasty devices in accordance with the embodiments of the present invention.

In one embodiment, the position-locking device 104 comprises of a housing 357, an arm 358 and a pivot 359 as shown in FIGS. 24A. The housing 357 is shown partially cut-away and the cord assembly 105 is shown inserted into the housing 357. One side of the cord assembly 105 rides against the inside surface 360 of the housing 357. In one embodiment, the cord assembly 105 may be guided and/or held (slidably proximal and distal) in this position by features of the housing 357 or features attached to the housing 357 such as slots or holes (not shown).

Continuing with FIGS. 24A, the arm 358 is rotatably attached to the inner diameter of the housing 357 by the pivot 359. The pivot 359 may be a separate component, such as a pin or shaft, or it may be incorporated into the features of the housing 357 and the arm 358. For instance, the arm 357 may be molded with cylindrical projections that engage holes in the housing 357 to perform the functions of the pivot 359. The lever portion 361 of the arm 358 is constructed such that the area 362 of the lever portion 361 is elastically deformed when the cord assembly 105 is inserted into the housing 357, as shown. This elastic deformation imparts a force on the arm 358 such that it will rotate on the pivot 359, causing the surface 363 of the arm 358 to contact the cord assembly 105, as shown.

The lever portion 361 and the surface 364 of the housing 357 may be designed and/or constructed and/or coated in a manner such that the friction between them is low. This allows the portion 361 to move relative to the surface 364 as the arm 358 pivots. The surface 363 is constructed such that its distance from the pivot 359 increases distally. Thus, if the cord assembly 105 is moved distally (relative to the position-locking device 104), the engagement/friction of the cord assembly 105 with the surface 363 will rotate the surface 363 clockwise causing the contacting surface of the surface 363 to tend to move away or disengage from the cord assembly 105. Thus the cord assembly 105 may be pulled distally. Conversely, if the cord assembly 105 is moved proximally (relative to the position-locking device 104), the engagement of the cord assembly 105 with the surface 363 will rotate the surface 363 counterclockwise causing the contacting surface of the surface 363 to pinch the cord assembly 105 between the surface 363 and the housing surface 360. This pinching constrains the cord assembly 105 from moving proximally.

In one embodiment, the surface 363 and/or the applicable surface of the cord assembly 105 may be coated with or made of materials to increase the friction between them and/or be contoured to mechanically engage (like gear teeth of various configurations) and thus assure that pinching reliably occurs. In one embodiment, the position-locking device 104 is configured such that the surface 363 engages the housing surface 360, if the cord assembly 105 is not present. This keeps the position-locking device 104 in a state such that the cord assembly 105 may be easily inserted into the position-locking device 104.

In one embodiment, prior to insertion into the body, the physician may grasp the distal end of the outer sheath 107 and pull on the distal end of the cord assembly 105 to set the length and/or tension (depending upon the elasticity of the cord assembly 105) of the annuloplasty device. There may be indicator markings/colors on the distal end of the cord assembly 105 or the outer sheath 107 may be see-through and contain a scale or a scale may be placed on tube 101 to facilitate the proper and repeatable setting.

In one embodiment, the length and/or tension of the annuloplasty device 201 of the medical device 200A is adjusted prior to being introduced into a patient. To adjust the annuloplasty device of the medical device 200A prior to introducing it into the patient, an operator (e.g., a physician) needs to know the length and curve that the annuloplasty device of the medical device 200A needs to be at in order to reshape the mitral valve annulus or the mitral valve. Methods such as TEE (Trans-Esophageal Echo) or TTE (Transthoracic Echo) imaging devices and methods can be used by the operator or the physician to diagnose mitral valve anomalies and to size the annuloplasty device 201 of the medical device 200A accordingly. Other methods that help the physician determine the anomalies of the mitral valve may also be used. The physician may use the image information to determine the desired length and/or shortening force of the annuloplasty device 201 of the medical device 200A. The annuloplasty device 201 of the medical device 200A can then be adjusted outside of the patient and be deployed into the patient with the proper length or tension.

Returning to FIG. 23, the distal end of the delivery device 203 of the medical device 200A is shown in a cutaway section. The outer sheath 107 can be a catheter having at least one elongate lumen. The outer sheath 107 includes a slitted/slotted distal tip 110 and the guidewire lumen 111. One function of the outer sheath 107 is to constrain the distal anchoring member 102 in a pre-delivery or pre-deployment state. The inner diameter of the outer sheath 107 constrains the outer diameter of the distal anchoring member 102. The outer diameter of the distal anchoring member 102 should be constrained to the smallest outer diameter practical given the outer diameter of the distal tube 100. The outer sheath 107 may also incorporate a radiopaque marker(s) (not shown) to provide fluoroscopic positioning information.

The inner sheath 108 is slidably disposed within the inner diameter of the outer sheath 107. The inner sheath 108 is also elongate and contains at least one lumen. The distal end of the inner sheath butts up against the proximal end of the tube 100. One function of the inner sheath 108 is to constrain the proximal anchor 103 in a pre-delivery or pre-deployment state. The inner diameter of the inner sheath 108 constrains the outer diameter of the proximal anchoring member 103. The outer diameter of the proximal anchoring member 103 should be constrained to the smallest outer diameter practical. The inner sheath 108 may also contain a radiopaque marker(s) (not shown) to provide fluoroscopic positioning information.

An inner shaft 109 is slidably contained within the inner diameter of the inner sheath 108. The distal end of the inner shaft 109 contains features that allow it to be attached and detached from the detaching mechanism 106. The detaching mechanism 106 comprises a distal and proximal portion. The distal portion is attached or incorporated into the proximal end of the telescoping assembly, the proximal tube 101. The proximal portion is attached or incorporated into the distal end of the inner shaft 109. The detaching mechanism 16 is used to detach the delivery device 203 from the annuloplasty device 201 after the annuloplasty device 201 has been deployed into its final position in the CS 208. For instance, the detaching mechanism 106 could contain screw threads, in which case the distal end of the inner shaft 109 would contain the mating threads. The detaching mechanism 106 could be a loop, in which case the distal end of the inner shaft 109 could be hollow and containing an engaging loop. The loop can be a cord, wire, filament, or a hook, to name a few. There are many engagement/disengagement mechanisms that rely on rotary and/or longitudinal motion and/or the release of one end of a cord.

In one embodiment, the distal anchoring member 102 is deployed in the CS 208. The distal anchoring member 102 is deployed before the proximal anchoring member 103 is deployed. To deploy the distal anchoring member 102, the outer sheath 107 is withdrawn proximally relative to the inner sheath 108. The outer sheath 107 is also withdrawn proximally relative to the proximal anchoring member 103. During deployment, the distal anchoring member 102 remains stationary. One reason for that is that the distal anchoring member 102 is attached to the distal tube 100, which is held stationary by being butted up against the inner sheath 108. Thus, the inner sheath 108 is held stationary while the outer sheath 108 is pulled proximally, thereby exposing the distal anchoring member 102 and the distal tube 100 and the proximal tube 101. The outer sheath 107 can be withdrawn proximally over the distal anchoring member 102 and the tubes 100 and 101 while the distal anchoring member 102 and the tubes 100 and 101 remain in place in the CS 208 because of the opening in the slitted/slotted distal tip 110 which opens enough to allow the outer sheath 107 to be slid over the distal anchoring member 102 and the tubes 100 and 101.

Once the distal anchoring member 102 is deployed, the proximal anchoring member 103 must be pulled proximally into position near or at the entrance to the CS 208 for deployment. Pulling the proximal anchoring member 103 may deform and/or reposition the anatomy of the heart as well as other anatomical structures along the path of the annuloplasty device 201 of the medical device 200A especially when the annuloplasty device 201 has already been pre-sized to have a length that is sufficiently short to reduce or reform the mitral valve annulus. The desired position of the proximal anchoring member 103 is attained prior to deployment using a balloon on a guide catheter shaft 112. The delivery device 203 is disposed within the inner diameter of the guide catheter shaft 112. The guide catheter shaft 112 couples to a dilatable/inflatable balloon 113. The guide catheter shaft 112 may have any of the constructions common to guides and/or introducer sheaths/catheters. The guide catheter shaft 112 includes a lumen 114 to inflate or dilate the balloon 113. The lumen 114 is in communication with the proximal end of the guide catheter in a manner that facilitates the inflation and deflation of the balloon 113. Any of the common angioplasty balloon materials may be used. In one embodiment, the balloon 113 is made of nylon (e.g., Pebax blend or nylon/Pebax blend materials that are commonly use in guide/introducer construction) balloon materials.

Once the distal anchoring member 102 is deployed, the proximal anchoring member 103 is positioned by first inflating the balloon 113. The inner shaft 109 is pulled proximally with one hand, while grasping the proximal end of the guide catheter shaft 112 with the other hand and pushing in the opposite direction. This forces the guide catheter shaft 112 to move distally such that the distal end of the inflated balloon 113 pushes against the right atrium wall. From that point on, the bulk of the force and longitudinal displacement applied between the inner shaft 109 and the guide catheter shaft 112 is applied mainly to the distance between the distal anchoring member 102 and the balloon 113 contact areas around the entrance to the CS 208. Once the correct position for the proximal anchoring member 103 is attained, the inner shaft 109 is withdrawn to deploy the proximal anchoring member 103.

In one embodiment, the annuloplasty device 201 is delivered into the CS 208 using the following procedure. First, the operator (e.g., a physician) gains access to a vein (e.g., femoral, jugular, subclavian, etc. . . . ) in a patient's body using a cut-down or an introducer sheath procedure. The vein is used to introduce the medial device 200A into the right atrium and then into the CS 208. In the introducer sheath procedure, the physician introduces the introducer sheath into the vein through the patient's skin percutaneously. A needle or a similar puncture device provides entry into the vein. The proximal end of the needle remains outside of the introducer sheath and is withdrawn. A distal end of the catheter guide shaft 112 with a flexible guidewire (not shown) in its inner diameter is inserted into the proximal end of the introducer sheath and advanced therethrough until the distal end of the guidewire or the guide catheter shaft 112 reaches the vicinity of the CS 208.

Second, the guidewire and the catheter shaft 112 are manipulated to gain access to the entrance to the CS 208. Once the guide catheter shaft 112 is inserted into the CS 208 a short distance, the guidewire may be withdrawn proximally from the guide catheter shaft 112 and replaced with another guidewire (not shown) that is suitably sized for the lumen 111 of the outer sheath 107. This other guidewire is inserted into the proximal end of the guide catheter shaft 112 until its distal end is distal to the desired position of the distal anchoring member 102.

Third, the length of the annuloplasty device 201 of the medical device 200A is adjusted to a desirable length outside of the patient using the cord assembly 105. Excess portion of the cord assembly 105 may be cut off. The physician may also flush the delivery system, the guide catheter 112 and the annuloplasty device 201 of the medical device 200A.

Fourth, the annuloplasty device 201 disposed within the delivery device 203 is inserted into the guide catheter 112 and over the guidewire. The guidewire is inserted within the guidewire lumen 111 so that the annuloplasty device 201 of the medical device 200A can be inserted over it and into the inner diameter of the guide catheter shaft 112. The annuloplasty device 201 of the medical device 200A is advanced until the distal portion of the annuloplasty device 201 reaches an area in the CS 208 where the distal anchoring member 102 is to be deployed, for example, in the vicinity of the left trigone.

Fifth, the physician withdraws this other guidewire and deploys the distal anchoring member 102. The physician withdraws the guidewire proximally and removes it from the proximal end of the guide catheter shaft 112. The physician withdraws the outer sheath 107 to deploy the distal anchoring member 102. The outer sheath 107 is withdrawn proximal to the proximal anchoring member 103.

Sixth, the physician positions and deploys the proximal anchoring member 103. The guide catheter shaft 112 is withdrawn until the distal tip of the guide catheter shaft 112 is not in the CS 208. The balloon 113 is inflated, for example, by air, water, saline, contrast, gas, etc. . . . The guide catheter shaft 112 is advanced distally until the guide catheter 112 contacts the right atrium wall. In one embodiment, the physician grasps the proximal end of the guide catheter shaft 112 in one hand and the proximal and of the inner shaft 109 in the other hand and moves them apart. This action moves the proximal anchoring member 103 to the desired location, for example, at the entrance of the CS 208. The inner sheath 108 is then withdrawn to deploy the proximal anchoring member 103.

Seventh, after deploying the distal anchoring member 102 and the proximal anchoring member 103, the balloon 113 is deflated. The physician manipulates the detaching mechanism 106 to release the annuloplasty device 201 from the inner shaft 109. The physician may then withdraw and remove the delivery device 203 proximally form the guide catheter shaft 112. The physician may then withdraw and remove the introducer sheath from the patient. The length and resistance to curvature (flexural modulus) of the telescoping assembly then acts to reshape the CS 208 thereby reshaping the mitral valve annulus 209. In one embodiment, reshaping the mitral valves annulus 209 includes moving the posterior leaflet of the mitral valve toward the anterior leaflet of the mitral valve and thus reduces or eliminates regurgitation.

The annuloplasty device need not have its length or tension pre-adjusted prior to introducing it into the patient. In one embodiment, the position-locking device 104 is attached to the proximal end of the proximal tube 101 or to the proximal anchoring member 103 to allow for adjustment of the length or tension of the annuloplasty device after its deployment into the CS 208. Such an embodiment is a medical device 200B illustrated in FIG. 25 below. The position-locking device 104 for the annuloplasty device of the medical device 200B is oriented in the opposite direction (see FIG. 24B) from the one for the annuloplasty device 201 of the medical device 200A described above.

Figure 25:
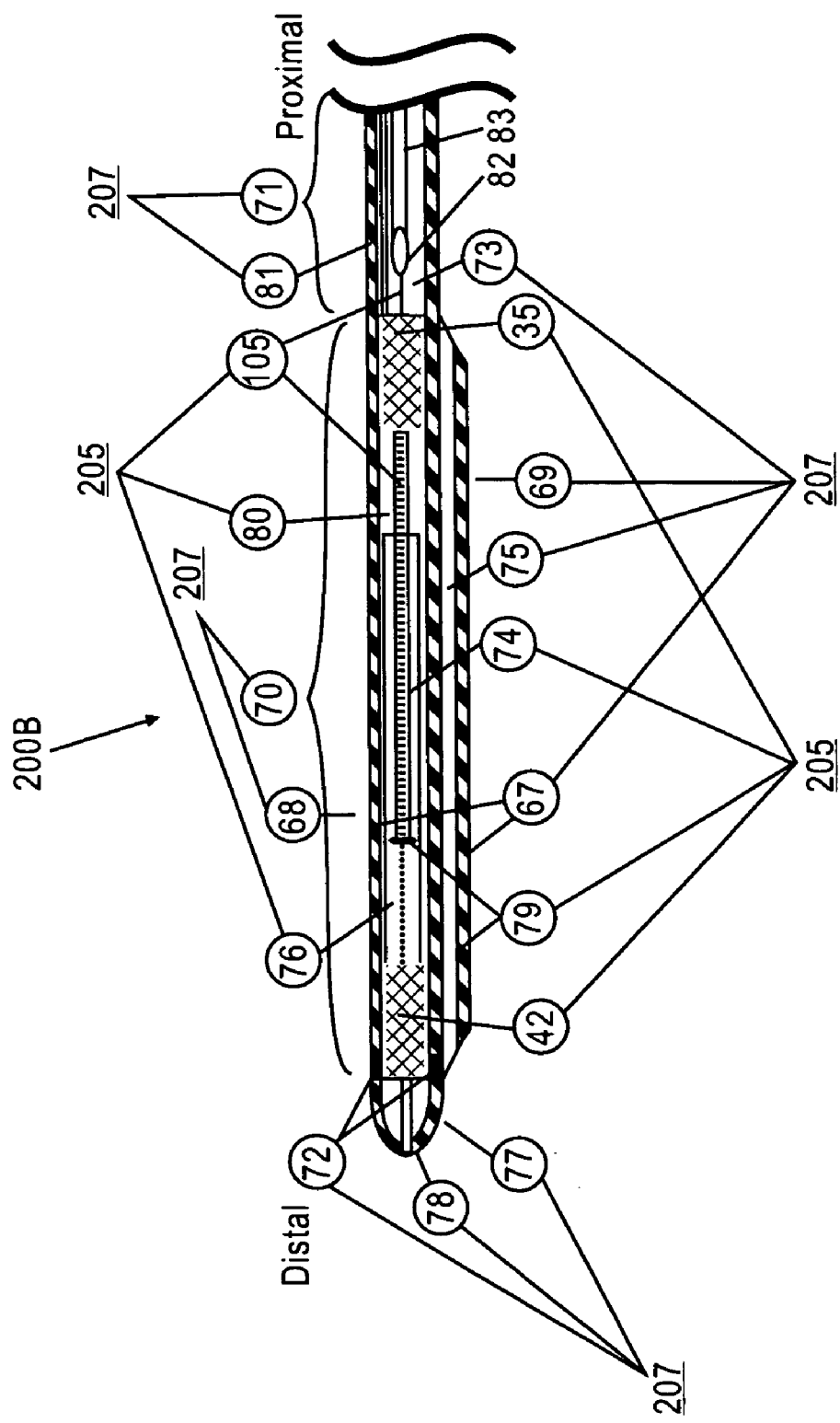
FIG. 25 is an illustration of an annuloplasty device disposed in a delivery device that can be delivered into a coronary sinus in accordance with the embodiments of the present invention.

FIG. 25 illustrates an exemplary embodiment of a medical device 200B that can be used to treat mitral valve regurgitation. Although the discussion below focuses on treating mitral valve regurgitation, the medical device 200B can be used to treat other conditions that require re-shaping or reducing a blood vessel. The medical device 200B is similar to the medical device 200A described above except that the annuloplasty device of the medical device 200B has the position-locking device 104 attached to the proximal end of the telescoping assembly and that the annuloplasty device of the medical device 200B allows for adjustment to the length and/or tension of the annuloplasty device of the medical device 200B after the annuloplasty device of the medical device 200B has been introduced into the patient.

As illustrated in FIG. 25, the medical device 200B comprises an annuloplasty device 205 and a delivery device 207. The annuloplasty device 205 comprises a distal anchoring member 42, a telescoping assembly 74, a proximal anchoring member 35, a cord assembly 105, and a position-locking device 104 which is not visible in FIG. 25 but which is attached to the proximal end of the proximal anchoring member 35 or the proximal tube 80.

The telescoping assembly 74 can also be the telescoping assembly 220 previously described, but for simplicity only two tubes are included in FIG. 25. The telescoping assembly 74 of the annuloplasty device 205 may comprise a distal tube 76 and a proximal tube 80. The distal tube 76 can slide into the proximal tube 80, similar to that previously described for the telescoping assembly 220. The inner diameter of the distal tube 76 is shown with two steps in its inner diameter that will interfere with the outer diameter step 79 on the distal end of the proximal tube 80, such that the outer diameter step 79 is captured. The proximal tube 80 thus only telescopes between the two inner diameter steps of the distal tube 76. The outer diameter step 79 is shown up against the inner diameter step of the distal tube 76, and therefore, the full device is shown in FIG. 25 at its shortest length, which should be chosen to be shorter than the deployed device length and to preferably also be the target minimum modified annulus length. In another embodiment, the telescoping assembly 74 may be mounted in the annuloplasty device 205 of the medical device 200B such that it is at or near its longest length to provide the greatest flexibility to the distal section 70 and thus provide the easiest delivery to the CS 208.

The delivery device 207 delivers and deploys the annuloplasty device 205 to the treatment site (e.g., the CS 208) to reshape the mitral valve annulus 209. The delivery device 207 of the medical device 200B comprises an outer sheath 67 and an inner sheath 73. In one embodiment, the outer sheath 67 (shown as a cutaway section) is slidably mounted over the outer diameter of the inner sheath 73. The distal end of the outer sheath 67 may be withdrawn proximally to a position that is proximal to the distal end of inner sheath 73. Similar to the annuloplasty device 201 of the medical device 200A, the proximal withdrawal of the outer sheath 67 allows the annuloplasty device 205 of the medical device 200B to be deployed. The delivery device 207 further includes a distal tip 77, a distal section 70 and a proximal section 71. The distal tip 77 is part of the outer sheath 67 and is attached to the distal section 70 to provide an atraumatic tip to the outer sheath 67. The atraumatic distal tip 77 may include one or more cut slots/slits 78 (or cuts or partial cuts), such that when the outer sheath 67 is withdrawn over the inner sheath 63, the tip 77 opens and passes over the distal end of the inner sheath 73. In another embodiment, the atraumatic distal tip 77 may be incorporated into the distal end of the telescoping assembly of the annuloplasty device 205, or if present, the position-locking device.

In one embodiment, the outer sheath 67 has variable wall thickness/flexural modulus. For example, the distal portion 70 of the outer sheath 76 has a side 69 and a side 68 wherein the side 69 has a higher flexural modulus (higher stiffness) than the side 68. The high flexural modulus on the side 69 allows for orientation control of the delivery device 207 and thereby, the annuloplasty device 205 as previously described.

Controlling the orientation of the delivery device 207 allows the anchoring members and the telescoping assembly 74 to be deployed in a proper orientation (e.g., these elements are in contact with the wall of the CS 208 which faces the mitral valve annulus 209). In one embodiment, some portions of the distal section 70 include in its construction stiffer materials in the form of wires, rods, partial tube sections and other shapes to provide the desired change in flexural modulus.

In one embodiment, the outer sheath 67 includes a guidewire lumen 75 at the distal portion 70. The guidewire lumen 75 may be located on the side 69 of the distal portion 70. The guidewire lumen 75 accommodates a guidewire (not shown) to facilitate the delivery of the annuloplasty device 205 of the medical device 200B. Also, the incorporation of the guidewire lumen 75 into the outer sheath 67 requires the addition of material that may provide the differential flexural modulus in the distal section 70 that provide the orientation control previously described. In one embodiment, the outer sheath 67 includes at least one radiopaque marker 72 that aids in the positioning of the deployment of the annuloplasty device 205 of the medical device 200B.

In one embodiment, the distal tube 76 is attached to the distal anchoring member 42 and the proximal tube 80 is attached to the proximal anchoring member 35. The distal anchoring member 42 and the proximal anchoring member 35 can be any of the anchoring members previously described.

In one embodiment, the telescoping assembly 74 is disposed on the inner diameter of the outer sheath 67 on the side that curves to the curve of the CS 208 such that the distal anchoring member 42, the telescoping assembly 74, and the proximal anchoring member 35 are in contact with the wall of the CS 208 that faces the mitral valve annulus. Delivering the annuloplasty device 205 in this manner ensures that subsequent tension on the cord 105 will not introduce undesirable forces on the distal anchoring member 42 and the proximal anchoring member 35.

Figure 24B:
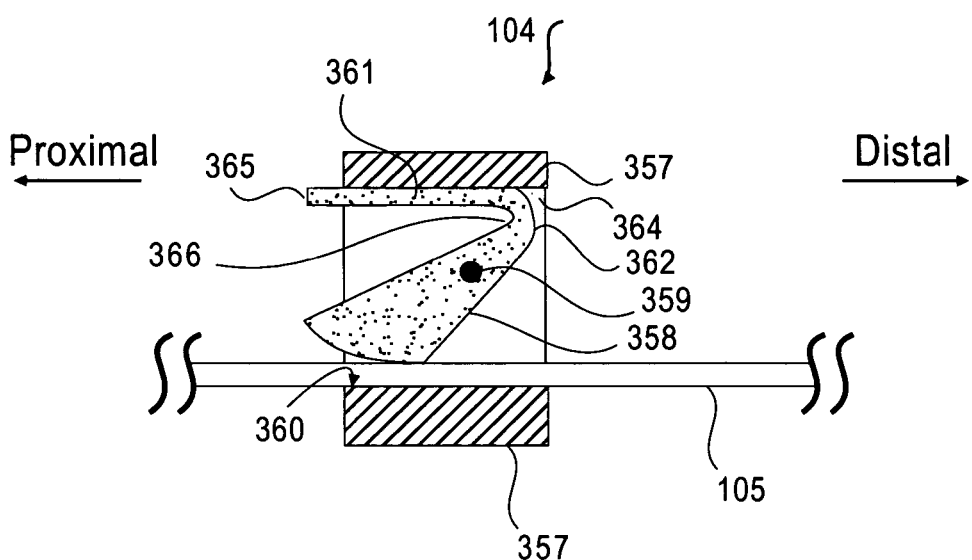

FIG. 24B illustrates a position-locking device 104 that can be used for the annuloplasty device 205 of the medical device 200B. This position-locking device 104 is the same as previously described in FIG. 24A except that the position of the arm 358 is opposite from the one shown in FIG. 24A.

In one embodiment, the position-locking device 104 enables adjustment of the cord assembly 105. The position-locking device 104 may be manipulated in several simple ways to allow the cord assembly 105 to be released in the event of over-tightening. In one embodiment, a pin/wire is inserted through the inner sheath 73 and pushed out to engage the surface 366 of area 362, and then the arm 358 will pivot away from the cord assembly 105 releasing it. In another embodiment, a similar pin or catheter end portion may engage and push on the surface 365 of the lever 361 to cause the arm 358 to pivot away from the cord assembly 105 to releasing the cord assembly 105. An example of such a pin/wire is a push wire 81 shown in FIG. 25. The amount of force/pressure required for release can be reduced dramatically by also pulling the cord assembly 105 proximally slightly. Once released the amount of force/pressure on the surface 365 or 366 required to keep the cord assembly 105 released will be near this lower level. Thus either of the previously described release methods may be combined with a small proximal pull, then release of the cord assembly 105 relative to the engaging catheter to release the cord assembly 105 from the position-locking device 104 using a minimal force/pressure.

In one embodiment, the position-locking device 104 is attached to or interferes with the proximal anchoring member 35 in a convenient manner such that the cord assembly 105 is routed through the inner diameter of proximal tube 80. In another embodiment, the position-locking device 104 is attached to or interferes with the proximal tube 80 in a convenient manner such that the cord assembly 105 is routed through its inner diameter.

In one embodiment, when the outer sheath 67 is withdrawn, the distal anchoring member 42, the telescoping assembly 74, and the proximal anchoring member 34 will be exposed and thus deployed. The distal end of the inner sheath 73 engages the position-locking device 104 (which is attached to the proximal tube 80), as previously described. In one embodiment, the inner sheath 73 comprises at least two lumens (not shown), which accommodate the cord puller 83 and the lock release push wire 81. The proximal end of the cord assembly 105 is formed as a loop 82 and puller cord 83 goes through that loop. When the two ends of puller cord 83 are pulled, then the cord assembly 105 is tightened. When only one end of the puller cord 83 is pulled, its unpulled end is pulled through the inner diameter of one of the lumens of the inner sheath 73 and through the loop 82 disengaging the full annuloplasty device from inner sheath 73. In one embodiment, the push wire 81 acts as previously described to allow the unlocking of the cord assembly 105 from the position-locking device 104 for adjustment in the event of over tightening.

In one embodiment, the cord assembly 105 and the surface 360 of the housing 357 are designed and/or constructed and/or coated in a manner such that the friction between them is not an appreciable portion of the desirable tension for the cord assembly 105 during tightening. This provides the physician with tactile feedback or the tightening monitoring of the annuloplasty device of the medical device 200B. The tactile feedback for the tightening monitoring is useful when the tightening of the cord assembly 105 occurs while the annuloplasty device of the medical device 200B is deployed/delivered inside the body.

In one embodiment, the inner sheath 73 comprises a metallic braid, coil(s) and/or slotted tube in its wall to aid the inner sheath 73 in resisting compression during device deployment and still keep the necessary flexibility for deliverability and the desirable thin walls to make the delivery system as small in outer diameter as practical.

In one embodiment, the delivery device portion of the medical device 200A or 200B is configured to have a preferred orientation that is similar to the curve of the blood vessel (or the CS 208). For example, as mentioned above, the outer sheath 107 of the delivery device 203 of the medical device 200A or the outer sheath 67 of the delivery device 207 of the medical device 200B has sections with variable flexural modulus. The suitable delivery device may have sides or sections that have a higher flexural modulus such that one side of the delivery device is stiffer than the opposite side. Such a delivery device helps aligning the distal anchoring and the proximal anchoring members with the delivery device's preferred orientation. One advantage for the orientation is that the anchors that may be present in the distal anchoring or the proximal anchoring members are oriented to the inside of the curve. Delivery devices for the medical devices 200A or 200B with differential stiffness or variable flexural modulus can be made using well known methods in the art. In an embodiment where the outer sheath of the delivery device includes a hollow shaft, the wall of the hollow shaft may have its wall made thicker on one side than the other. In an embodiment where the delivery device includes an extruded tube that is made with its wall on one side thicker than the other. In one embodiment, the delivery device includes a shaft that is made out of two different grades of similar (miscible) plastics, where one grade is stiffer than the other grade, either by co-extrusion or other melt processes, such as melting cut lengths of the two materials (in a properly formed condition) within a shrink tubing over a mandrel. In one embodiment, the delivery device may have a stiffer material inserted/melted into one side of the delivery device.

Additionally, orienting the distal anchoring and the proximal anchoring members in a particular orientation (e.g., toward the inside curve of the CS 208) aids the anchors that may be included in the distal anchoring and the proximal anchoring members to project toward and/or penetrate toward the inside of the curve of the blood vessel as discussed above. Also, the anchors may be oriented in any other direction that will prevent the anchors from damaging other vessels or other thinner sections of the heart.

The annuloplasty device 205 of the medical device 200B can be deployed using the following exemplary procedure. Using conventional methods, the CS 208 is accessed by a guide catheter (or guide catheter with an occluding balloon and/or deflection capabilities) and a guidewire. Using angiography (with the guide catheter and contrast injections through the guide catheter) and/or previously obtained or concurrent echo data, the desired position of the distal anchoring member 42 is determined. Fluoroscopic/angiographic observation methods can be used to aid the physician in deploying the annuloplasty device 205 of the medical device 200B. These methods are well known in the art.

The annuloplasty device 205 disposed within the delivery device 207 is advanced over the guidewire using the lumen 75 until the distal end of the distal anchoring member 42 is in the desired position, for example, an area in the CS 208 that is proximate the left trigone. The guidewire is withdrawn/removed from the CS 208. To deploy the distal anchoring member 42, the inner sheath 73 is used to hold the distal anchoring member 42 in position (via the telescoping assembly 74) while the outer sheath 67 is withdrawn until the marker 72 and the distal tip 77 pass the proximal end of the distal anchoring member 42. Once the distal anchoring member 42 is deployed, it engages the inner wall of the CS 208 and is fixed in position. The push wire 81 is then advance to release the cord assembly 105 from the position-locking device 104, as described above and the proximal end of the delivery device 207 is withdrawn proximally, lengthening the telescoping assembly 74, until the proximal anchoring member is at the desired position in the CS 208. The proximal anchoring member 35 is then deployed at the entrance to the CS as the outer sheath 67 is further withdrawn. The inner sheath 73 is used to hold the proximal anchoring member 35 in position while the outer sheath 67 is withdrawn until the marker 72 and the distal tip 77 pass the proximal end of the proximal anchoring member 35. The length and tension of the annuloplasty device 205 of the medical device 200B is then adjusted by pulling on both ends of the puller cord 83 relative to the inner sheath 73 to place tension/longitudinal motion on the cord assembly 105. When the cord assembly 105 has been given the proper amount of tension, shortening and/or the valve regurgitation has been eliminated or reduced to the target amount, one end of the puller cord 83 is released and withdrawal of the puller cord 83 is continued until it releases the cord assembly 105. The delivery device 207 of the medical device 200B is then removed in a conventional manner.

FIGS. 26-28 illustrate an exemplary medical device 200C. The configuration of the medical device 200C is similar to the medical device 200B and includes most of the features of the medical device 200B described above. The medical device 200C includes an annuloplasty device 209 and a delivery device 211 which are similar to the annuloplasty device 205 and the delivery device 207 of the medical device 200B. FIG. 26 illustrates the distal end of the annuloplasty device 209 of the medical device 200C as it would be inserted into a guide and into the CS 208 wherein the annuloplasty device 209 is not yet deployed.

Similar to the annuloplasty device 205 of the medical device 200B, the annuloplasty device 209 of the medical device 200C comprises a distal anchoring member 42, a proximal anchoring member 35, and a telescoping assembly 88, which includes a center tube 87, a distal tube 90, and a proximal tube 91. The distal tube 90 and the proximal tube 91 can telescope into the center tube 87. Additionally, the annuloplasty device 209 of the medical device 200C includes a spring 89 which functions to bias the distal tube 90 and the proximal tube 91 to a minimal distance away from each other. For example, the spring 89 provides a small biasing force to cause the other tubes 90, 91 (shown in cutaway sectional views) to remain as far apart as possible in the absence of other forces. Without this biasing force the distal end of inner sheath 73 would not remain engaged with the position-locking device (not shown) on the proximal anchoring member 35 during deployment of the proximal anchoring member 35 on the right atrium wall.

All other features of the annuloplasty device 209 of the medical device 200C are similar to the annuloplasty device 207 of the medical device 200B previously described.

The delivery device 211 of the medical device 200C is similar to the delivery device 207 of the medical device 200B. The delivery device 211 comprises an inner sheath 73, an outer sheath 67, a distal tip 77, and at least one radiopaque marker 72. Additionally, the delivery device 211 includes a protective sheath 84 as illustrated in FIGS. 26-28. The distal tip 77 also includes a slit 78.

The outer sheath 67 of the delivery device 211 is of the same design as previously described for the delivery device 207 of the medical device 200B. The outer sheath 67 also includes a guidewire lumen 75 that is away from the viewer and, therefore, is not seen in this sectional view. The outer sheath 67 includes a radiopaque marker 72 and a distal tip 77, shown with the slot 78 to allow it to be withdrawn similar to the delivery device 207 of the medical device 200B. The sheath 67 also performs the orientation control which functions similarly to previously described. The inner sheath 73 of the delivery device 209 is also of the same design as previously described for the delivery device 207 of the medical device 200B.

As will be apparent with the discussion below, in one embodiment, the protective sheath 84 functions to constrain and shield the anchors 49 (e.g., barbs) that are present on the proximal anchoring member 35 from interfering with the withdrawal of the outer sheath 67 during deployment. Without this protection, the anchors 49, being directed distally, would engage the outer sheath 67 and prevent its withdrawal. The protective sheath 84 is cut longitudinally by a slit 85 and folded over into the shape of a tube. The protective sheath 84 presses up against the inner diameter of the outer sheath 67 in its slit portion. The distal end of the protective sheath 84 engages the proximal end of the distal anchoring member 42 and prevents the distal anchoring member 42 from moving proximally as the outer sheath 67 is withdrawn during deployment. The proximal portions of protective sheath 84 (not shown) may be a simple tube (containing no slit) that occupies the space between the inner diameter of the outer sheath 67 and the outer diameter of the inner sheath 73. As the outer sheath 67 is withdrawn just proximal to the distal anchoring member 42, the distal anchoring member 42 is deployed in the CS 208 or other blood vessel. Once the proximal anchoring member 35 is in position, the outer sheath 67 is withdrawn proximal to the proximal anchoring member 35 and the protective sheath 84 opens up as shown in FIG. 27. The protective sheath 84 may then be withdrawn proximal into the outer sheath 67 to not interfere with the rest of the deployment procedure.

In one embodiment, the slit portion of the protective sheath 84 includes elastic members 86 to aid the slit portion of the protective sheath 84 to open for the deployment of the proximal anchoring member 35. Often, even though the slit portion of the protective sheath 84 was molded or shaped to be relatively flat when unconstrained, after being shaped back into an arc or a tube form for a period of time, the protective sheath 84 may take back its original shape, arc or tube, due to the creep properties of many polymers. Thus, when the outer sheath 67 is withdrawn, the protective sheath 84 may not open up to deploy the proximal anchoring member 35 in the desired manner. The elastic members 86 are made of material(s) that will resume its shape in a way that helps that protective sheath 84 in opening up as the outer sheath 67 is withdrawn.

In one embodiment, when the outer sheath 67 is withdrawn, the opening of the protective sheath 84 is not necessarily all the way to a flat cross-section, some residual curvature may be desirable for its subsequent withdrawal into the outer sheath 67. Withdrawal of the protective sheath 84 into the outer sheath 67 causes the protective sheath 84 to refold into a tube-like cross-section.

In one embodiment, the opening up of protective sheath 84 allows the proximal anchor 35 to unfold in a manner that directs its anchors 49 away from the protective sheath 84. As can be understood, if the protective sheath 84 was not folded over the proximal anchoring device 35, then the anchors 49 would engage the inner diameter of the outer sheath 67 when it is withdrawn. In one embodiment, the slit 85 is oriented such that protective sheath 84 unfolds to a position behind the anchors 49. The protective sheath 84 can be subsequently withdrawn, as shown in FIG. 28. The opening up of protective sheath 84 behind the anchors 49 and toward the outside of the curve of the CS 208 may further aid in the orientation control of the delivery device 211 and thereby the annuloplasty device 209 of the medical device 200C.

As can be readily appreciated by one skilled in the art, the annuloplasty device 209 of the medical device 200C can be deployed using a procedure very similar to that previously described for delivering the annuloplasty device 205 of the medical device 200B but modified with the previously described steps to deal with the protection sheath 84 and to account for the telescoping assembly 88 being biased in its most extended condition.

Figure 29:
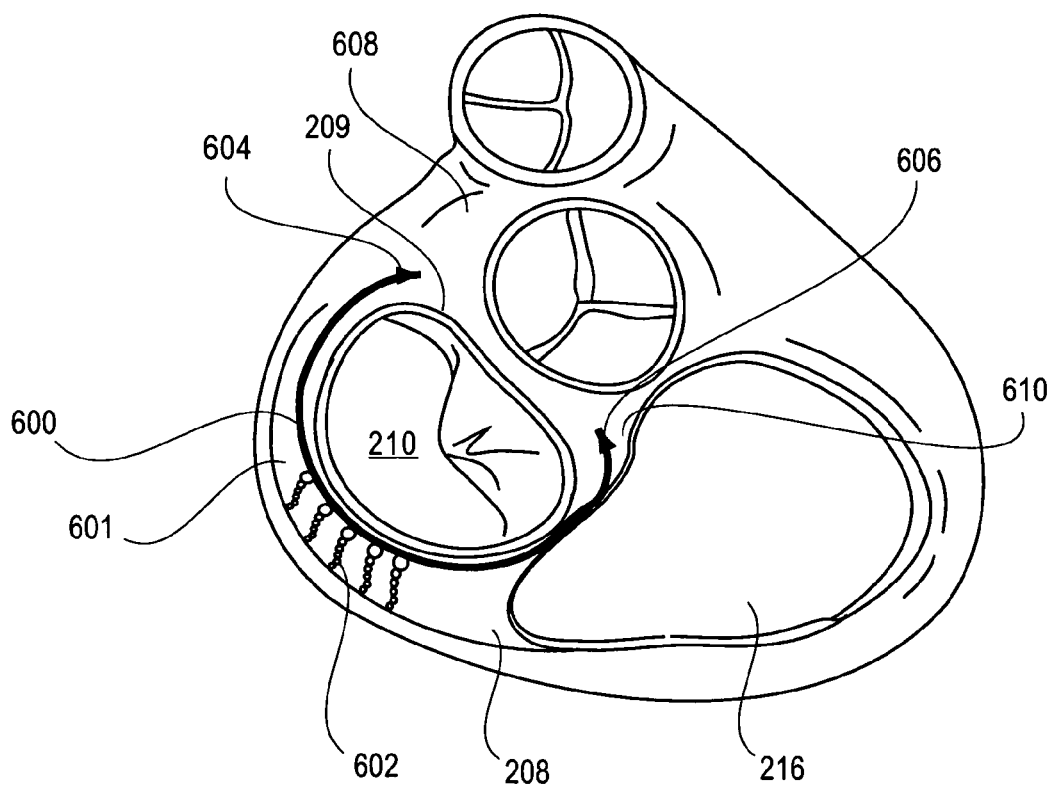
FIG. 29 illustrates an exemplary annuloplasty device deployed within a coronary sinus having anchoring members attached to cardiac tissue proximate the coronary sinus to reduce the curvature of the mitral valve annulus.

FIG. 29 illustrates an exemplary embodiment of an annuloplasty device 601 that comprises a distal anchoring member 604, a proximal anchoring member 606, a ligature 600, and an expandable structure 602. The term ligature is used to include at least a strap, string, cord, wire, bond, thread, suture, backbone, or other connector. The ligature 600 is deployed within the CS 208 along one side of the CS 208 wall. The expandable structure 602 is deployed within the CS 208. The expandable structure 602 may be a stent-like structure that is deployed against the inner diameter of the CS 208. The distal anchoring member 604 anchors into a cardiac tissue that is proximate the CS 208, for example, the left trigone 608. The proximal anchoring member 606 anchors into a cardiac tissue that is proximate the CS 208 and near the entrance 216 of the CS 208, for example, the right trigone 610.

In one embodiment, once the annuloplasty device 601 is fully deployed, the annuloplasty device 601 reshapes the annulus 209 of the mitral valve 208.

Figure 30:
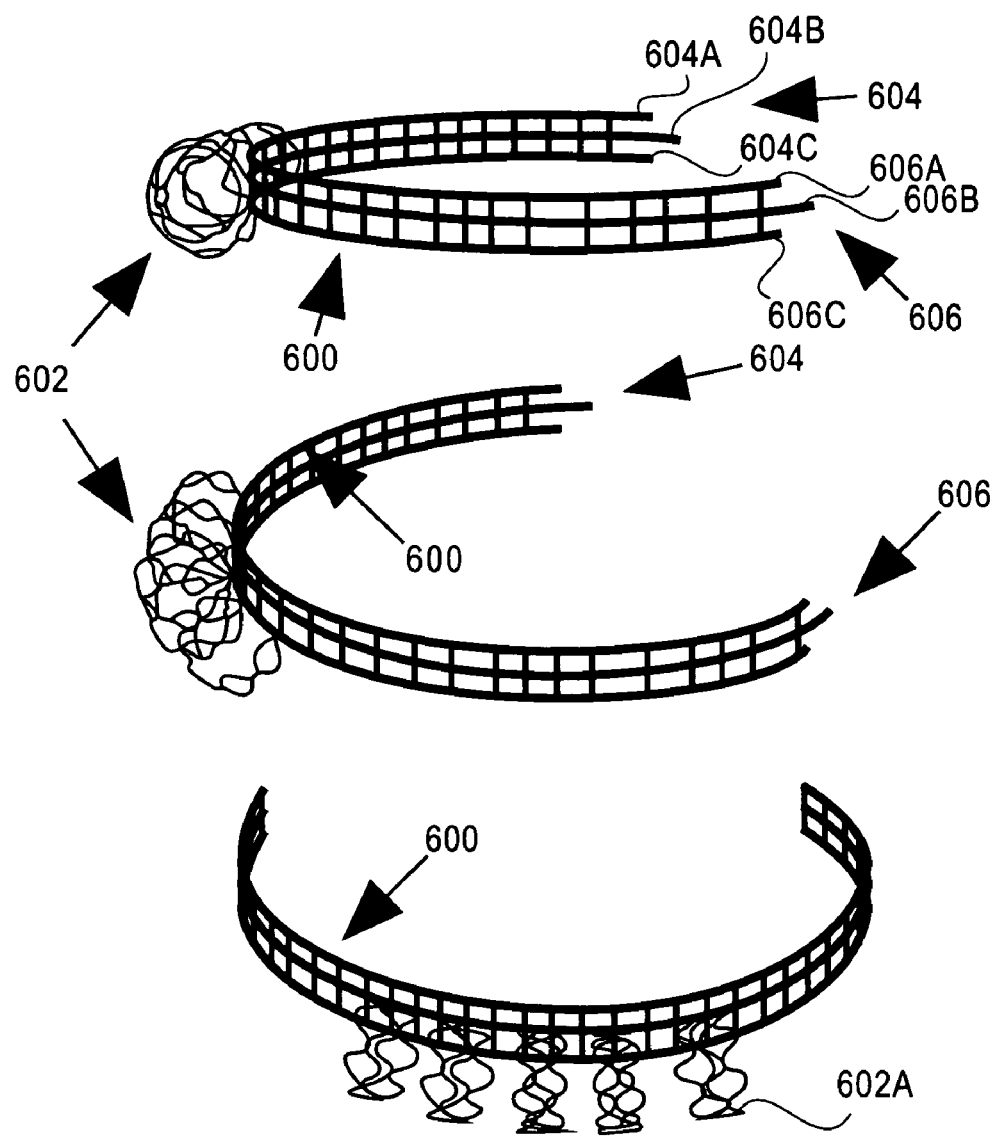
FIG. 30 is an illustration of an exemplary annuloplasty device in accordance with the present invention that can be deployed as shown in FIG. 29.

FIG. 30 illustrates three-dimensional views of the annuloplasty device 601. In one embodiment, the ligature 600 is made of a material that could be manufactured in a specific shape, such as a c-shape. The material could be flexible to allow the ligature to be straightened and held in a straightened conformation by the delivery system that is employed to deliver the annuloplasty device 601 into the CS 208. In another embodiment, the ligature 600 is made of a polymeric material, an elastic material, a shape memory metal or a shrinkable material. In one embodiment, the ligature 600 is made of a material that could be shrunk after it is deployed by an energy source such as IR, RF, an Inductive, UV, or Ultrasound. In yet another embodiment, the ligature 600 is configured to be mechanically shortened such as by folding, bending, or flexing of the structural members of the ligature 600, or by flexing of joins or hinges designed into the ligature 600.

Still referring to FIG. 30, the expandable structure 602 is made of a material that would allow it to be expandable (e.g., by an inflatable balloon) or self-expandable. The expandable structure 602 may also only need to be made of a material that provides only a minimal amount of redial strength. The expandable structure 602 may be deployed against only the inner diameter of the CS 208 but need not hold open the CS 208 such as in the case of a stent used in an angioplasty procedure where the stent is used to open a clogged or closed artery. The expandable structure 602 needs not be rigid, but may be, depending on the application of the annuloplasty device 601. The expandable structure 602 could be made of polymeric materials, flexible materials, shape memory materials or metals. The expandable structure 602 could be made from materials and designs that are used to make conventional stents. The expandable structure 602 may be divided into a plurality of expandable rings 602A to enhance shaping of the CS 208. The expandable structure 602 may include one expandable ring 602A or a plurality of the expandable rings 602A.

In one embodiment, the ligature 600 has a predetermined curvature that is used to reshape the mitral valve annulus 209. The ligature 600 is made of a shaped-memory material that will hold the curvature once the annuloplasty device 601 is deployed. In this embodiment, the expandable structure 602 is capable of maintaining a curvature, for example the predetermined curvature. When the expandable structure 602 is expanded, it adds force or support to maintain or to reinforce the predetermined curvature of the curved ligature 600.

The distal anchoring member 604 and the proximal anchoring member 606 may have configuration of coils, helixes, anchors, hooks, barbs, screws, flanges, and other features that allow the anchoring members to penetrate or attach to a myocardial tissue (or cardiac tissue). It is to be appreciated that each of the distal anchoring members 604 and 606 may include a plurality of anchors. For instance, the distal anchoring member 604 may include three anchors 604a, 604b, and 604c and the proximal anchoring member 606 may include three anchors 606a, 606b, and 606c as shown in FIG. 30.

The ligature 600, the expandable structure 602, the distal anchoring member 604, and the proximal anchoring member 606 may be made from the same material. For example, these structures can be cut out of a tube or a structure and formed into the appropriate configurations. Alternatively, these structures may be laser welded together or otherwise adhered together by using materials such as adhesive or methods well known in the art. The methods of making these structures will be evident to those skilled in the art.

Figure 31:
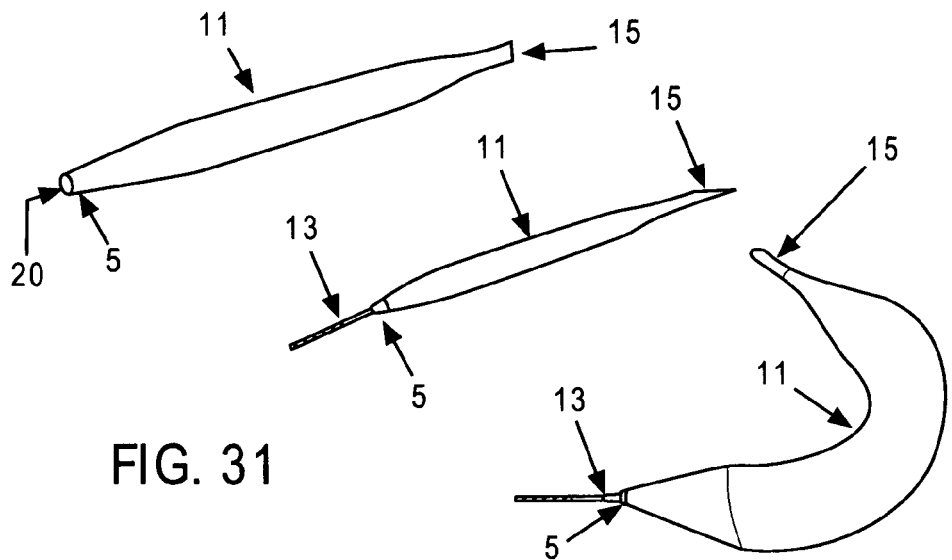
FIGS. 31-33 illustrate exemplary embodiments of a balloon system that can be used to deploy an expandable structure of an annuloplasty device in accordance with the present invention.
Figure 32:
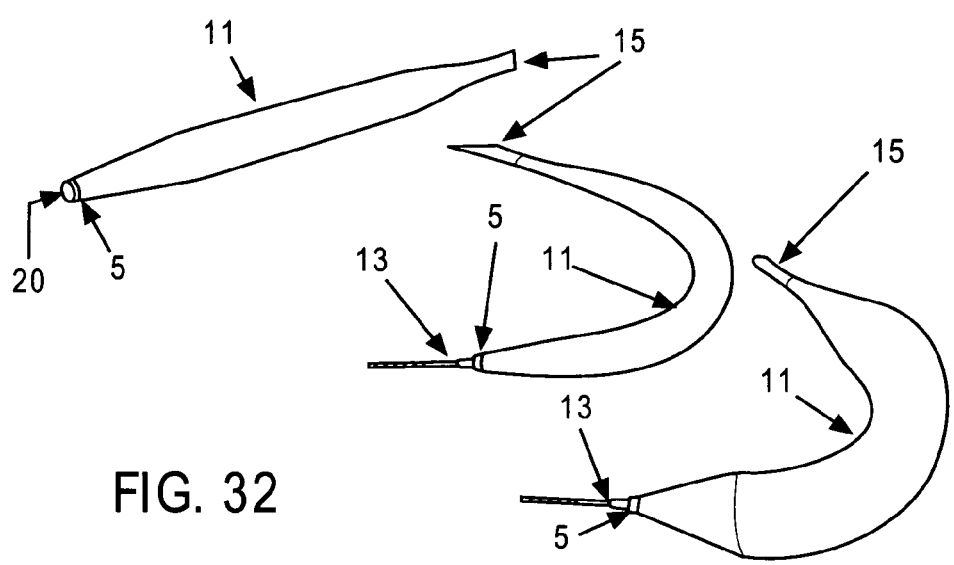
Figure 33:
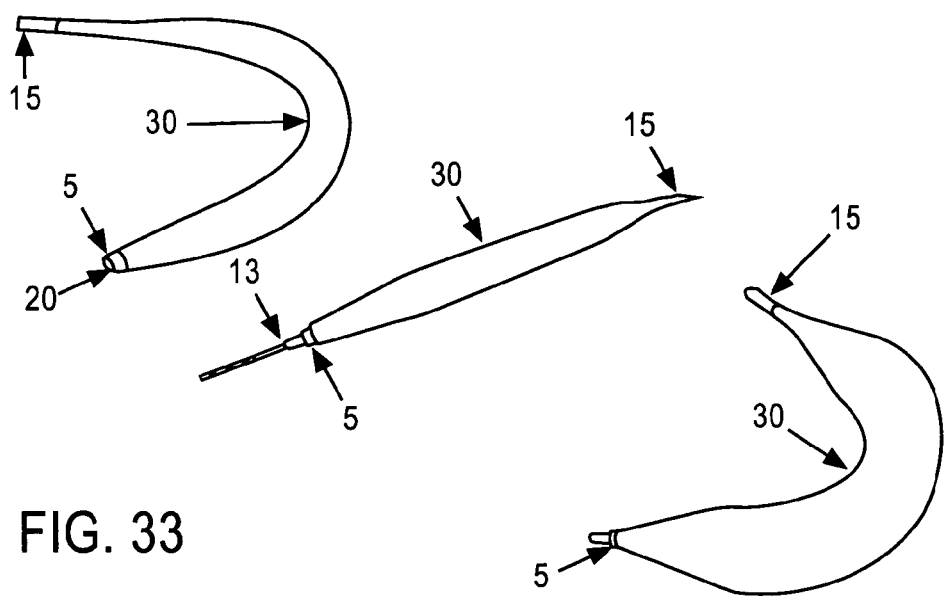

There are several ways of deploying the expandable structure 602 as illustrated in FIGS. 31-33.

In one embodiment, as illustrated in FIG. 31, a balloon 11 is used to expand the expandable structure 602. The balloon 11 includes a distal end 5, a proximal end 15, and a guidewire lumen 20 extending from the distal end 5 to the proximal end 15. A guidewire 13 is disposed in the inner diameter of the guidewire lumen 15. The guidewire 13 is a straight guidewire. The balloon 11 is configured to inflate into a curved balloon upon proper inflation. The balloon 11 has variable thickness along the wall of the balloon 11 thus, upon inflation, the balloon 11 can take on the curved shape. In this embodiment, the expandable structure 602 is disposed on the outside of the balloon 11 and upon inflation, the curved balloon 11 helps expanding the expandable structure 602 into the desired curve and shape.

In one embodiment, as illustrated in FIG. 32, the balloon 11 is used to expand the expandable structure 602. The balloon 11 includes a distal end 5, a proximal end 15, and a guidewire lumen 20 extending from the distal end 5 to the proximal end 15. A guidewire 13 is disposed in the inner diameter of the guidewire lumen 15. The guidewire 13 is a curved guidewire that is shaped to a desired curve that the expandable structure 602 needs to have. As the guidewire 13 is disposed within the balloon 11, the balloon 11 curves as shown in the figure. The balloon 11 is configured to inflate into a curved balloon conforming to the curve of the guidewire 13 upon proper inflation. The balloon 11 has variable thickness along the wall of the balloon 11 to allow the balloon 11 to take the curve of the guidewire 13. In this embodiment, the expandable structure 602 is also disposed on the outside of the balloon 11 and upon inflation, the curved balloon 11 helps expanding the expandable structure 602 into the desired curve and shape.

In one embodiment, as illustrated in FIG. 33, a balloon 30 is used to expand the expandable structure 602. The balloon 30 includes a distal end 5, a proximal end 15, and a guidewire lumen 20 extending from the distal end 5 to the proximal end 15. The balloon 30 is formed to have a curve shape that the expandable structure 602 needs to have. A guidewire 13 is disposed in the inner diameter of the guidewire lumen 15. The guidewire 13 is a straight guidewire that straightens out the curved balloon 30 for easy delivery into the CS 208. As the guidewire 13 is disposed within the balloon 30, the balloon 30 straightens out as shown in the figure. After the balloon 30 is delivered to the proper position for deploying the expandable structure 602, the guidewire 13 is removed and the balloon returns to its original curved shape. Upon a proper inflation, the balloon 30 inflates to expand the expandable structure 602. The balloon 30 has variable thickness along the wall of the balloon 30 to allow the balloon 30 to have the curved shape. The balloon 30 may also be made of shape-memory material or may include a tension strap that will help returning the balloon 30 to the curved shape after the guidewire 13 is withdrawn. In this embodiment, the expandable structure 602 is also disposed on the outside of the balloon 30 and upon inflation, the curved balloon 30 helps expanding the expandable structure 602 into the desired curve and shape.

Figure 34:
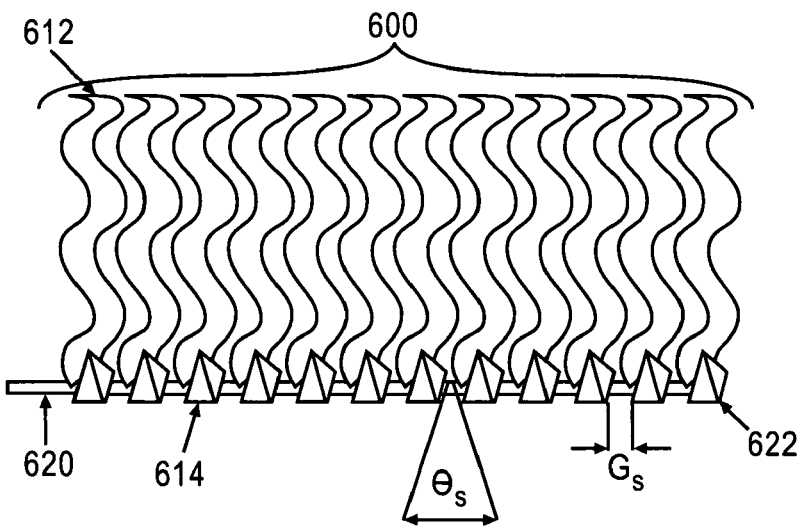
FIGS. 34-36 illustrate exemplary embodiments of an expandable structure of an annuloplasty device in accordance with the present invention.
Figure 35:
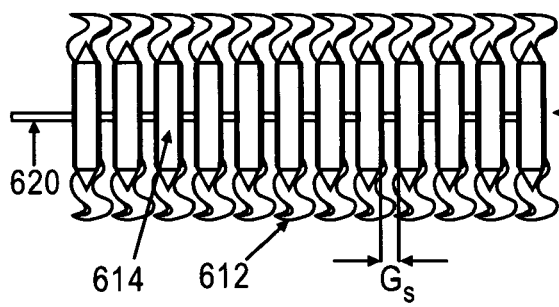
Figure 36:
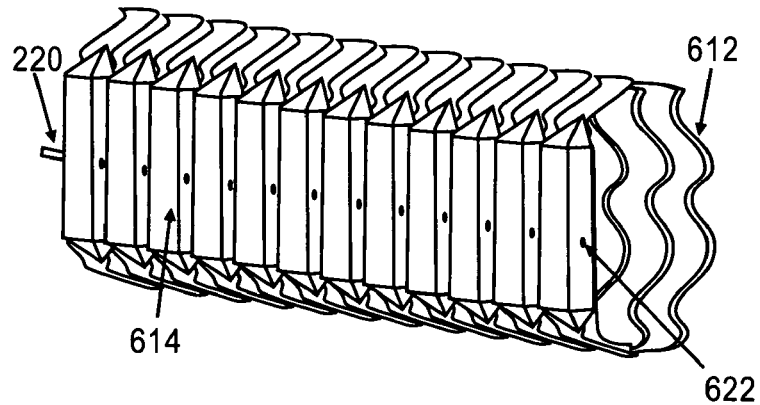

FIGS. 34-36 illustrate exemplary configuration of the expandable structure 602. The expandable structure 602 comprises of a series of expandable rings 612 having wave-like shape or sinusoidal shape in their unexpanded state. The expandable rings 612 are held together by a tension mechanism 620. The tension mechanism 620 is made of a shaped-memory material that allows the tension mechanism 620 to have a predetermined curvature. The predetermined curvature is configured to force the expandable structure 602 to conform to the curvature. In one embodiment, the predetermined curvature has the curvature of the CS 208. In one embodiment, the tension mechanism 620 is a filament or a backbone that is inserted through an aperture 622 created in each of the expandable rings 612. Each of the expandable rings 612 includes a portion 614 that includes a flat surface in one embodiment. A distance $G_s$ separates one portion 614 of one ring 612 from another portion 614 of another ring 612. An angle $\theta_s$ separates one portion 614 of one ring 612 from another portion 614 of another ring 612.

Figure 37A:
FIGS. 37A-37C illustrate exemplary embodiments of the expandable structure shown in FIGS. 34-36 with curvature.
Figure 37B:
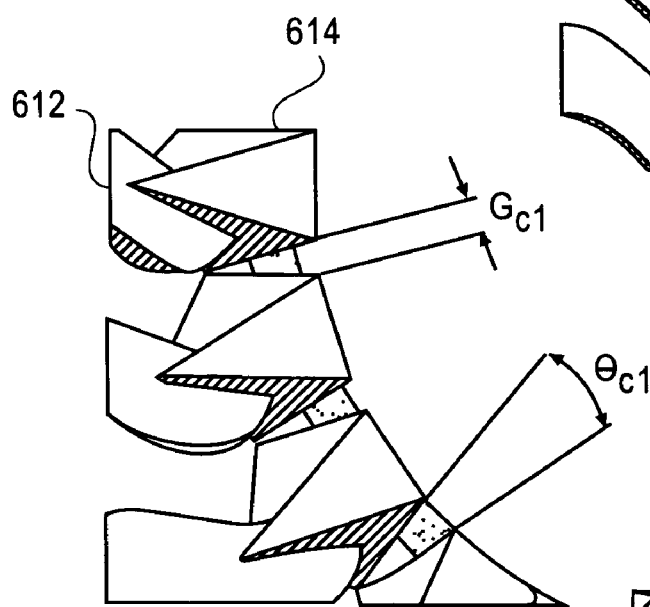

In one embodiment, tension is applied to the tension mechanism 620, which causes the expandable structure 602 to bend in a curved fashion. In one embodiment, the expandable structure 602 is curved to a shape and size and that is desirable for reforming, reshaping, or reducing the annulus 209 of the mitral valve 210. As shown in FIGS. 37A-37C and FIGS. 38-39, as tension is applied to the tension mechanism 620, the tension mechanism 620 pulls the rings 612 closer to each other on the sides of the rings 612 that include the tension mechanism 620. The expandable structure 602 is brought to the curved shape as the tension mechanism 620 works to pull the expandable rings 612 closer to each other. Because tension is only applied on one side of each of the expandable rings 612 by the tension mechanism 620, the expandable structure 602 curves toward that side. As shown in FIG. 37A, when the expandable structure 602 is in a non-curved shape, the distance $G_s$ between each expandable ring 612 at the portion 614 is larger than the distance $G_{c1}$ between each expandable ring 612 in a curved shape ($G_{c1} < G_s$) as shown in FIG. 37B.

Figure 37C:
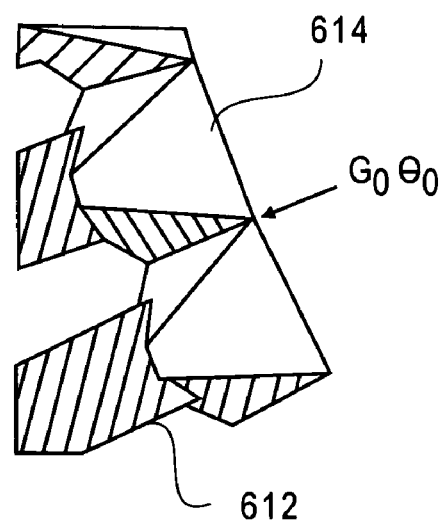

In one embodiment, as shown in FIGS. 37A-37C, when the expandable structure 602 is in a non-curved shape, the angle $\theta_s$ between each expandable ring 612 at the portion 614 is larger than the angle $\theta_{c1}$ between each expandable ring 612 in a curved shape ($\theta_{c1} < \theta_s$). And, in another embodiment, as shown in FIG. 37C, as the tension mechanism 620 applies enough tension, the expandable structure 602 is in its most curved state wherein the distance and angle between each expandable rings 612 at portions 614 is near zero "0." In this configuration, every expandable ring 612 is positioned adjacent to the next ring with no distance between them.

Figure 38:
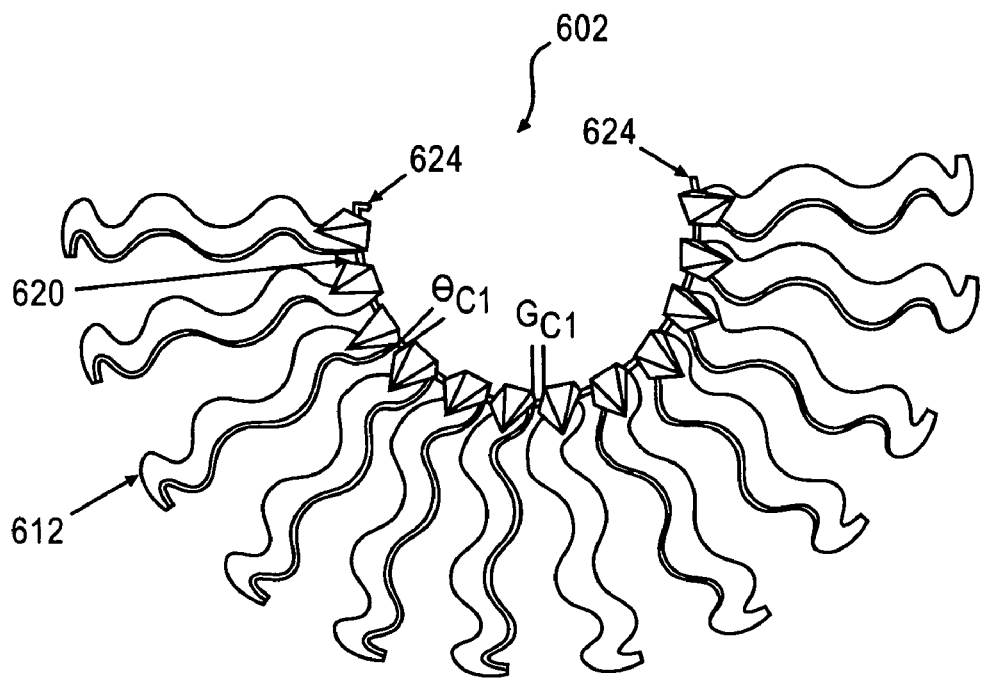
FIGS. 38-39 illustrate exemplary embodiments of the expandable structure shown in FIGS. 34-36 with curvature.
Figure 39:
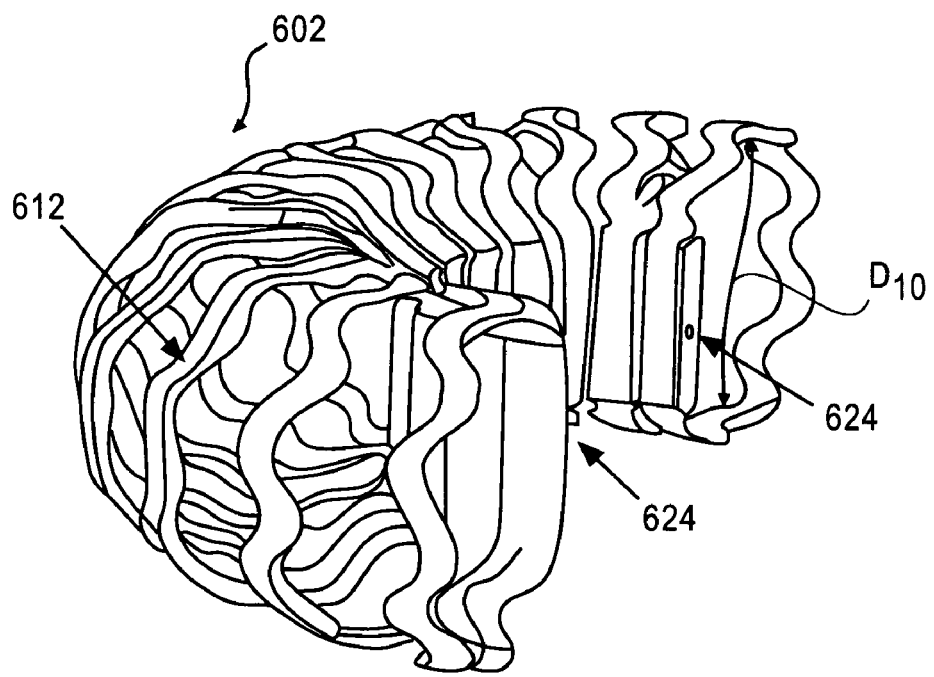

FIGS. 38-39 illustrate other perspective views of the expandable structure 602 in its curved position. In one embodiment, the expandable rings 612 are not yet fully expanded at this point. These figures also show that the expandable structure 602 includes sealing members 624 located at the end of the tension mechanism 620 to keep the expandable rings 612 from being detached from each other.

Figure 40:
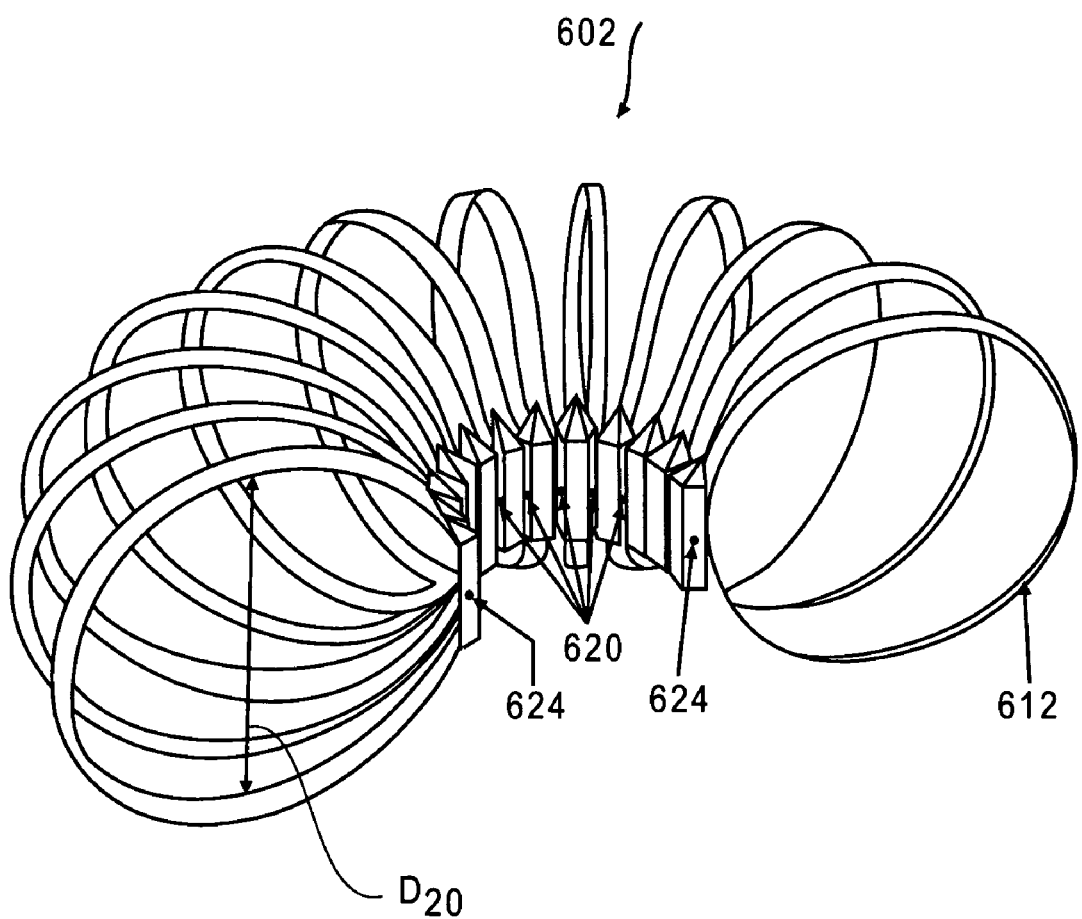
FIG. 40 illustrates an exemplary embodiment of the expandable structure shown in FIGS. 38-39 in a fully expanded state.

FIG. 40 illustrates the expandable rings 612 in their fully expanded state. In one embodiment, the rings 612 are fully expanded to have the shape of circular rings. When the rings 612 are fully expanded, each of the rings 612 has a diameter $D_{20}$ that is greater than the diameter $D_{10}$ of each ring 612 when they are not fully expanded as shown in FIG. 39. In other embodiments, the rings 612 can be fully expanded to have shapes such as oval, oblong, or rings with wave-like shapes.

Figure 41:
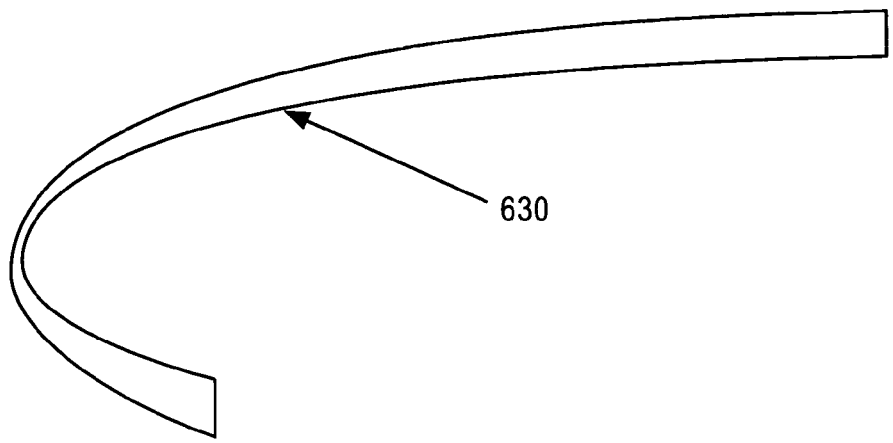
FIG. 41 illustrates an exemplary embodiment of a backbone that can be used to form the curvature for the expandable structure.
Figure 42:
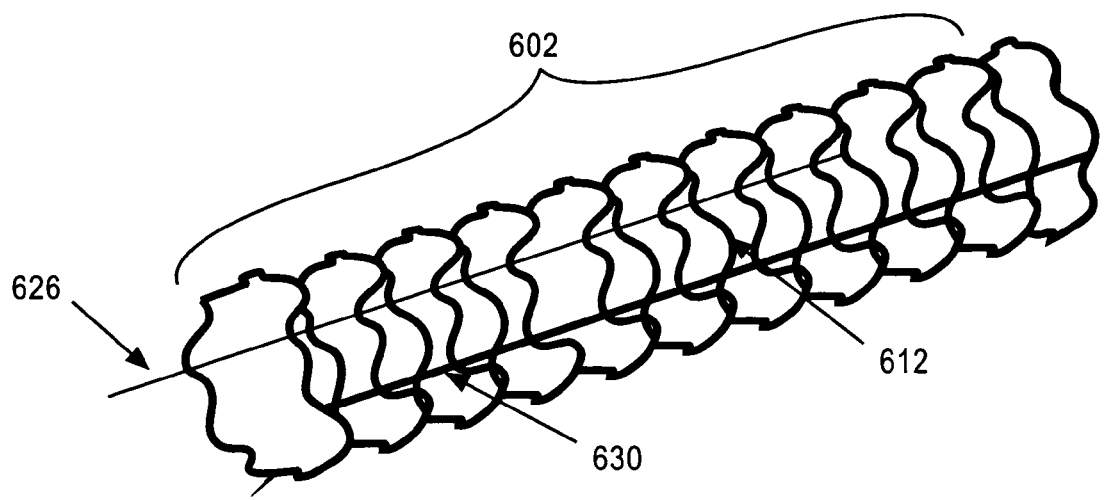
FIG. 42 illustrates an exemplary embodiment of a straightening device that can be used to temporarily straighten out the expandable structure during deployment.

In one embodiment, to provide the expandable structure 602 with a curve shape, a curved-shape backbone 630 shown in FIG. 41 is used. In one embodiment, the curved-shape backbone 630 is a shaped-memory structure that has a natural curve shape that conforms to the curve of the CS 208. As shown in FIG. 42, the backbone 630 is first coupled to one side of the expandable structure 602. Coupling the backbone 630 to the expandable structure 602 will cause the expandable structure 602 to take on the curved shape of the backbone 630. In this embodiment, the backbone 630 may replace the tension mechanism 620 of the embodiments shown in FIGS. 34-39. In order to deploy the expandable structure 602 into the CS 808, the expandable structure 602 is temporarily straightened so that the expandable structure 602 can fit into a conventional delivery device (e.g., a balloon on a catheter). As shown in FIG. 42, a straightening wire 626 is disposed within the inner diameter of the expandable structure 602. Each of the rings 612 may have a groove, a slot, or an aperture on one side where the straightening wire 626 can be disposed therethrough. The expandable structure 602 is thus temporarily straightened. The expandable structure 602 of this embodiment can be deployed and expanded with a balloon. Exemplary embodiments of the balloon delivery system that can be used include the embodiments shown in FIGS. 31 and 33.

Figure 43:
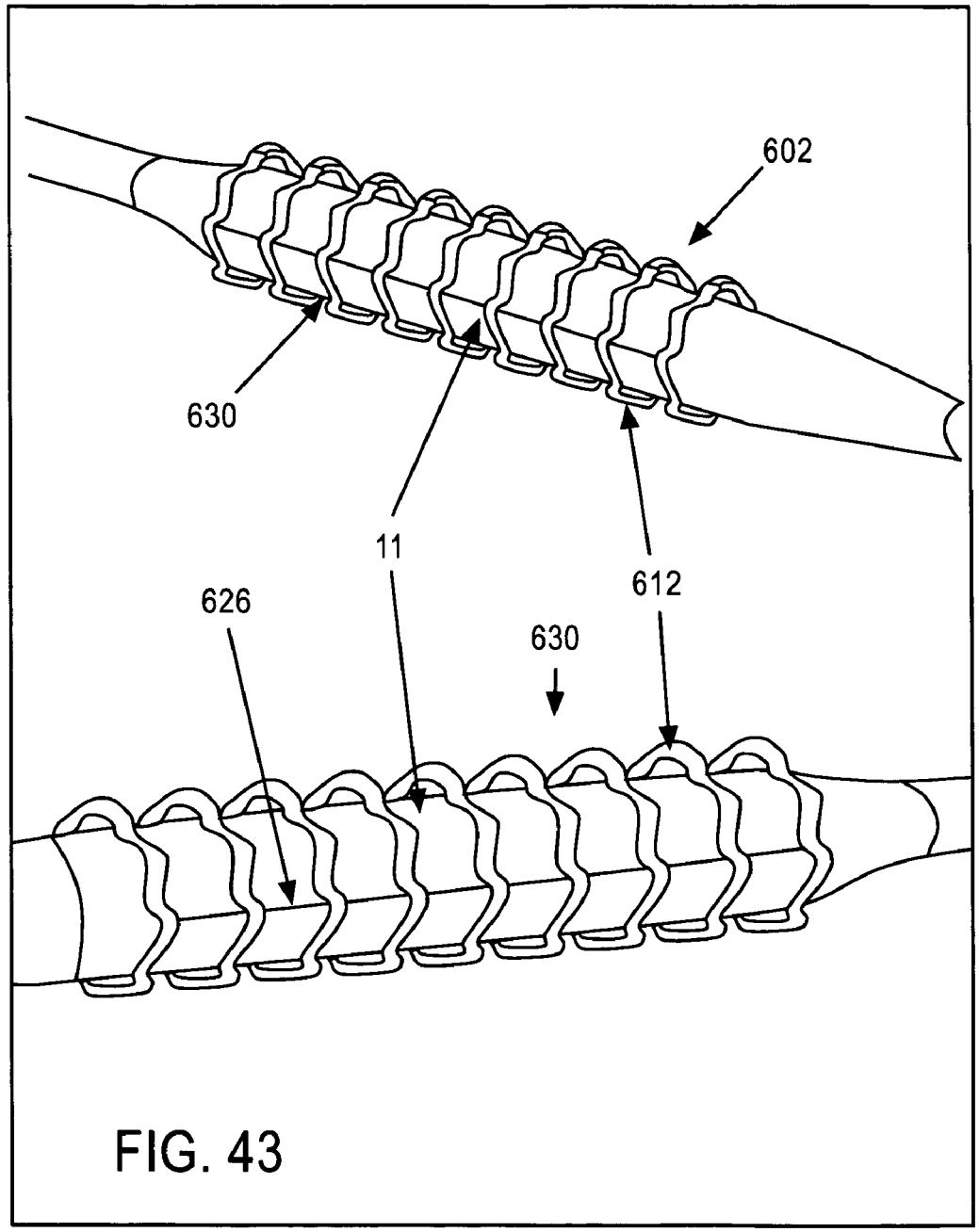
FIGS. 43-45 illustrate a balloon system that can be used to deploy the expandable structure.

In one embodiment, as shown in FIG. 43, a curved expandable structure 602 (e.g., as curved by the backbone 630 or by the tension mechanism 620) that is temporarily straightened with a straightening wire 626 is disposed on the outer diameter of a balloon 11. The balloon 11 is "passive" and will take the curve shape of the curved expandable structure 602 when the straightening wire 626 is removed after the curved expandable structure 602 is delivered to the inner diameter of the CS 208.

Figure 44:
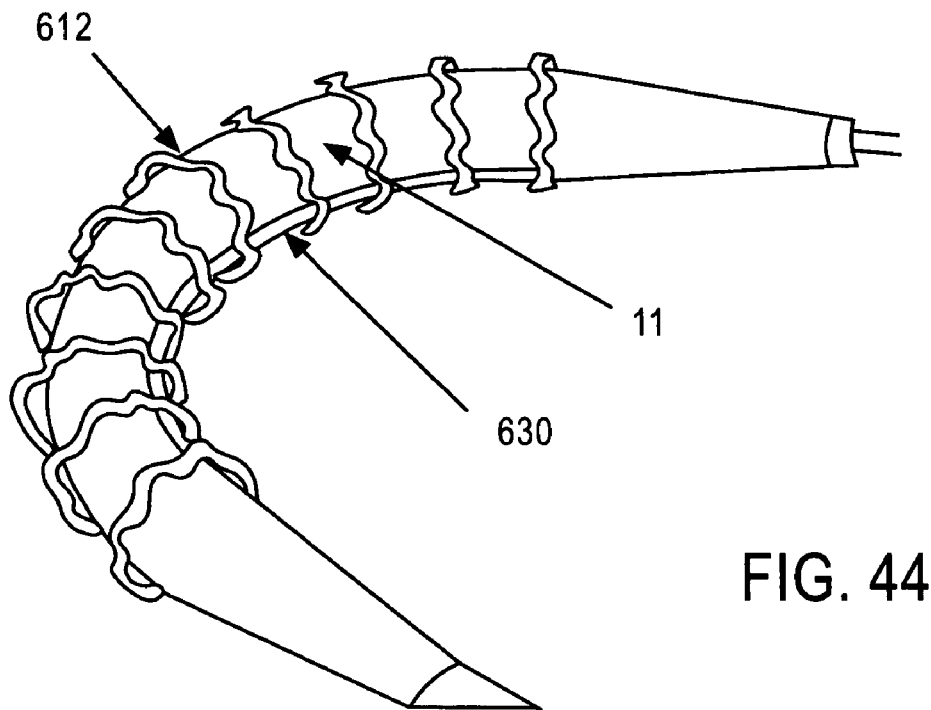
Figure 45:
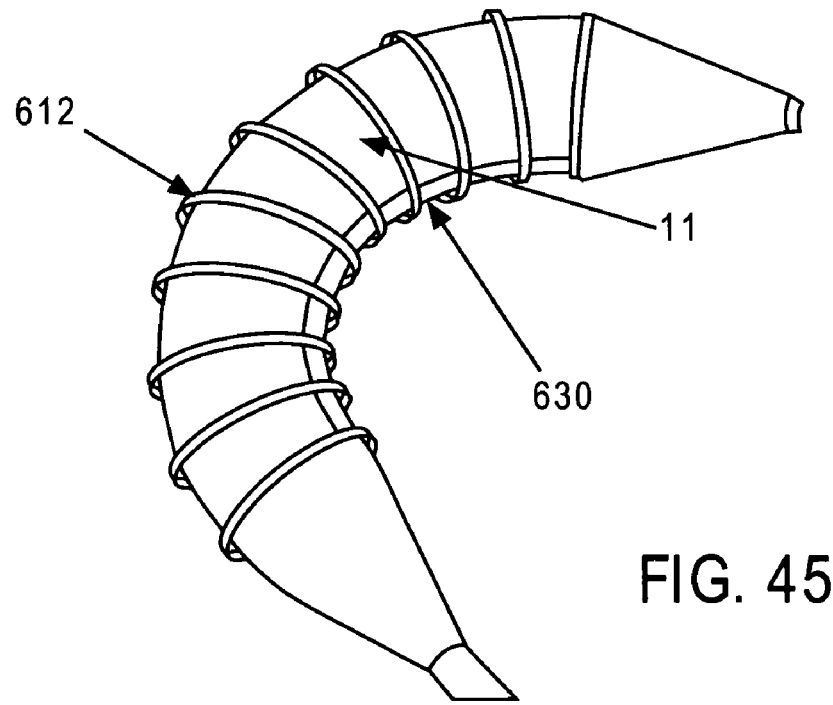

FIG. 44 illustrate the curved expandable structure 602 after it is delivered to the inner diameter of the CS 208 and the straightening wire 626 is removed. The curved expandable structure 602 is shown to return to the curve shape, and in this figure, that is conforming to the curve shape of the curved shape backbone 630. FIG. 45 illustrates an example of the curved expandable structure 602 in its fully expanded state as the balloon 11 is inflated by conventional methods. The balloon is then deflated, leaving the curved expandable supporting structure in place to reshape the CS 208.

Figure 46:
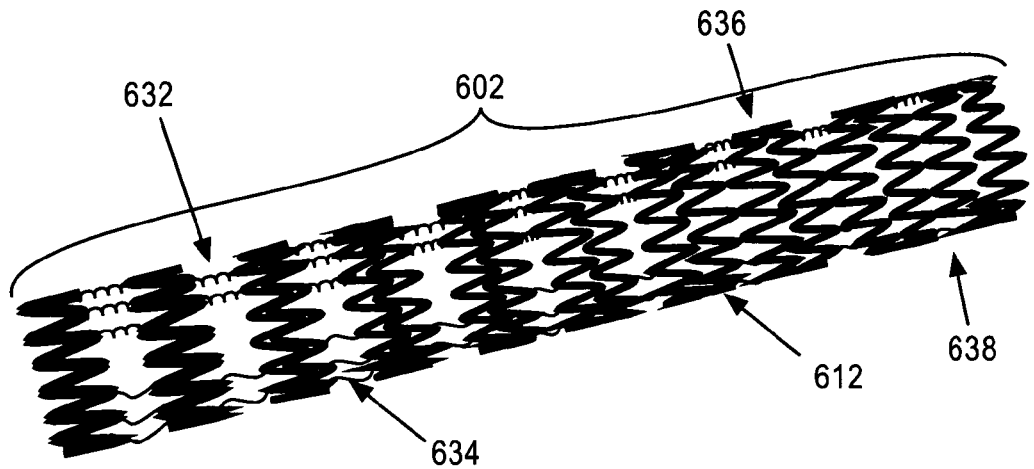
FIGS. 46-50 illustrate exemplary embodiments of an expandable structure that can be made to curve to one side.
Figure 47:
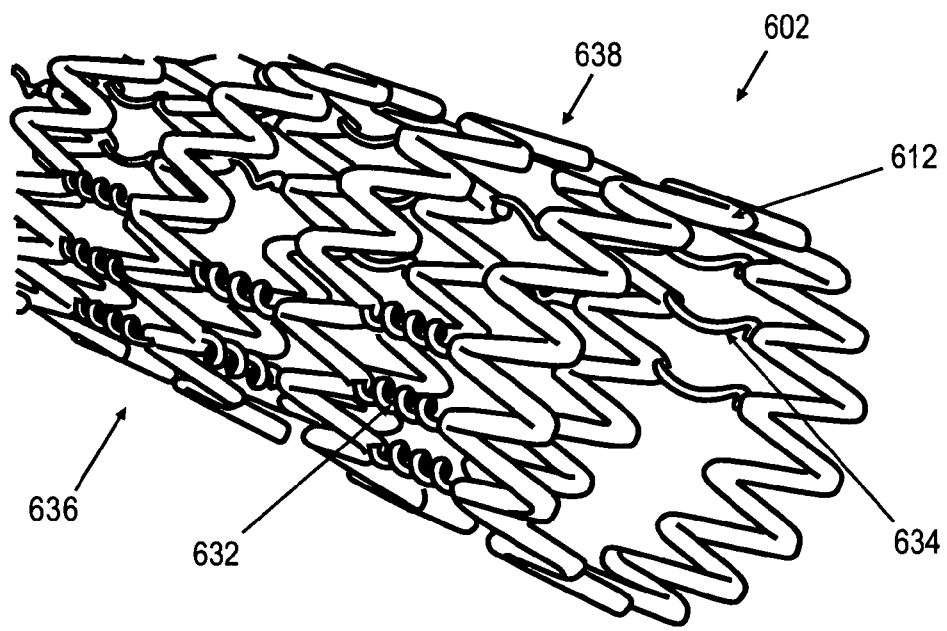

In one embodiment, to provide the expandable structure 602 with a curve shape, various links of various linear lengths are used to hold the expandable rings 612 together as shown in FIGS. 46-47. Using links of different linear lengths would expand the expandable structure 602 into a curved structure such that one side can curve in more than the other.

In one embodiment, the various links with different linear lengths include a plurality of coiled/helical links 632 and a plurality of coiled/helical links 634. The coiled/helical links 632 and 634 are similar except that one may have more coils, turns, or period per unit length than the other. In one embodiment, the coiled/helical links 632 is a coiled structure that has more turns, coils, and periods per unit length than that of the coiled/helical links 634. For example, the coiled/helical links 632 has four turns while the coiled/helical links 634 has only 1 turn. The coiled/helical links 634 has fewer curves and no turn. The coiled/helical links 632 has a longer linear length than the coiled/helical links 634 when the coiled/helical links 632 is stretched.

The plurality of coiled/helical links 632 is placed the side 636 of the expandable structure 602 to connect one ring 612 to another ring 612. The plurality of coiled/helical links 634 is place on the side 638 that is opposite the side 636.

Figure 48:
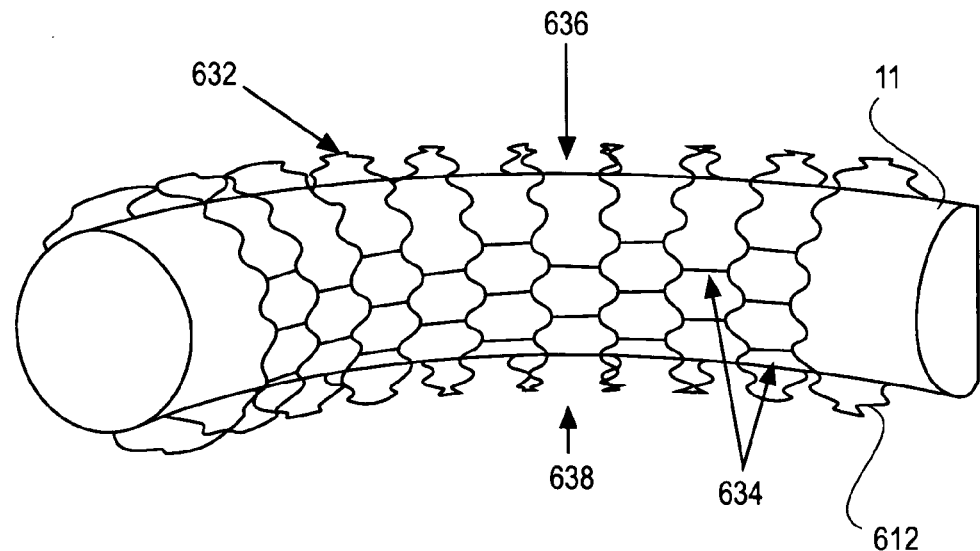
Figure 49:
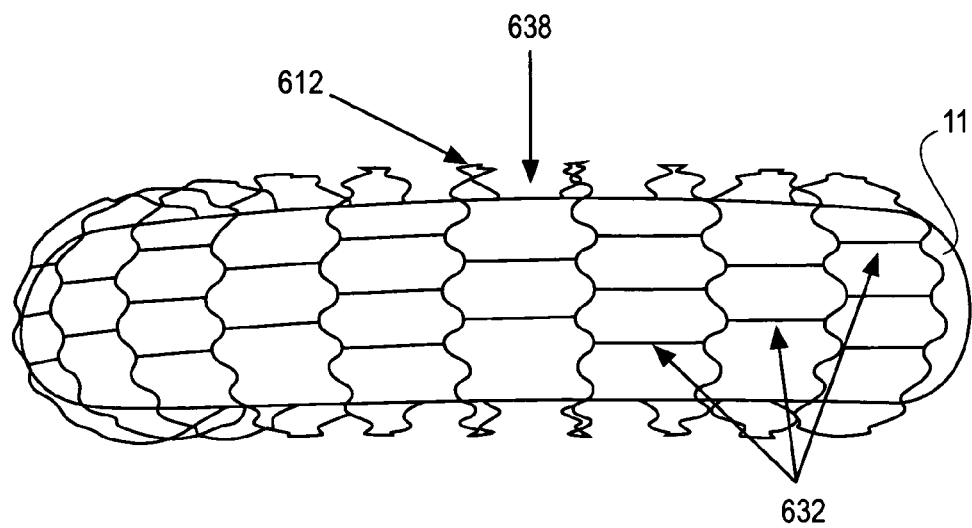

When expanded (or stretched) the lengths on the side 636 and the side 638 are different due to the difference in the linear lengths. The side 638 is shorter than the side 636 thus, the expandable structure 602 is curved toward the side 638 as shown in FIGS. 48-49. The expandable structure 602 with this configuration can be deployed in the CS 208 using method previously described (e.g., see FIG. 43).

In one embodiment, the coiled/helical links 632 and 634 shown in FIGS. 46-49 may have the same configurations (not shown). Both the coiled/helical links 632 and 634 may have the same number of coils, periods, or turns and essentially, the same linear length. Each of the coiled/helical links 632 and 634 is made of a different material or a material having a different tension property. Each of the coiled/helical links 632 and 634 thus has a different tension strength from each other. When the same force is used to expand the expandable structure 602, the sides of the expandable structure 602 expands differently. For example, the side 638 may have the coiled/helical links 632 that is made of a thicker material that has a higher tension strength while the side 636 may have the coiled/helical links 634 that is made of a thinner material that has a lower tension strength. When expanded, the expandable structure 602 curves toward the side 638.

Figure 50:
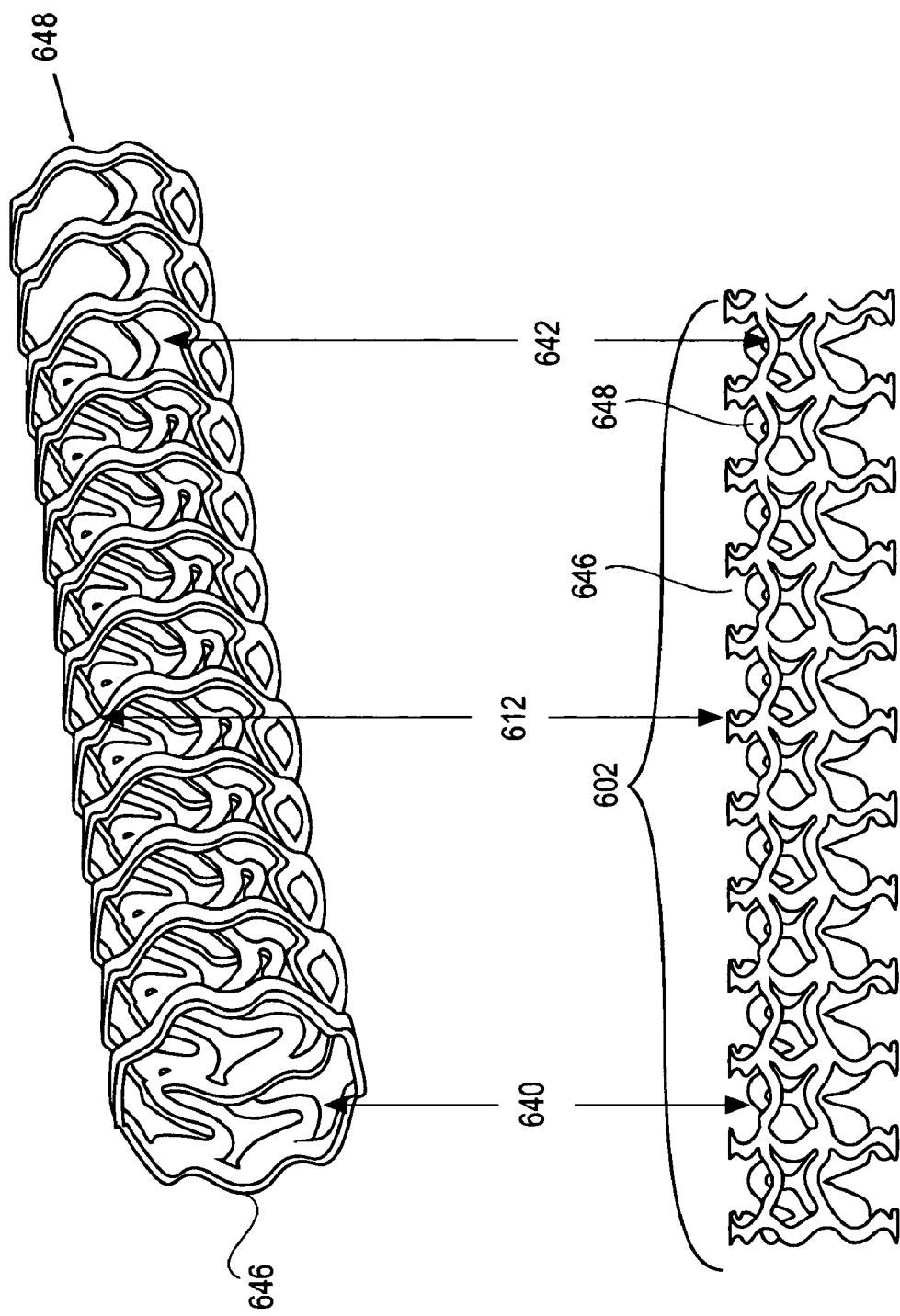

In one embodiment, to provide the expandable structure 602 with a curve shape, wave-like links of different linear lengths are used to hold the expandable rings 612 together as shown in FIG. 50. The expandable rings 612 are held together by a first plurality of wave-like links 640 and a second plurality of wave-like links 642. The first plurality of wave-like links 640 is placed on the side 646 of the expandable structure 602. The second plurality of wave-like links 642 is placed on the side 648 of the expandable structure 602.

Each of the first plurality of wave-like links 640 has a fully stretched length that is longer than each of the second plurality of wave-like links 642. Each of the first plurality of wave-like links 640 includes more sinusoidal waves than each of the second plurality of wave-like links 642. Alternatively, each of the first plurality of wave-like links 640 has greater linear length along the path between two links than each of the second plurality of wave-like links 642. When the rings 612 are held together by these two different lengths of links, 640 and 642, the expandable structure 602 curves toward the side 648 where the links 642 are shorter. The expandable structure 602 with this configuration can be deployed in the CS 208 using a method previously described (e.g., see FIG. 43).

In one embodiment, the links 640 and 642 shown in FIG. 50 may have the same configurations (not shown). Each of the links 640 and 642 is made of a different material or a material having a different tension property. Each of the links 640 and 642 thus has a different tension strength from each other. When the same force is used to expand the expandable structure 602, the sides of the expandable structure 602 expands differently. For example, the side 648 may have the links 642 that is made of a thicker material that has a higher tension strength while the side 646 may have the links 640 that is made of a thinner material that has a lower tension strength. When expanded, the expandable structure 602 curves toward the side 648.

Figure 51:
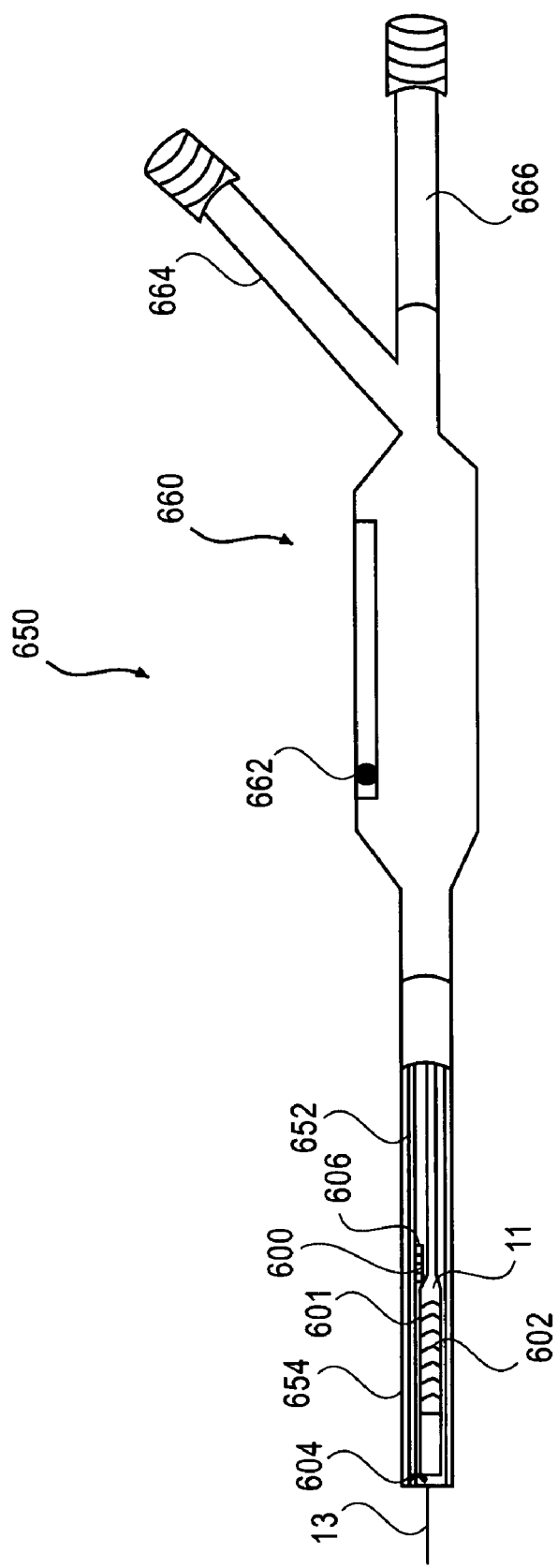
FIG. 51 illustrates an exemplary embodiment of a delivery device that can be used to deliver an exemplary annuloplasty device of the present invention.

FIG. 51 illustrates an exemplary delivery device 650 that can be used to deliver the annuloplasty device 601 that includes the expandable structure 602 and the ligature 600 to the CS 208 to reshape the annulus 209 of the mitral valve 210. The delivery device 650 is one type of a rapid exchange catheter well known in the art. It is to be understood that other methods can be used to deliver the annuloplasty device 601 without departing from the scope of the present invention.

The delivery device 650 includes an expandable balloon 11 for deploying the annuloplasty device 601 which resides in the CS 208 (not shown here but see FIG. 29). The delivery device 650 further includes a guidewire 13 to guide portion (the distal portion) of the delivery device 650 into the CS 208. As shown in FIG. 51, the annuloplasty 601 comprising the ligature 600 couples to an expandable structure 602, a distal anchoring member 604, and a proximal anchoring member 606 are disposed within the delivery device 650. In one embodiment, the annuloplasty device 601 as described above is disposed within a protective sheath 652 of the delivery device 650. In one embodiment, the distal anchoring member 604 anchors into the left trigone and the proximal anchoring member 606 anchors into the right trigone.

In one embodiment, the delivery device 650 further includes handle section 660 located proximally of the delivery device 650. The delivery device 650 includes a retracting mechanism 662 for retracting the protective sheath 652. The delivery device 650 includes a port 664 for pressurizing a lumen of the delivery device 650 that communicates with the lumen of the inflatable balloon 12. The port 664 thus enables the balloon 12 to be inflated, for example by pressure or fluid. The delivery device 650 includes a port 666 that allows access to the guidewire lumen of the delivery device 650 for the guidewire 13 to pass through. The port 666 also enables control of the guidewire 13 as the guidewire 13 is advanced into the CS 208.

In one embodiment, the guidewire 13 is inserted into a vein the body of a patient through an introducer (not shown) as is well known in the art. A guide catheter 654 is placed over the guidewire 13 through the introducer into the vessel lumen (the vein). The guidewire 13 and the guide catheter 654 are advanced through the vessel to the right atrium and into the coronary sinus. The annuloplasty device 601 within the protective sheath 652 is then loaded on or over the guidewire 13 and within the inner diameter of the guide catheter 654 and delivered to a location in the CS 208 adjacent to the mitral valve 210. The protective sheath 652 is then retracted slightly and proximally relative to the annuloplasty device 601 to expose the distal anchoring member 604. The distal anchoring member 604 is then inserted or anchored into the left trigone. The protective sheath 652 is further retracted proximally to expose the proximal anchoring component 606. The proximal anchoring component 606 is inserted anchored into the right trigone. At this point, the ligature 600 is deployed within the CS 208. The expandable balloon 11 is then inflated to deploy the expandable structure 602 in the inner diameter of the CS 208. In one embodiment, the expandable structure 602 is deployed against the inner diameter of the CS 208. The expandable structure 602 thus ensures that CS 208 stays open and unobstructed by the annuloplasty device 601. The expandable structure 602 does not necessarily function in opening up the CS 208.

In one embodiment, the distal end portion of the protective sheath 652 may contain a slit or cutaway section (not shown) to allow the protective sheath 652 to expand an opening, which will slide over the annuloplasty device 601 as the protective sheath 652 is retracted during deployment.

In one embodiment, the protective sheath 652 also acts as a straightening device (replacing the need for the straightening wire 626) to temporarily straighten the expandable structure 602 during delivery and deployment. The protective sheath 652 also acts as a straightening device to temporarily straighten the ligature 600. Once the ligature 600 and the expandable structure 602 is placed in the CS 208, the withdrawal of the protective sheath 652 allows the expandable structure 602 that is curved to conform or return to a particular curve to return to its curved shape. In another embodiment, once fully deployed, the expandable structure 602 acts to maintain or support the curvature of the ligature 600.

After the annuloplasty device 601 is fully deployed, the ligature 600 and the expandable structure 602 is fully deployed within the CS 208, the distal anchoring member 604 anchored into an area in the left trigone, and the proximal anchoring member 606 anchored into an area in the right trigone. In one embodiment, the ligature 600 is pressed against the inner wall of the CS 208 on the side that faces the mitral valve annulus 209. In one embodiment, the curvature of the ligature 600 reshapes the size of the mitral annulus 209. In one embodiment, the curvature of the ligature 600 together with the curvature of the expandable structure 602 reshapes the size of the mitral annulus 209.

It is to be understood that the delivery device 650 can be made from materials and designs similar to current stent delivery systems. The delivery device 650 could be of the over-the-wire or rapid-exchange styles of stent delivery systems as known in the art. The delivery device 650 also could include materials or be made of materials that are compatible with X-ray, ultra sound of Magnetic Resonance Imaging (MRI) methods for the purpose of visualizing the delivery, placement and deployment of the annuloplasty device 601.

Figure 52:
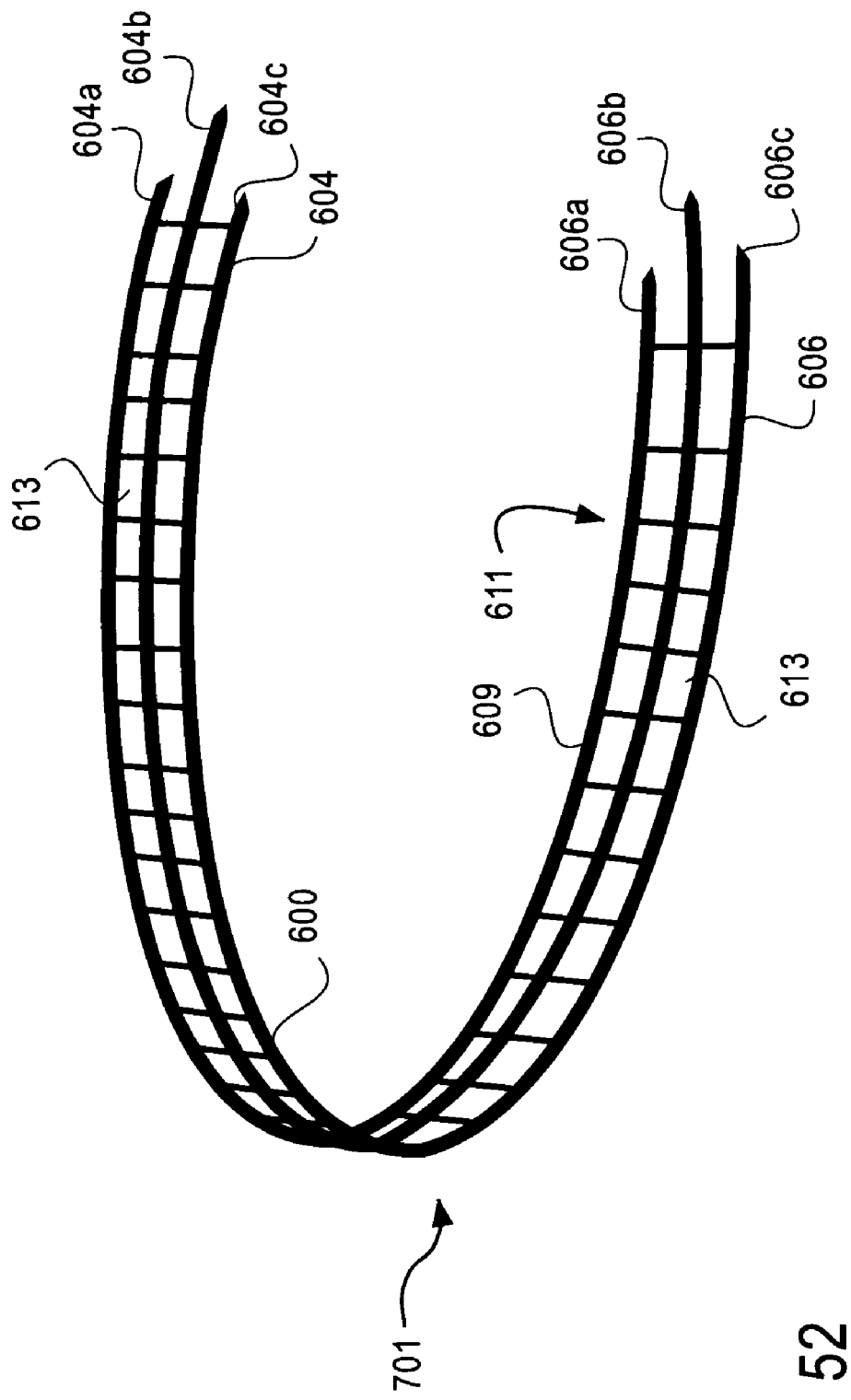
FIG. 52 illustrates an exemplary embodiment of an annuloplasty device of the present invention.

FIG. 52 illustrate an exemplary annuloplasty device 701 which can be deployed in the CS 208 to reshape the mitral valve annulus 209. The annuloplasty device 701 is similar to the annuloplasty device 601 previously described. The annuloplasty device 701 however does not include the expandable structure 602.

Similar to the annuloplasty device 601, the annuloplasty device 701 includes a ligature 600, a distal anchoring member 604 and a proximal anchoring member 606 which may be coils, helixes, anchors, hooks, barbs, screws, flanges, and other feature that allow the anchoring members to penetrate and attach to a myocardial tissue (or cardiac tissue). Again, it is to be appreciated that each of the distal anchoring member 604 and 606 may include a plurality of anchors. For instance, the distal anchoring member 604 may include three anchors 604a, 604b, and 604c and the proximal anchoring member 606 may include three anchors 606a, 606b, and 606c. In one embodiment, the ligature 600 extends into the distal anchoring member 604 and the proximal anchoring member 606. In other words, the ligature 600, the distal anchoring member 604, and the proximal anchoring member 606 are made of the same piece.

The ligature 600 is sufficient sized to have a surface area that will prevent the ligature 600 from cutting through the wall of the blood vessel (e.g., the CS 208) once the distal anchoring member 604 and the proximal anchoring member 606 are deployed. In one embodiment, the ligature 600 includes a flat and wide surface 609 and/or a flat and wide surface 611. One of these surfaces (609 and 611) is the side that is in immediate contact with the inner wall of the CS 208, for example, the surface 611 is deployed to be in immediate contact with the inner wall of the Cs 208. Since the surface 611 is sufficiently wide and flat, the ligature 600 is prevented from cutting through the wall of the CS 208.

In one embodiment, the ligature 600 includes a plurality of openings 613 created into the ligature 600. In one embodiment, the openings 613 facilitate the anchoring of the ligature 600 onto the inner wall of the CS 208.

Figure 53:
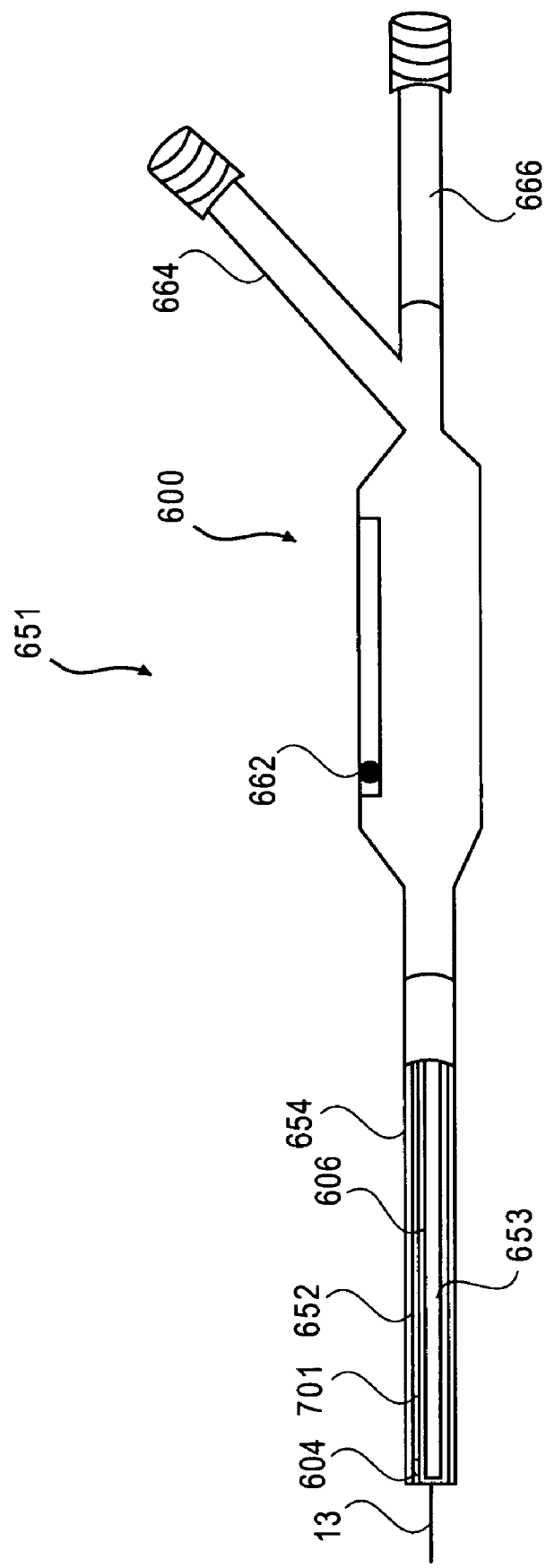
FIG. 53 illustrates an exemplary embodiment of a delivery device that can be used to deliver an exemplary annuloplasty device of the present invention.

All other aspects of the annuloplasty device 701 are similar to the annuloplasty device 601. The annuloplasty device 701 can be deployed using a delivery catheter 651 illustrated in FIG. 53. The delivery catheter 651 is similar to the delivery catheter 650 previously described with the addition of an inner sheath 653. The delivery device 651 can be a type of a rapid exchange catheter well known in the art. It is to be understood that other methods can be used to deliver the annuloplasty device 701 without departing from the scope of the present invention.

Figure 54A:
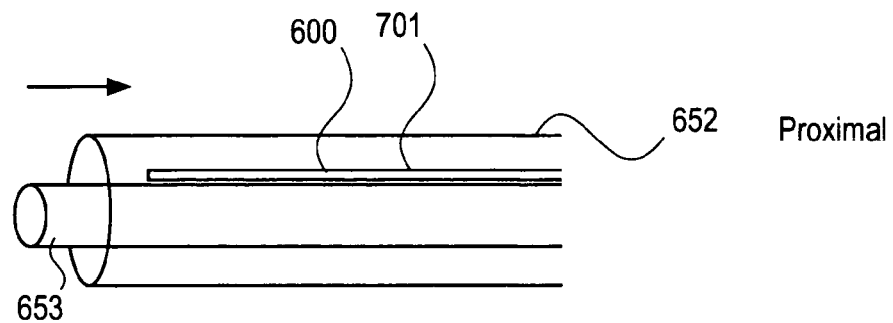
FIGS. 54A-54D illustrate how an exemplary annuloplasty device of the present invention can be deployed.
Figure 54B:
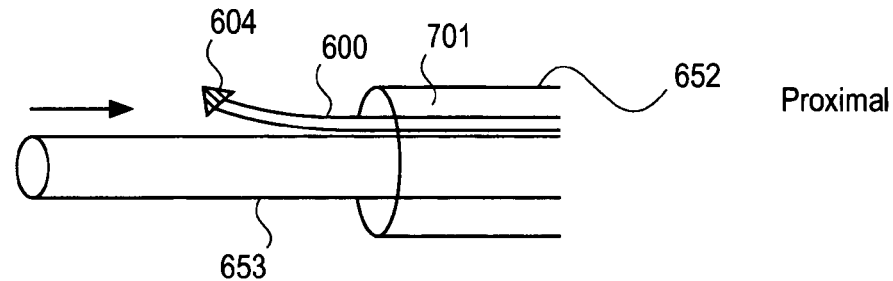
Figure 54C:
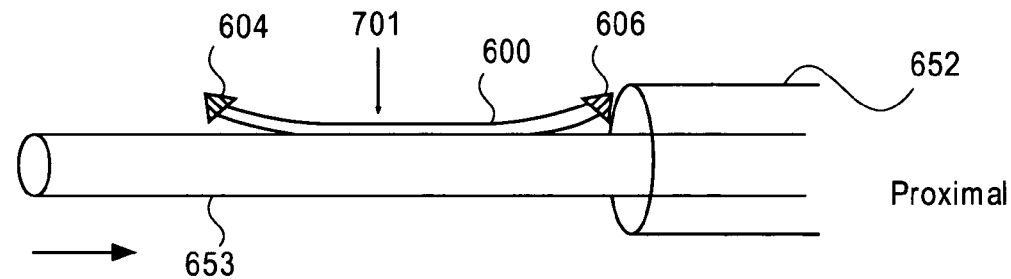
Figure 54D:
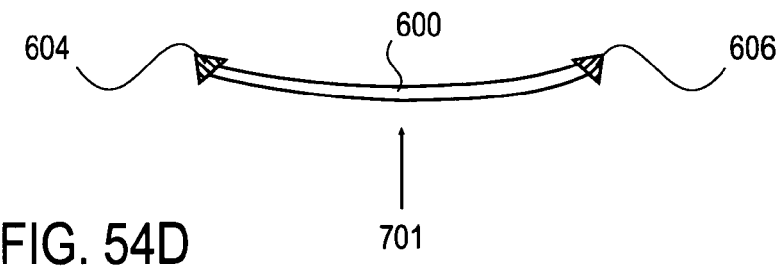

To deploy the annuloplasty device 701, the guidewire 13 is inserted into a vein the body of a patient through an introducer (not shown) as is well known in the art. A guide catheter 654 is placed over the guidewire 13 through the introducer into the vessel lumen (the vein). The guidewire 13 and the guide catheter 654 are advanced through the vessel to the right atrium and into the coronary sinus. The annuloplasty device 701 is disposed within the protective sheath 652 of the delivery device 651. The protective sheath 652 is then loaded on or over the guidewire 13, within the inner diameter of the guide catheter 654, and delivered to a location in the CS 208 adjacent to the mitral valve 210. The protective sheath 652 is then retracted slightly and proximally relative to the annuloplasty device 604 to expose the distal anchoring member 604 of the ligature 600 as shown in FIGS. 54A-54B. The distal anchoring member 604 is then inserted or anchored into the left trigone. The protective sheath 652 is further retracted proximally to expose the proximal anchoring member 606 of the ligature 600 as shown in FIG. 54C. The proximal anchoring component 606 is inserted anchored into the right trigone. Then, the annuloplasty device 701 can be completely released from the delivery device 651 as shown in FIG. 54D. A pushpin or a mechanism (not shown) can be included within the delivery device 651 to release the annuloplasty device 701.

In one embodiment, the distal end portion of the protective sheath 652 may contain a slit or cutaway section (not shown) to allow the protective sheath 652 to expand and open to allow the protective sheath 652 to slide over the annuloplasty device 701 as the protective sheath 652 is retracted during deployment.

In one embodiment, the protective sheath 652 also acts as a straightening device to temporarily straighten the annuloplasty device 701 during delivery and deployment. Once the annuloplasty device 701 is placed in the CS 208, the withdrawal of the protective sheath 652 allows the supporting structure that is curved to a particular curve to return to its curved shape as shown in FIG. 54D.

After the annuloplasty device 701 is fully deployed, the distal anchoring member 604 anchored into an area in the left trigone, the proximal anchoring member 606 anchored into an area in the right trigone, and the ligature 600 is pressed against the wall of the CS 208 on the side that faces the mitral valve annulus 209. In one embodiment, the curvature of the ligature 600 reshapes the mitral annulus 209. In one embodiment, the curvature of the ligature 600 together with the curvature of the expandable structure 602 reshapes the mitral annulus 209.

It is to be understood that the delivery device 651 can be made from materials and designs similar to current stent delivery systems. The delivery device 651 could be of the over-the-wire or rapid-exchange styles of stent delivery systems as known in the art. The delivery device 651 also could include materials or be made of materials that are compatible with X-ray, ultra sound of Magnetic Resonance Imaging (MRI) methods for the purpose of visualizing the delivery, placement and deployment of the annuloplasty device 701.

Figure 55A:
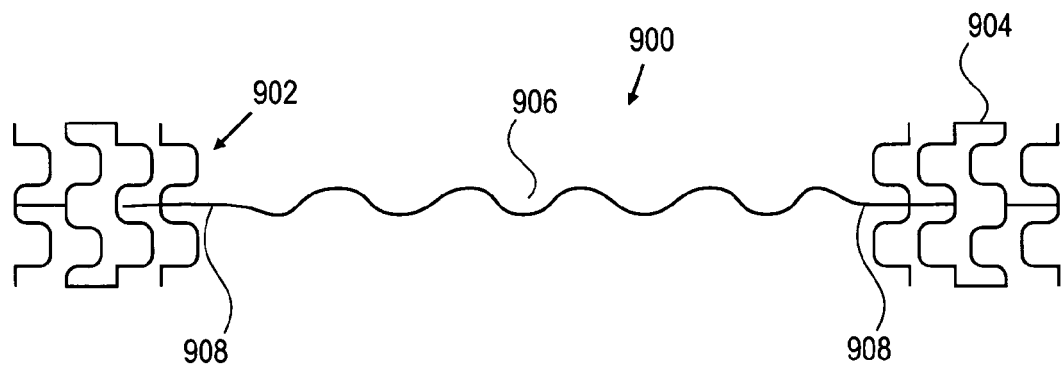
FIGS. 55A-55C illustrate an exemplary embodiment of an annuloplasty device in accordance with the present invention.
Figure 55B:
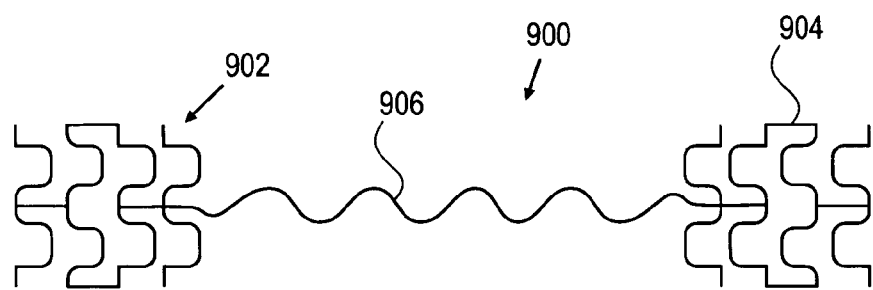

FIGS. 55A-55B illustrate cross-sectional views of an exemplary annuloplasty device 900 that can be deployed in the CS 208 to reshape the mitral valve annulus 209. In one embodiment, the annuloplasty device 900 reduces the diameter of the arc that the CS 208 circumscribes.

Figure 55C:
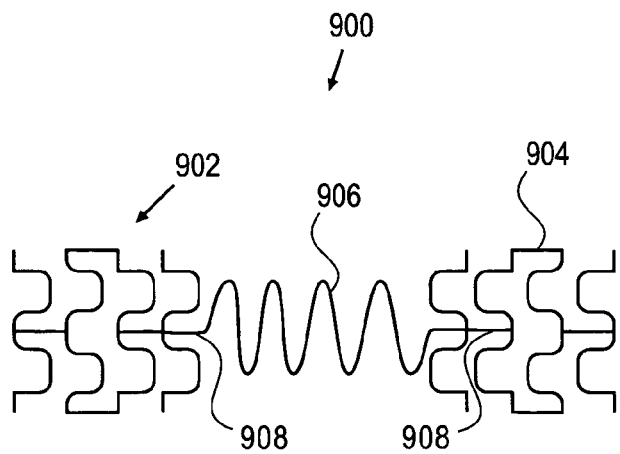

The annuloplasty device 900 comprises a distal anchoring member 902, a proximal anchoring member 904, and a spring-like spine 906. The spring-like spine 906 is constructed from a shape-memory alloy (e.g., Nitinol), which, generate a cinching force that is required to reduce the diameter of the CS 208 and the mitral valve annulus 209. During deployment, the spring-like spine 906 is stretched out for easy delivery as shown in FIG. 55A. After deployment, the spring-like spine 906 returns to the original shape as shown in FIGS. 55B and 55C. The spring-like spine 906 may be constructed to have the original shape as shown in FIG. 55C or a more expanded shape as shown in FIG. 55B. The spring-like spine 906 may be constructed of a single unit by laser cutting using Nitinol or other shape-memory material. The spring-like spine 906 can be welded together with the distal anchoring member 902 and the proximal anchoring member 904 using conventional methods (e.g., laser welding). The spring-like spine 906 can also be cut from a cylindrical tube or wound with wire using methods well known to those skilled in the art.

The distal anchoring member 902 and the proximal anchoring member 904 are similar to previously described for the annuloplasty device 601. The distal anchoring member 902 and the proximal anchoring member 904 function to grip and pull onto the venous tissue as the spring-like spine 906 resumes its shape after deployment. In one embodiment, each of the distal anchoring member 902 and the proximal anchoring member 904 is formed much like a conventional stent with modification so that each includes a link 908 that allows it to be attached to the spring-like spine 906. Additionally, each of the distal anchoring member 902 and the proximal anchoring member 904 can be made slightly larger than the inner diameter of the CS 208 such that when deployed, there is sufficient force for the distal anchoring member 902 and the proximal anchoring member 904 to grip, anchor, or deploy against the inner diameter of the CS 208.

Figure 56:
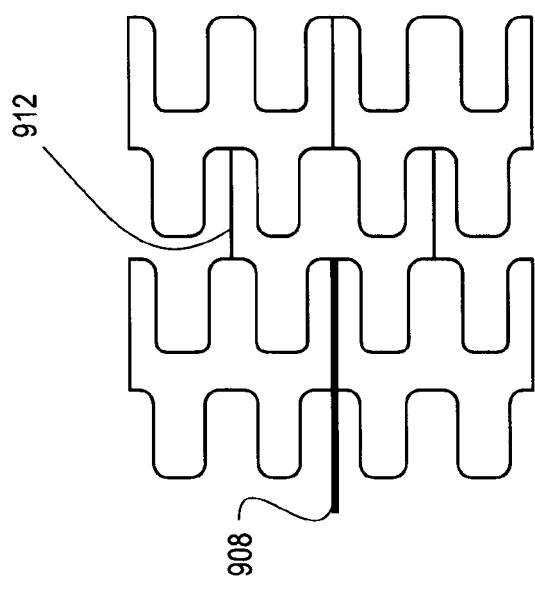
FIGS. 56-58 illustrate exemplary embodiments of a distal anchoring member and a proximal anchoring member that can be used for the annuloplasty device shown in FIGS. 55A-55C.

In one embodiment, each of the distal anchoring member 902 and the proximal anchoring member 904 includes the link 908 that is constructed to be thicker than other links typically present in a conventional stent as shown in FIG. 56. The thickness of the link 908 should be sufficient for the spring-like spine 906 to be attached to each of the distal anchoring member 902 and the proximal anchoring member 904.

Figure 57:
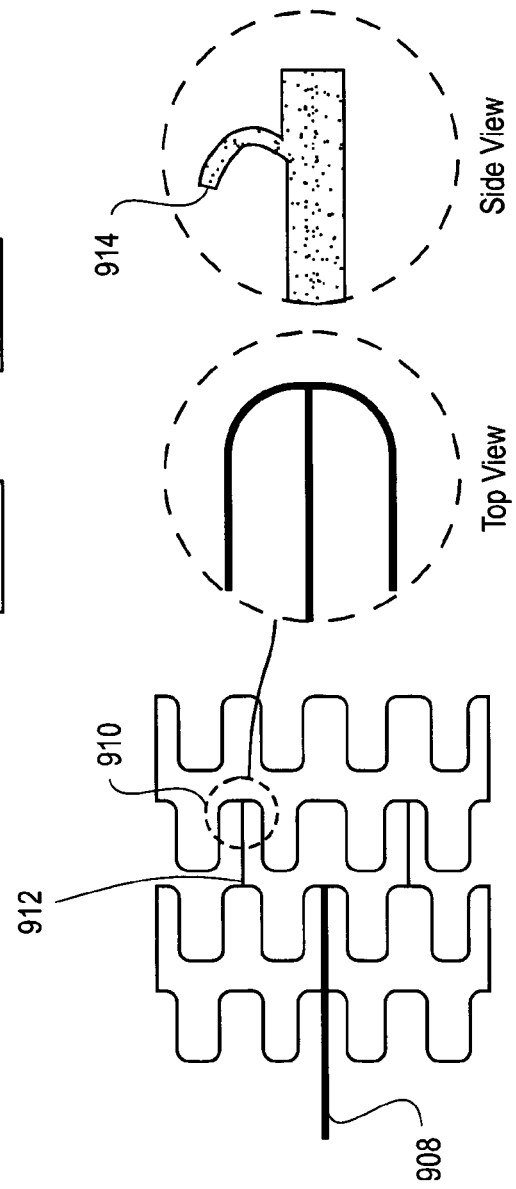

In one embodiment, each of the distal anchoring member 902 and the proximal anchoring member 904 is constructed to have crowns 910 with out-of-plane expansions or fish-scaling effects as shown in FIG. 57. This feature can be accomplished by adjusting the thickness of the struts 912 relative to the width ratio of the crowns 910. FIG. 57 represents, in one embodiment, an enhancement to traditionally cut stents which will allow the distal and proximal anchors to grip the tissue in the presence of the cinching force generated by the constriction of the spine. This figure illustrates the use of barbs or hooks that may be welded to the links and/or struts of the distal and proximal anchoring devices. These would function in a fashion similar those described for other embodiments of the anchoring members.

Figure 58:
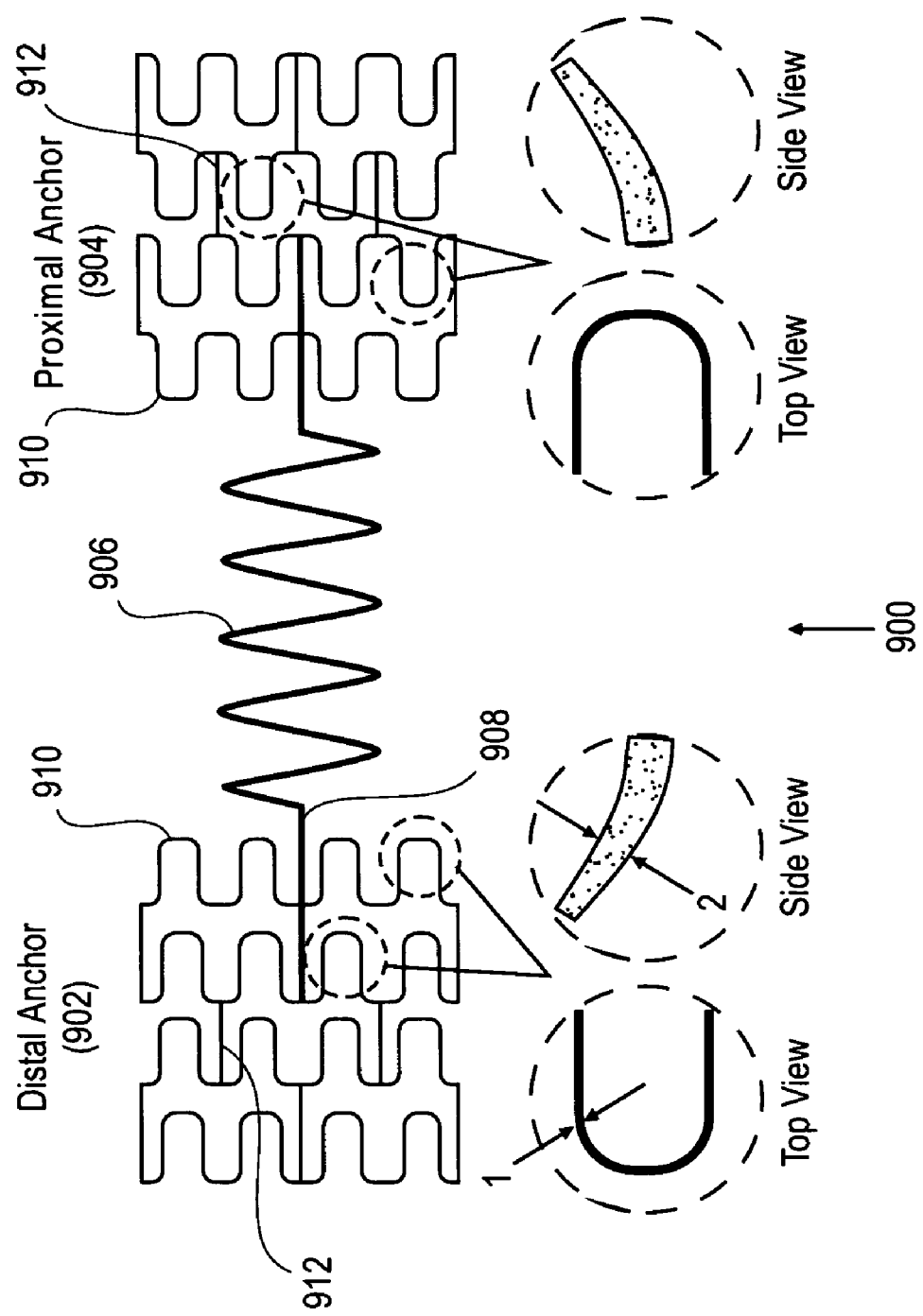

FIG. 58 illustrates that in one embodiment, the crowns 910 on the distal anchoring member 902 are pointed toward the proximal end of the annuloplasty device 900. The crowns 910 on the proximal anchoring member 904 are pointed toward the distal end of the annuloplasty device 900. The orientation of the crowns 910 in the manner mentioned ensured that the distal anchoring member 902 and the proximal anchoring member 904 are embedded deeper into the tissue of the wall of the CS 208 as the spring-like spine 906 resumes its original shape. One advantage for orienting the crowns 910 as depicted in FIG. 58 is to take advantage of the fish-scaling effect mentioned above. When an anchoring member (e.g., the distal anchoring member 902 or the proximal anchoring member 904) is expanded, the crowns 910 will expand out of the cylindrical plane defined by the main body of the anchoring member as seen in the side views of FIG. 58. Adjusting the crown width to thickness ratio controls the degree of out-of-plane deformation. The crown width and thickness have been labeled 1 and 2, respectively, in FIG. 58. When the annuloplasty device 900 is fully deployed, the cinching force generated by the contraction of the spring-like spine 906 will cause the anchoring members to further embed themselves into the tissue much like barbs or hooks.

In one embodiment, each of the distal anchoring member 902 and the proximal anchoring member 904 includes at least one anchor 914 as shown in FIG. 57. The anchor 914 further aid the distal anchoring member 902 and the proximal anchoring member 904 in anchoring into the tissue of the wall of the CS 208.

Figure 59A:
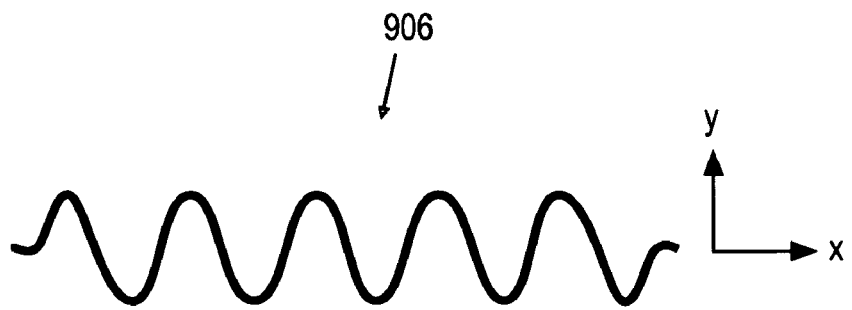
FIGS. 59A-59D illustrate exemplary embodiments of a spring-like spine in various configurations that can be used for the annuloplasty device shown in FIGS. 55A-55C.

FIG. 59A represents the spring-like spine 906 as if it were flattened onto the plane of the page. This embodiment of the spring-like spine 906 has a pure sinusoidal shape (which resembles a sine wave shape). The spring-like spine 906 is not restricted to a sinusoidal shape, but may also take on the repeating keyhole-like shape of a typical stent ring in order to exploit flexibility, strength, expansion and contraction characteristics. In an alternative embodiment, the spring-like spine 906 is a spine 936 that has the repeating keyhole-like shape of a typical stent ring as illustrated in FIG. 59D.

Figure 59B:
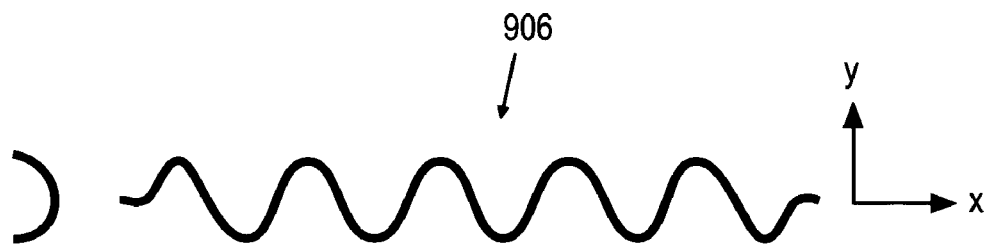
Figure 59C:
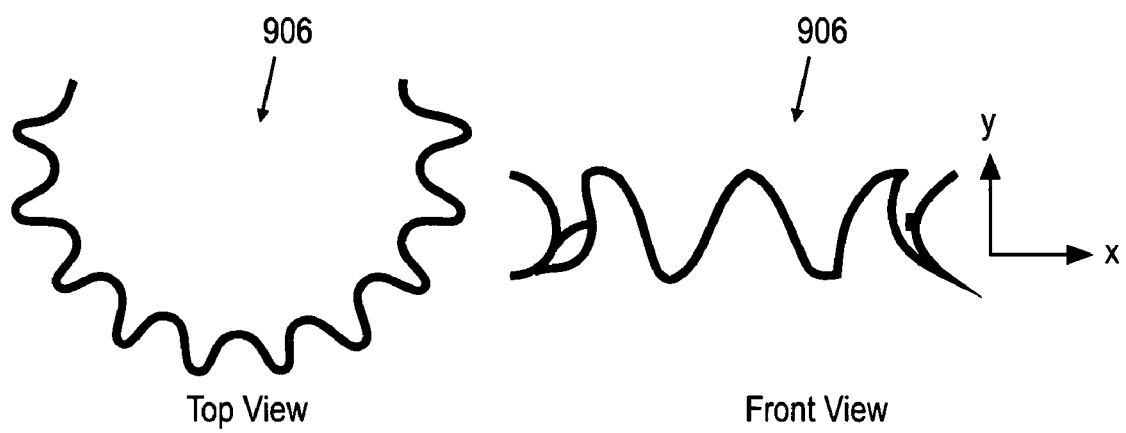
Figure 59D:
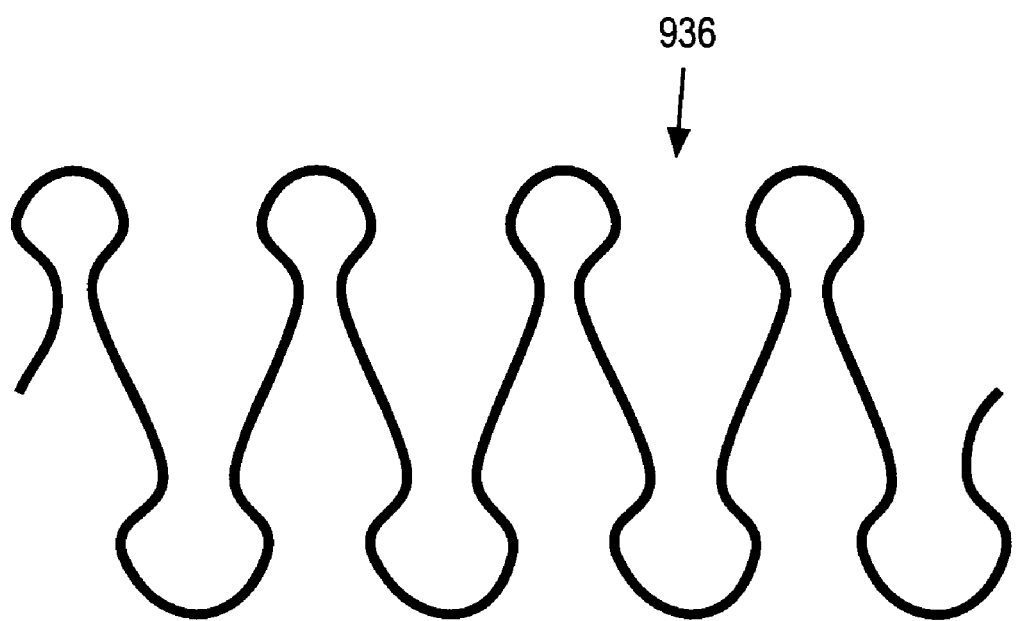

FIG. 59B illustrates the spring-like spine 906 wrapped around the x-axis as if the spine 906 has been cut from a cylindrical tube. FIG. 59C depicts the final structure of the spine 906 in a top view and a front view. The spring-like spine 906 is transformed from the configuration shown in FIG. 59B by wrapping itself around the y-axis. FIG. 59C represents the final shape of the spring-like spine 906, which has a predetermined curvature. The spring-like spine 906 may be characterized as a tubular spring that has been wrapped around the y-axis such that it circumscribes a particular arc (e.g., the arc of the CS 208).

The spring-like spines described may have features are adjusted to achieve specific functionality. For example, the spring-like spines could be modified by adjusting the period or frequency of the repeating pattern, the amplitude of the repeating pattern, or the number of repeating patterns along the length of the spines.

The annuloplasty device 900 can be delivered into the CS 208 using a conventional method and a conventional delivery device or the delivery devices previously described.

Figure 60:
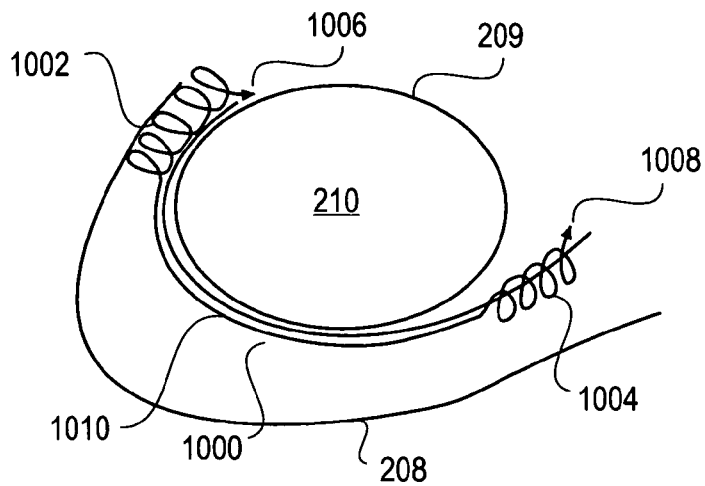
FIG. 60 illustrates an exemplary embodiment of an annuloplasty device comprising coiled anchoring members.

FIG. 60 illustrates an exemplary annuloplasty device 1000 that can be deployed in the CS 208 to reshape the mitral valve annulus 209. In one embodiment, the annuloplasty device 1000 reduces the diameter of the arc that the CS 208 circumscribes thereby reshaping the mitral valve annulus 209.

The annuloplasty device 1000 comprises a distal anchoring member 1002, a proximal anchoring member 1004, and a ligature 1010. In one embodiment, the ligature 1010 is constructed from a shape-memory alloy (e.g., Nitinol), which, generate a cinching force that is required to reduce the diameter of the CS 208 and the mitral valve annulus 209. During deployment, the ligature 1010 may be stretched out for easy delivery. After deployment, the ligature 1010 returns to the original shape which may have a predetermine curvature for which the CS 208 and the mitral valve annulus 209 are to conform to as shown in FIG. 60.

The annuloplasty device 1000 may be constructed of a single unit by laser cutting using Nitinol or other shape-memory material. The annuloplasty device 1000 can also be cut from a cylindrical tube or wound with wire using methods well known to those skilled in the art. Alternatively, the ligature 1010 may be welded together with the distal anchoring member 1002 and the proximal anchoring member 1004 using conventional methods (e.g., laser welding).

The distal anchoring member 1002 and the proximal anchoring member 1004 are similar to previously described for the annuloplasty device 601. The distal anchoring member 1002 and the proximal anchoring member 1004 function to grip and pull onto the venous tissue as the ligature 1010 resumes its shape after deployment. In one embodiment, each of the distal anchoring member 1002 and the proximal anchoring member 1004 is configured to have a coiled or helical shapes as shown in FIGS. 61A-61E. The coiled/helical shaped anchoring members (1002 and 1004) can be delivered at a small profile and expand into the CS 208. The ends of the coiled/helical shaped anchoring members can protrude through the CS 208 and into the left or the right trigone, the annulus tissue, or other myocardial tissue proximate the CS 208 for better anchoring. Alternatively, at least one anchor can be attached or included to the ends of the coiled/helical shaped anchoring members as shown in FIG. 60. In FIG. 60, the distal anchoring member 1002 includes an anchor 1006 and the proximal anchoring member 1004 includes an anchor 1008. The anchor can be a barb, hook, helix, coil, flange, screw, staple, and rivet, to name a few.

Figure 61A:
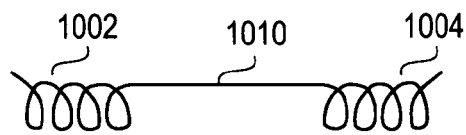
FIGS. 61A-61F illustrate exemplary embodiments of coiled anchoring members.

FIG. 61A illustrate an embodiment of the annuloplasty device with the proximal anchoring member 1004 and the distal anchoring member 1002 having coils that turn in opposite direction. The proximal anchoring member 1004 and the distal anchoring member 1002 are essentially mirror image of each other. In one embodiment, the distal anchoring member 1002 has a clockwise rotation while the proximal anchoring member 1004 has a counter-clockwise rotation. As can be seen, the distal anchoring member 1002, the ligature 1010, and the proximal anchoring member 1004 are parts of one continuous structure made of the same material.

Figure 61B:
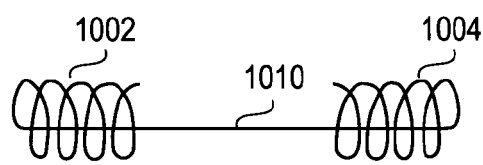

Pulling on the ligature 1010 induces the coil stacking of the distal anchoring member 1002 and the proximal anchoring member 1004 which provide more anchoring force and support for the aniuloplasty device 1000. In one embodiment, the ligature 1010 begins at the most distal end portion of the distal anchoring member 1002 and at the most proximal end portion of the proximal anchoring member 1004 as illustrated in FIG. 61B.

Figure 61C:
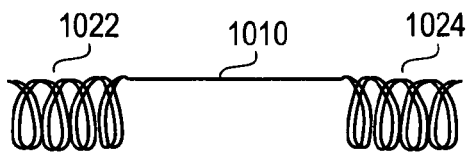
Figure 61D:
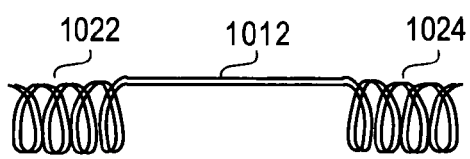

In an alternative embodiment, the annuloplasty device 1000 includes multiple structures as shown in FIG. 61C. In this embodiment, the distal anchoring member 1002 includes at least two coils wound in the same direction and the proximal anchoring member 1004 also includes at least two coils wound in the same direction. The ligature 1010 can be a single-stranded structure as shown in FIG. 61C. Alternatively, the ligature 1010 can be a double-stranded structure as shown in FIG. 61D. The annuloplasty device 1000 with at least two coils provides additional support to the distal anchoring member 1002 and the proximal anchoring member 1004.

Figure 61E:
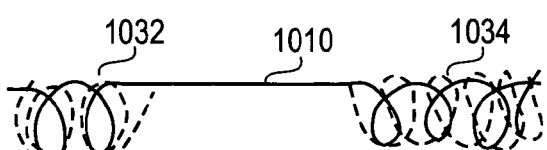

In another alternative embodiment, the annuloplasty device 1000 includes multiple coils each turning an opposite direction and interlocking one another as illustrated in FIG. 61E. In this embodiment, the ligature 1010 can be a single-stranded structure as shown in this figure or a double-stranded structure similar to the one shown in FIG. 61D.

Figure 61F:
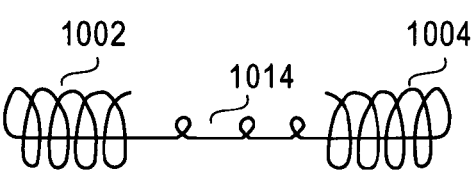

In one embodiment, the ligature 1010 itself could include coiled or helical turn to form a ligature 1014 as shown in FIG. 61F. Pulling on the ligature 1014 exerts more torques onto the distal anchoring member 1002 and the proximal anchoring member 1004 thus, providing more radial anchoring force to these anchoring members.

The annuloplasty device 1000 can be delivered into the CS 208 using a conventional method and a conventional delivery device or the delivery devices previously described.

FIGS. 62A-62D illustrate an exemplary embodiment of the present invention that can be used to treat a defective heart valve such as that seen in a mitral valve regurgitation condition. As previously discussed, anchoring members may be placed or anchored in the coronary sinus at two opposite ends with a connecting member that can pull the anchoring members toward each other in order to change the shape of the mitral valve annulus. In many instances, adjustability and removability of the anchoring members without complication (e.g., surgery) are desirable. The embodiments shown in the FIGS. 62A-62D describe the use of expandable baskets as anchoring members to deploy in the coronary sinus (or other blood vessel).

In FIGS. 62A-62D, an implantable device 2202, which can be an annuloplasty device, is moveably disposed within a delivery sheath 2204. The implantable device 2202 includes a distal expandable basket 2230 and a proximal expandable basket 2236 connected by a connecting member 2242. The distal expandable basket 2230 and the proximal expandable basket 2236 are delivered in their collapsed or compressed state. The delivery sheath 2204 functions to constrain the distal expandable basket 2230 and the proximal expandable basket 2236 in their collapsed state. Once delivered to their respective and desired location, the distal expandable basket 2230 and the proximal expandable basket 2236 are allowed to expand and deploy against the inner wall of the coronary sinus (or blood vessel), in one embodiment. To deploy the distal expandable basket 2230 and the proximal expandable basket 2236, the delivery sheath 2204 is withdrawn to allow the distal expandable basket 2230 and the proximal expandable basket 2236 to expand.

The implantable device 2202 is releasably coupled to an actuator 2206 at a junction 2208. The actuator 2206 is coupled to the implantable device by coupling to the proximal end of the connecting member 2242. The actuator 2206 is used to facilitate the deployment of the implantable device 2202. The actuator 2206 is also used to apply tension on the distal expandable basket 2230, the proximal basket 2236, and the connecting member 2242 in order to reshape the blood vessel or the coronary sinus, in one embodiment.

Figure 62A:
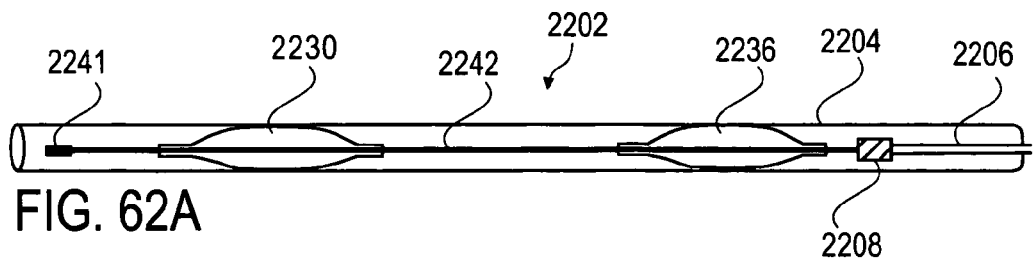
FIGS. 62A-62E illustrate an exemplary embodiment of an annuloplasty device having distal and proximal expandable baskets connected by a connecting member.

FIG. 62A shows the implantable device 2202 contained in the delivery sheath 2204. As shown in this figure, the distal expandable basket 2230 and the proximal expandable basket 2236 are in their collapsed state.

Figure 62B:
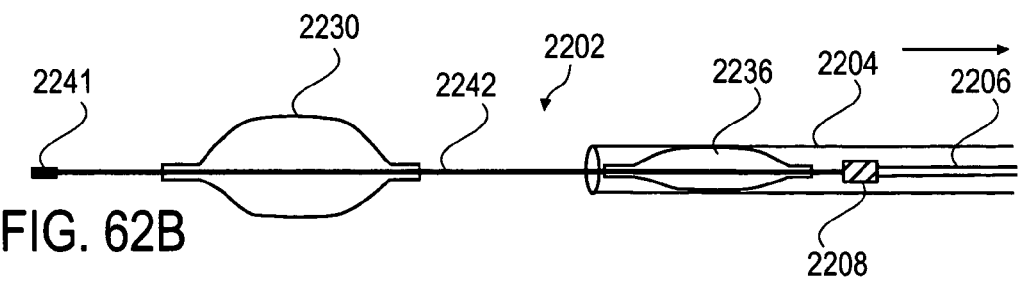

FIG. 62B shows the distal expandable basket 2230 being deployed. Once the device 2202 is in position and the distal expandable basket 2230 is in the desired location within the blood vessel or the coronary sinus, the delivery sheath 2204 is retracted to allow the distal expandable basket 2230 to expand and anchor or deploy against the inner wall of the blood vessel (or other vessel) at the desired location.

Figure 62C:
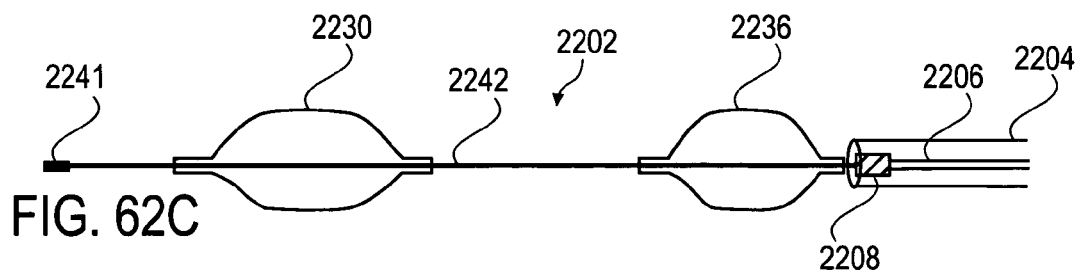

FIG. 62C shows the proximal basket 2236 being deployed. The proximal expandable basket 2236 is deployed while tension is applied to the actuator 2206 (e.g., as is needed to change the shape of the blood vessel, the coronary sinus, and/or the mitral valve annulus). After the proximal expandable basket 2236 is placed in the desired location, with tension being applied, the delivery sheath 2204 is retracted further proximally to allow the proximal expandable basket 2236 to expand and anchor or deploy. In one embodiment, the proximal expandable basket 2236 is deployed within the blood vessel similarly to the distal expandable basket 2230. In another embodiment, the proximal expandable basket 2236 is deployed outside of the ostium of the coronary sinus in the right atrium and held against the ostium as shown in FIG. 62E.

When there is need for adjustment or repositioning of the proximal expandable basket 2236 or the distal expandable basket 2230, the delivery sheath is advanced over the proximal expandable basket 2236 or the distal expandable basket 2230 to collapse the proximal expandable basket 2236 or the distal expandable basket 2230 to allow for repositioning or adjustment.

Figure 62D:
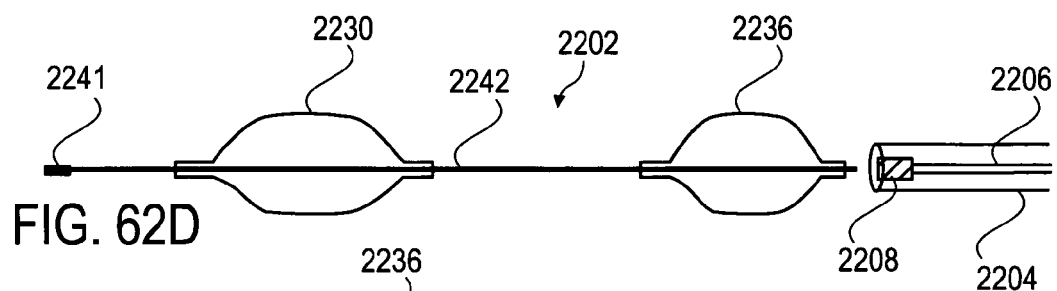
Figure 62E:
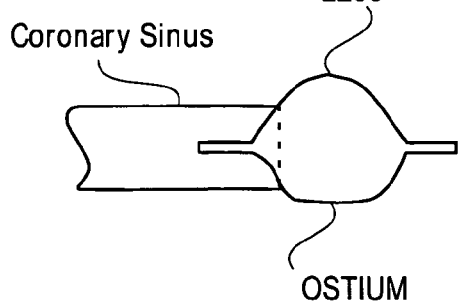

FIG. 62D shows the removal of the actuator 2204 and the delivery sheath 204 after proper positioning of the distal expandable basket 2230 and the proximal expandable basket 2236 is achieved. After the distal expandable basket 2230 and the proximal expandable basket 2236 are deployed or anchored in place, the connecting member 2242 applies tension to pull on the baskets 2230 and 2236. The tension is sufficient to reshape the coronary sinus or the blood vessel. The connecting member 2242 may be positioned on or proximate a side of the inner wall of the blood vessel or the coronary sinus.

Figure 63:
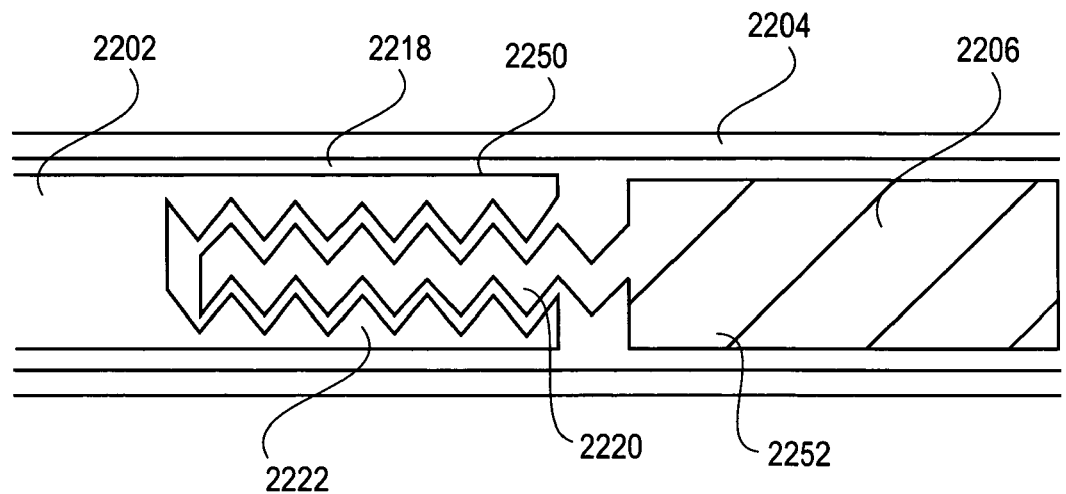
FIG. 63 illustrates an exemplary embodiment of a connecting member to connect an actuator to the annuloplasty device shown in FIGS. 62A-62D.
Figure 64:
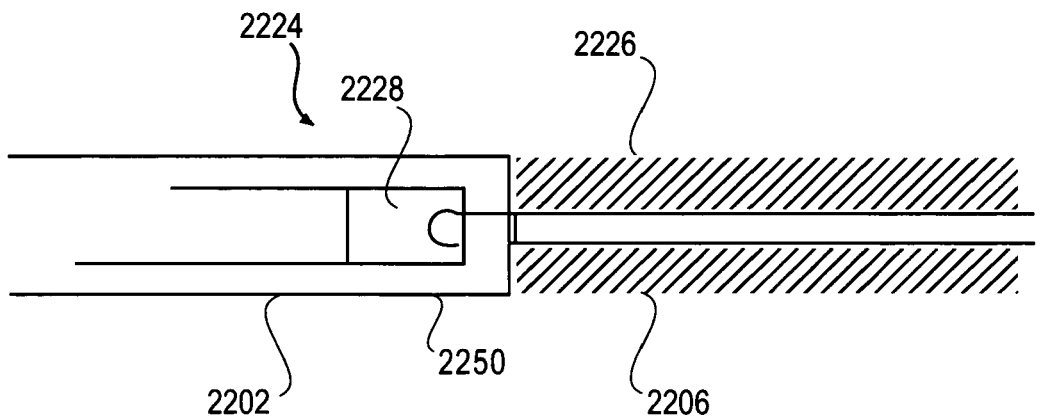
FIG. 64 illustrates another exemplary embodiment of a connecting member to connect an actuator to the annuloplasty device shown in FIGS. 62A-62D.

FIGS. 63-64 illustrate enlarged views of the junction 2208, which is the connecting point for the actuator 2206 and the implantable device 2202. In one embodiment, the actuator 2206 is coupled to the implantable device 2202 through a connection mechanism 2218 as shown in FIG. 63. The connection mechanism 2218 includes a screw thread structure 2220 and a complimentary screw thread structure 2222. The screw thread structure 2220 couples to or extends from the actuator 2206 at the distal end section 2252 of the actuator 2206. The screw thread structure 2222 couples to or extends from the implantable device 2202 at the proximal end section 2250 of the implantable device 2202. One of the screw thread structure 2220 and the screw thread structure 2222 can be a female thread structure while the other can be a complimentary male thread structure. In FIG. 63, the screw thread structure 2222 is a female thread structure and the screw thread structure 2220 is a male thread structure. The screw thread structure 2220 and screw thread structure 2222 engage one another to couple the implantable device 2202 to the actuator 2206. The screw thread structure 2220 and the screw thread structure 2222 disengage one another to release or detach the actuator 2206 from the implantable device 2202. Thus, during deployment, the screw thread structure 2220 and the screw thread structure 2222 engage one another to allow the actuator 2206 to move the implantable device 2202 and after the deployment, the screw thread structure 2220 and the screw thread structure 2222 disengage one another to allow the actuator 2206 to be detached from the implantable device 2202.

It is to be appreciated that there are many connection mechanisms that rely on a rotary and/or longitudinal motion and/or release of the implantable device 2202. Alternatively, the actuator 2206 can be coupled to the implantable device 202 using a loop connection system 2224 as illustrated in FIG. 64. The proximal section 2250 of the implantable device 2202 may include a loop, opening, or a slot 2228. The distal section 2252 of the actuator 2206 may include a wire loop 2226 that can be inserted through the slot 2228. The wire loop 2226 keeps the actuator 2206 coupled to the implantable device 2202 until the removal of the wire loop 2226 from the slot 2228. The wire loop 2226 may be removed by releasing one end of the wire loop 2226 while pulling on the other end of the wire loop 2226. The wire loop 2226 holds the implantable device 2202 against the actuator 2206 such that the implantable device 2202 can be pushed or pulled by the actuator 2206. The wire loop 2226 may simply act to couple the implantable device 2202 to the actuator 2206 while the actuator 2206 is the member that performs the controlling or moving of the implantable device 2202.

The delivery sheath 2204 is made out of a biocompatible material such as those typically used for a catheter. The delivery sheath 2204 can be made out of a polymer commonly used in catheter construction such as Nylon, Pebax, Polyurethane, PEEK, Polyolefin, etc. . . . The delivery sheath 2204 is flexible but need not be and can be made to have preformed curvature to facilitate the maneuvering of the delivery sheath 2204 into the target blood vessel (e.g., a coronary sinus). In one embodiment, the delivery sheath 2204 is substantially smaller compared to the blood vessel that the delivery sheath 2204 is to be inserted into. The delivery sheath 2204 introduces the implantable device 2202 to a treatment site (e.g., a site within the blood vessel). The treatment site can be a coronary sinus that substantially encircles a mitral valve and mitral valve annulus (previously shown).

The delivery sheath 2204 constrains the implantable device 2202 in the pre-delivery or pre-deployment state. In one embodiment, in the pre-deployment state, the distal expandable basket 2230 and the proximal expandable basket 2236 are in a collapsed state as shown in FIG. 62A that allows them to be conveniently disposed within the delivery sheath 2204. As discussed, retraction of the delivery sheath 2204 allows the distal expandable basket 2230 and the proximal expandable basket 2236 to be deployed to their non-compressed state.

In one embodiment, to deliver the implantable device 2202 to the blood vessel, a sub-selective sheath (not shown) is used. Sub-selective delivery is known in the art. In this embodiment, the sub-selective sheath is advanced over a guidewire into the blood vessel (or the coronary sinus) using conventional technique. The sub-selective sheath is advanced over the guidewire to the anchor site for the distal expandable basket 2230. The guidewire is then withdrawn. The implantable device 2202 constrained in the delivery sheath 2204 is advanced to the anchor site through the sub-selective sheath. To deploy the implantable device 2202, the sub-selective sheath is retracted proximally to allow sufficient room for the deployment. After the distal expandable basket 2230 is in position, the delivery sheath 2204 is retracted as previously discussed. Then, with tension applied, after the proximal expandable basket 2236 is in position, the delivery sheath 2204 is also retracted as previously discussed. The sub-selective sheath can be withdrawn completely when deployment is achieved.

In other embodiments, the delivery sheath 2204 can be configured to include a lumen that can accommodate a guidewire. With this configuration, the delivery sheath 2204 can be advanced into the blood vessel and to the anchor site without the sub-selective sheath. In such embodiments, the delivery sheath 2204 can be advanced over the guidewire into the blood vessel. The deployment can then be carried out as previously discussed. In other embodiments, the connecting member 2242 is configured with an atraumatic tip 2241 to prevent injury during advancement especially when the delivery sheath 2204 is used to deliver the implantable device 2202.

During deployment, the implantable device 2202 can be flushed with a fluid to lubricate the implantable device 2202 and the inner space of the delivery sheath 2204 to minimize friction between the implantable device 2202 and the delivery sheath 2204 so as to allow the distal and proximal expandable baskets 2230 and 2236 to move out of the delivery sheath 2204 for deployment. The implantable device 2202 may be also coated with a lubricious material that facilitates the movement of the distal and proximal expandable baskets 2230 and 2236 in and out of the delivery sheath 2204.

The delivery sheath 2214 may also include radiopaque markers (not shown) to provide positioning information. The delivery sheath 2214 may also include other type of markers compatible with various types of imaging techniques known in the art such as echo imaging, infrared illuminations x-ray, and magnetic resonance imaging.

The actuator 2206 may be a hollow or a solid member, rod, or wire and may be coated with a lubricious material that facilitates the movement of the actuator 2206 in and out of the delivery sheath 2204. The actuator 2206 is releasably coupled to the implantable device 2202 in a way that allows the actuator 2206 to engage or disengage, attach to or detach from the implantable device 2202 when desired. For deployment of the implantable device 2202, the actuator 2206 engages the implantable device 2202 to move and/or facilitate in deploying the implantable device. After the deployment of the implantable device 2202, the actuator 2206 disengages the implantable device 2202 and can be withdrawn from the blood vessel or the coronary sinus.

FIGS. 65A-65C illustrate exemplary embodiments of the distal expandable basket 2230 and the proximal expandable basket 2236. The distal expandable basket 2230 and the proximal expandable basket 2236 are similar. Each of the distal expandable basket 2230 and the proximal expandable basket 2236 comprises an expandable strut assembly 3024 which possesses spring-like or self-expanding properties and can move from a compressed or collapsed position as shown in FIG. 62A to an expanded or deployed position shown in FIGS. 62B-62D.

In FIG. 65A, expandable strut assembly 3024 includes an elongated cylindrical center portion 3034 and proximal and distal end portions 3036 and 3038 which are shaped as truncated cones, terminating at proximal and distal, hollow, cylindrical, collars 3040 and 3042. Starting from the proximal collar 3040, the strut assembly 3024 comprises a plurality of individual struts 3044 which taper upward to form the proximal truncated cone portion 3036 of the of the strut assembly 3024. The struts 3044 continue, extending longitudinally, to form the elongated, straight, center portion 3034 of the strut assembly. The struts 3044 then taper downward forming the distal truncated cone portion 3038 of the strut assembly and terminate at the distal collar 3042. Arrow 3046 shows the angle that the distal truncated cone portion 3038 makes with the center portion 3034. While the figures show only four individual struts, the expandable basket is not limited to this configuration as strut assemblies containing more or less struts are practical.

FIG. 65B illustrates an alternative configuration of the individual struts 3044. The struts 3044 in FIG. 65A have straight shapes. The struts 3044 in FIG. 65B have spiral shapes, which can make the collapsing or compressing of the expandable baskets easier. The struts 3044 can have other suitable shapes not shown here.

FIG. 65C illustrates yet another alternative configuration of each of the distal expandable basket 2230 and the proximal expandable basket 2236. Each of the distal expandable basket 2230 and the proximal expandable basket 2236 includes a proximal strut assembly 3042 which includes a number of self-expanding struts 3044 that extend radially outward from the unexpanded position, to an expanded, implanted position as previous discussed. The proximal strut assembly 3042 is coupled to a distal strut assembly 3046, which also includes a number of self-expanding struts 3044 that extend radially out once placed in the expanded position. The proximal strut assembly 3042 and distal strut assembly 3046 are coupled together by intermediate links 3050 which provide a region of increased bendability and flexibility to the basket. In this regard, the intermediate links 3050 act similarly to a mechanical hinge to allow the proximal strut assembly 3042 and distal strut assembly 3046 to move freely relative to each other when negotiating tortuous curves in the patient's anatomy. Enhanced flexibility of the intermediate links 3050 can be achieved by decreasing the strut width or the strut thickness from that used for the proximal or distal strut assembly.

The struts 3044 of the proximal strut assembly 3042 are attached to a collar 3052 which can be rotatably attached to the connecting member 2242. The opposite ends of each strut 3044 are in turn attached to a deployment ring 3054, also made from a self-expanding material, which aids in the expansion of the proximal assembly 3042. The deployment ring 3054 is shown having a number of pleats 3056 which helps when collapsing the ring 3054 to its delivery position. The distal strut assembly 3046 may likewise include a deployment ring 3054 attached to the ends of the struts 3044. In a like manner, this deployment ring 3054 serves to expand the distal assembly as well. The deployment rings 3054 are shown having a zigzag pattern which forms peaks 3043 and valleys 3045 and other patterns such an undulations. Generally, the intermediate links 3050 are connected to the peaks 3043 of the deployment rings 3054 with the ends of the struts 3044 being connected to the valleys 3045 of the ring 3054. As a result, each of the baskets 2230 and 2236 will enter the delivery sheath 2242 in a smoother fashion.

Each of the strut assemblies described may be produced by several methods including electro-discharge machining and chemical etching. One method is to laser machine a thin-walled tubular member, such as a hypotube. In this procedure, a computer controlled laser cuts away portions of the hypotube following a pre-programmed template to form the desired strut pattern. Methods and equipment for laser machining small diameter tubing may be found in U.S. Pat. No. 5,759,192 (Saunders) and U.S. Pat. No. 5,780,807 (Saunders), which have been assigned to Advanced Cardiovascular Systems, Inc.

The tubing used to make the strut assembly may be made of any biocompatible spring steel or shape memory alloy. The 300 series stainless steel alloys are well suited to this application as is type 316L stainless steel per ASTM F138-92 or ASTM F139-92 grade 2. Other suitable materials include nickel-titanium alloys, such as Nitinol, including nickel-titanium alloys with optional ternary element added, and wherein the alloy may be processed to varying degrees to achieve different stress-strain behavior such as superelasticity or linear pseudoelasticity. The ternary elements include, for example, platinum, palladium, chromium, iron, cobalt, vanadium, manganese, boron, aluminum, tungsten, or zirconium.

Figure 66:
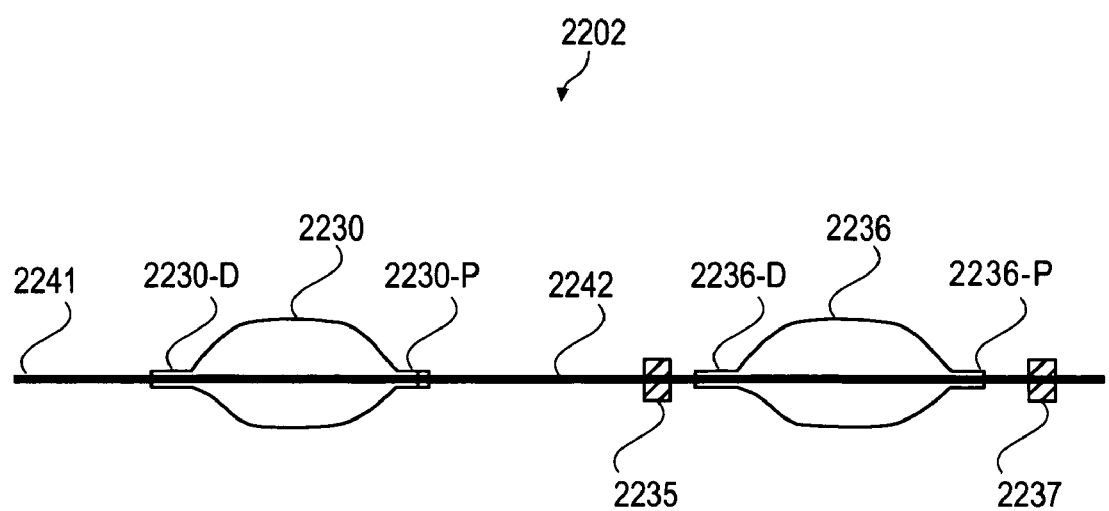
FIG. 66 illustrates the annuloplasty device shown in FIGS. 62A-62D with a distal stop and a proximal lock.

Each of the distal expandable basket 2230 and the proximal expandable basket 2236 is coupled to the connecting member 2242 at the center of each basket. The connecting member 2206 thus runs through the center of each of the baskets 2030 and 2036. In one embodiment, distal expandable basket 2230 is fixed at one end (e.g., the distal end of the distal expandable basket 2230) on the connecting member 2242 and not at the other end (e.g., the proximal end of the distal expandable basket 2230). As shown in FIG. 66, the distal expandable basket 2230 is coupled to the connecting member 2242 at the distal end 2030-D. The proximal end 2030-P of the distal expandable basket 2230 is disposed over the connecting member 2242 but is not fixed to the connecting member 2242. The proximal end 2030-P thus can slide along the connecting member 2242. This allows the distal expandable basket 2230 to easily expand and compress over the connecting member 2242. Similarly, the proximal expandable basket 2236 is coupled to the connecting member 2242 at the distal end 2236-D. The proximal end 2236-P of the proximal expandable basket 2236 is disposed over the connecting member 2242 but is not fixed to the connecting member 2242. The proximal end 2236-P thus can slide along the connecting member 2242. This also allows the proximal expandable basket 2236 to easily expand and compress over the connecting member 2242.

In one embodiment, the proximal expandable basket 2236 is somewhat slideable over the connecting member 2242. Both the distal end 2236-D and the proximal end 2236-P of the proximal expandable basket are not fixed on the connecting member 2242. This embodiment provides an implantable device 2202 with a wider range of adjustability. For example, one implantable device 2202 can be used for various length and/or size of the blood vessel or the coronary sinus. In this embodiment, a distal stop 2235 can be placed on the connecting member 2242. The distal stop 2235 defines the distal travel distance for the proximal expandable basket 2236 (e.g., the proximal expandable basket 2236 will not be able to travel pass the distal stop 2235). The distal stop 225 can be a ring, a band, or other suitable feature created on the connecting member 2242 as is known in the art.

In one embodiment, a proximal end lock 2237 is included in the implantable device 2202. The proximal end lock 2237 functions to allow for additional tension to be applied on the implantable device 2202 after the distal expandable basket 2230 and the proximal expandable basket 2236 are deployed. The proximal end lock 2237 also functions to lock or fix the position of the proximal expandable basket 2236 on the connecting member 2242, especially when the proximal expandable basket 2236 is not fixed on the connecting member 2242.

Examples of a proximal end lock 2237 can be found in U.S. Pat. No. 6,402,781 or publication WO 01/54,618. Configuration of a locking device that can be incorporated into the implantable device 2202 is known in the art.

In one embodiment, the implantable device 2202 is an annuloplasty device that can reshape a mitral valve and/or a mitral valve annulus. In one embodiment, the implantable device 2202 reduces the radius of the arc that a defective coronary sinus has thereby reshaping a mitral valve annulus that is adjacent the coronary sinus. In another embodiment, the implantable device reduces the curvature of the coronary sinus thus allowing the coronary sinus to exert pressure or force onto the mitral valve annulus, thus, bringing the leaflets of the mitral valve closer to each other.

In one embodiment, a method for deploying a device percutaneously into the coronary sinus (e.g., such as any one the methods described herein) may be combined with a percutaneous method of deploying a device on the mitral valve (e.g., such as a support annulus around the mitral valve annulus or a set of joined clips which attach to the mitral valve's leaflets). In this embodiment, a general technique would include percutaneously deploying (e.g., with a first catheter) a device into the coronary sinus (e.g., near the mitral valve) and percutaneously deploying (e.g., with a second catheter) a device onto the mitral valve (e.g., a support annulus). Device which may be deployed onto the mitral valve or into the coronary sinus are described in several co-pending U.S. Patent Applications which are hereby incorporated herein by reference, these applications beings: (1) Apparatus and Methods for Heart Valve Repair, by inventors Gregory M. Hyde, Mark Juravic, Stephanie A. Szobota, and Brad D. Bisson, filed Nov. 15, 2002, (2) Heart Valve Catheter, by inventor Gregory M. Hyde, filed Nov. 15, 2002, (3) Valve Adaptation Assist Device, by inventors William E. Webler, James D. Breeding, Brad D. Bisson, Fira Mourtada, Gregory M. Hyde, Stephanie A. Szobota, Grabiel Asongwe, and Jefferey T. Ellis, filed Nov. 15, 2002, (4) Valve Annulus Constriction Apparatus and Method, by inventors Peter L Callas and Richard Saunders, filed Nov. 15, 2002, and (5) Apparatuses and Methods for Heart Valve Repair, by inventor Gregory M. Hyde, filed Oct. 15, 2002.

A kit (e.g., a kit of multiple catheters with instructions for use thereof) may be used to perform the combination of (a) percutaneously deploying (e.g., with a first catheter) a device into the coronary sinus (e.g., near the mitral valve) and (b) percutaneously deploying (e.g., with a second catheter) a device onto the mitral valve. For example, a first catheter, such as the medical device 200A (FIG. 23), may be combined in a kit with a second catheter designed to percutaneously apply a member near the mitral valve, such as a support annulus to be attached on the mitral valve to reshape the mitral valve or a set of joined clips which grasp (e.g., attach to) the mitral valve leaflets.

In one embodiment, a support annulus (or clips, ligature) percutaneously placed near a mitral valve region, or a device placed in the coronary sinus to treat the mitral valve, may be used to deliver or release a drug or therapeutic agent to treat mitral valve regurgitation. Various drugs are known in the art for treating mitral valve regurgitation. For example, administering nitroprusside (a vascular smooth muscle relaxant) may effectively diminish the amount of mitral regurgitation, thereby increasing forward output by the left ventricle and reducing pulmonary congestion. Inotropic agents such as dobutamine may also be administered to increase the force of contraction of the myocardium. In one embodiment, a percutaneous medical device to treat mitral valve regurgitation, such as a support annulus for resizing a mitral valve annulus, clips to ligate the mitral valve leaflets, or a device placed in the coronary sinus near the mitral valve region, may be coated with these exemplary drugs for delivery near the mitral valve region. The drugs may have timed-release features to be released slowly over a certain period of time. The drug eluting support annulus or other devices may also have the drug or agent dispersed on the surface of the support annulus or other devices, or co-dissolved in a matrix solution to be dispersed on the support annulus. Methods to coat the support annulus with a therapeutic drug include dip coating, spin coating, spray coating, or other coating methods commonly practiced in the art.

In some cases, patients with defective heart valves may have concomitant coronary artery disease (CAD). As such, it may be advantageous for a support annulus to deliver a drug to treat occlusions in the artery or other related CAD such as vulnerable plaque. The drug to treat CAD may be delivered alone or in combination with drugs to treat mitral valve regurgitation. Drugs to treat CAD include, but are not limited to, statins, lipid lowering agents, antioxidants, extracellular matrix synthesis promoters, inhibitors of plaque inflammation and extracellular degradation, estradiol drug classes and its derivatives.

In one embodiment, the drugs to treat CAD may be coated on a support annulus or other device using methods such as dip coating, spin coating, spray coating or other coating methods known in the art. The drug may alternatively be encapsulated in microparticles or nanoparticles and dispersed in a coating on the support annulus or other device. A diffusion limiting top-coat may optionally be applied to the above coatings. The active agents may optionally be loaded on a support annulus or other device together either by adding them together to the solution of the matrix polymer before coating, or by coating different layers, each containing a different agent or combination of agents. The drug eluting support annulus or other device may alternatively have an active agent or a combination of agents dispersed in a bioerodable annulus-forming polymer.

The foregoing description describes percutaneous methods (e.g., catheter based techniques) for delivering the annuloplasty devices described herein. It will be appreciated that surgical (non-percutaneous) techniques may alternatively be used to deploy/deliver these annuloplasty devices.

I claim:
1. A medical device, comprising:
a delivery sheath;

an implantable device moveably disposed within the delivery sheath;

the implantable device further comprises a distal expandable basket and a different proximal expandable basket connected by a connecting member, wherein the connecting member is coupled at a first end to a proximal end of the distal expandable basket and at a second end to a distal end of the proximal expandable basket, wherein the proximal end of the distal expandable basket and a proximal end of the proximal expandable basket are both slideable along the connecting member when the expandable baskets are expanding and collapsing, and wherein the distal end of the distal expandable basket and the distal end of the proximal expandable basket are both shaped as truncated cones;

each of the distal expandable basket and proximal expandable basket being collapsed during delivery and expanded after deployment, wherein the delivery sheath constrains the distal expandable basket and the proximal expandable basket until deployment; and an actuator releasably coupling to the implantable device at a portion of the connecting member, the actuator to move the implantable device when coupled to the implantable device, and wherein the proximal expandable basket includes a distal end that is fixed on the connecting member, wherein the distal expandable basket is deployable against the inner wall of the coronary sinus adjacent the mitral valve annulus, the proximal expandable basket is deployable against the inner wall or at an entrance of the coronary sinus, and the implantable device is configured to reshape the coronary sinus.

2. The medical device as in claim 1 wherein each of the distal expandable basket and the proximal expandable basket includes a strut assembly that is collapsible and expandable, the delivery sheath constrains each of the distal expandable basket and the proximal expandable basket, and retraction of the delivery sheath allows deployment of the distal expandable basket and the proximal expandable basket.

3. The medical device as in claim 1 wherein the distal expandable basket is engageable to an inner wall of a blood vessel, the proximal expandable basket is engageable to the inner wall of the blood vessel, the connecting member is deployable on a side of the inner wall of the blood vessel, and the medical device reshapes the blood vessel when implanted.

4. The medical device as in claim 1 wherein each of the distal expandable basket and the proximal expandable basket are comprised of a shaped-memory material.

5. The medical device as in claim 1 wherein the distal expandable basket includes a distal end that is fixed on the connecting member and a proximal end that is slideable along the connecting member.

6. The medical device as in claim 1 wherein the distal expandable basket includes a distal end that is slideable along the connecting member.

7. The medical device of claim 1, wherein the connecting member is configured to be in immediate contact with the inner wall of the coronary sinus, and has a surface to prevent the connecting member from cutting through the wall of the coronary sinus.

8. The medical device of claim 1, wherein each of the distal and proximal expandable baskets comprise a self expanding material having deployment rings having a zigzag pattern which forms peaks and valleys, and intermediate links connecting to the peaks; and wherein the self expanding material is a metal or alloy.

9. The medical device of claim 8, wherein the connecting member is configured to reshape the size of the mitral valve annulus.

10. The medical device of claim 9, wherein the distal end of each of the proximal expandable basket and the distal expandable basket comprises a hollow collar which is rotatably attached to the connecting member.

11. The medical device of claim 1, wherein both the proximal and distal end of both the proximal expandable basket and the distal expandable basket are shaped as truncated cones.

12. A medical device, comprising:

a delivery sheath;

an implantable device moveably disposed within the delivery sheath;

the implantable device further comprises a distal expandable basket and a different proximal expandable basket connected by a connecting member, wherein the connecting member is coupled at a first end to a proximal end of the distal expandable basket and at a second end to a distal end of the proximal expandable basket, wherein the proximal end of the distal expandable basket and a proximal end of the proximal expandable basket are both slideable along the connecting member when the expandable baskets are expanding and collapsing, and wherein the distal end of the distal expandable basket and the distal end of the proximal expandable basket are both shaped as truncated cones;

each of the distal expandable basket and proximal expandable basket being collapsed during delivery and expanded after deployment, wherein the delivery sheath constrains the distal expandable basket and the proximal expandable basket until deployment; and an actuator releasably coupling to the implantable device at a portion of the connecting member, the actuator to move the implantable device when coupled to the implantable device, and wherein the proximal expandable basket includes a distal end that is fixed on the connecting member, wherein the distal expandable basket is deployable against the inner wall of the coronary vein adjacent the mitral valve annulus, the proximal expandable basket is deployable against the inner wall or at an entrance of a coronary sinus, wherein the coronary vein and the coronary sinus are part of a vessel and the implantable device is configured to reshape the vessel.

13. The medical device of claim 12, wherein both the proximal and distal end of both the proximal expandable basket and the distal expandable basket are shaped as truncated cones.

14. A medical device, comprising:

an implantable device moveably disposed within a delivery sheath;

the implantable device further comprises a distal expandable basket and a different proximal expandable basket connected by a connecting member, wherein both ends of each of the proximal expandable basket and the distal expandable basket converge onto the connecting member;

the connecting member is coupled at a first end to a proximal end of the distal expandable basket and at a second end to a distal end of the proximal expandable basket, wherein the proximal end of the distal expandable basket and a proximal end of the proximal expandable basket are both slideable along the connecting member when the expandable baskets are expanding and collapsing, and wherein the distal end of the distal expandable basket and the distal end of the proximal expandable basket are both shaped as truncated cones; and an actuator is releaseably coupled to the implantable device at a portion of the connecting member, the actuator to move the implantable device when coupled to the implantable device, wherein the distal expandable basket is deployable against the inner wall of the coronary sinus adjacent a mitral valve annulus, the proximal expandable basket is deployable against the inner wall or at an entrance of the coronary sinus, and the implantable device is configured to reshape the coronary sinus.

15. The medical device of claim 14 wherein each of the distal expandable basket and the proximal expandable basket is collapsed during delivery and expanded after deployment, and the delivery sheath constrains the distal expandable basket and the proximal expandable basket until deployment.

16. The medical device of claim 14 wherein the proximal expandable basket includes a distal end that is slideable along the connecting member.

17. The medical device of claim 14 wherein each of the distal expandable basket and the proximal expandable basket are comprised of a shaped-memory material.

18. The medical device of claim 14 wherein the distal expandable basket includes a distal end that is fixed on the connecting member and a proximal end that is slideable along the connecting member.

19. The medical device of claim 14 wherein the distal expandable basket includes a distal end that is slideable along the connecting member.

20. The medical device of claim 14 wherein the actuator is used to apply tension on the distal expanding basket, the proximal expanding basket and the connecting member to reshape a vessel in which the medical device is deployed when implanted.

21. The medical device of claim 14 wherein the proximal expandable basket is deployed outside of the ostium of the coronary sinus in the right atrium and held against the ostium when deployed.

22. The medical device of claim 14 wherein the delivery sheath is advanced over the proximal expandable basket and/or the distal expandable basket to collapse the proximal expandable basket and/or the distal expandable basket to allow for repositioning or adjustment.

23. The medical device of claim 14 wherein the actuator is releaseably coupled to the implantable device in a way that allows the actuator to engage, disengage, attach or detach from the implantable device.

24. The medical device of claim 14 wherein both the proximal and distal ends of both the proximal expandable basket and the distal expandable basket are shaped as truncated cones.

25. The medical device of claim 14 wherein the distal ends of the proximal expandable basket and the distal expandable basket are fixed on the connecting member but the proximal ends of both baskets are not fixed on the connecting member.

26. The medical device of claim 14 wherein both ends of the proximal expandable basket are not fixed on the connecting member and a distal stop is placed on the connecting member distal to the distal end of the proximal expandable basket to define the distal travel distance for the proximal expandable basket.

27. The medical device of claim 14 wherein both ends of the proximal expandable basket are not fixed on the connecting member and a proximal end lock is placed on the connecting member to determine the position of the proximal expandable basket on the connecting member.

28. The medical device of claim 14, wherein the connecting member is configured to be in immediate contact with the inner wall of the coronary sinus, and has a surface to prevent the connecting member from cutting through the wall of the coronary sinus.

29. The medical device of claim 14, wherein each of the distal and proximal expandable baskets comprise a self expanding material having deployment rings having a zigzag pattern which forms peaks and valleys, and intermediate links connecting to the peaks; and wherein the self expanding material is a metal or alloy.

30. The medical device of claim 29, wherein the connecting member is configured to reshape the size of the mitral valve annulus.

31. The medical device of claim 30, wherein the distal end of each of the proximal expandable basket and the distal expandable basket comprises a hollow collar which is rotatably attached to the connecting member.

32. A medical device, comprising:

an implantable device moveably disposed within a delivery sheath;

the implantable device further comprises a distal expandable basket and a different proximal expandable basket connected by a connecting member, wherein both ends of each of the proximal expandable basket and the distal expandable basket converge onto the connecting member;

the connecting member is coupled at a first end to a proximal end of the distal expandable basket and at a second end to a distal end of the proximal expandable basket, wherein the proximal end of the distal expandable basket and a proximal end of the proximal expandable basket are both slideable along the connecting member when the expandable baskets are expanding and collapsing, and wherein the distal end of the distal expandable basket and the distal end of the proximal expandable basket are both shaped as truncated cones; and an actuator is releaseably coupled to the implantable device at a portion of the connecting member, the actuator to move the implantable device when coupled to the implantable device, wherein the distal expandable basket is deployable against the inner wall of the coronary sinus adjacent a mitral valve annulus, the proximal expandable basket is deployable against the inner wall or at an entrance of the coronary sinus, and the implantable device is configured to reshape the coronary sinus, wherein both ends of the proximal expandable basket are not fixed on the connecting member and a distal stop is placed on the connecting member distal to the distal end of the proximal expandable basket to define the distal travel distance for the proximal expandable basket and a proximal end lock is placed on the connecting member to determine the position of the proximal expandable basket on the connecting member, wherein each of the distal and proximal expandable baskets comprise a self expanding material having deployment rings having a zigzag pattern which forms peaks and valleys, and intermediate links connecting to the peaks; and wherein the self expanding material is a metal or alloy.

33. The medical device of claim 32 wherein each of the distal expandable basket and the proximal expandable basket includes a proximal and a distal strut assembly that is attached at a first end to a collar and at a second end to a deployment ring having pleats.

* * * * *